United States Patent
Wright

(10) Patent No.: US 10,618,979 B2
(45) Date of Patent: Apr. 14, 2020

(54) MULTISPECIFIC ANTIBODIES

(71) Applicant: UCB BIOPHARMA SPRL, Brussels (BE)

(72) Inventor: Michael John Wright, Slough (GB)

(73) Assignee: UCB Biopharma SPRL, Brussels (BE)

( * ) Notice: Subject to any disclaimer, the term of this patent is extended or adjusted under 35 U.S.C. 154(b) by 0 days.

(21) Appl. No.: 15/779,421

(22) PCT Filed: Dec. 1, 2016

(86) PCT No.: PCT/EP2016/079432
§ 371 (c)(1),
(2) Date: May 25, 2018

(87) PCT Pub. No.: WO2017/093404
PCT Pub. Date: Jun. 8, 2017

(65) Prior Publication Data
US 2018/0334513 A1  Nov. 22, 2018

(30) Foreign Application Priority Data
Dec. 3, 2015  (GB) .................................. 1521391.1

(51) Int. Cl.
C07K 16/18  (2006.01)
C07K 16/46  (2006.01)
C07K 16/00  (2006.01)
C07K 16/14  (2006.01)

(52) U.S. Cl.
CPC ............ C07K 16/468 (2013.01); C07K 16/00 (2013.01); C07K 16/14 (2013.01); *C07K 2317/55* (2013.01); *C07K 2317/622* (2013.01); *C07K 2319/00* (2013.01)

(58) Field of Classification Search
CPC ............... C07K 2317/31; C07K 16/16; C07K 2317/622; C07K 2317/55; C07K 2317/92; C07K 2317/35; C07K 2317/515; C07K 2317/52; C07K 2317/522; C07K 2317/524; C07K 2317/526; C07K 2317/24; C07K 2039/505; C07K 16/28
See application file for complete search history.

(56) References Cited

U.S. PATENT DOCUMENTS

| 4,741,900 A | 5/1988 | Alvarez et al. |
| 5,223,409 A | 6/1993 | Ladner et al. |
| 5,403,484 A | 4/1995 | Ladner et al. |
| 5,427,908 A | 6/1995 | Dower et al. |
| 5,516,637 A | 5/1996 | Huang et al. |
| 5,545,806 A | 8/1996 | Lonberg et al. |
| 5,569,825 A | 10/1996 | Lonberg et al. |
| 5,571,698 A | 11/1996 | Ladner et al. |
| 5,580,717 A | 12/1996 | Dower et al. |
| 5,585,089 A | 12/1996 | Queen et al. |
| 5,625,126 A | 4/1997 | Lonberg et al. |
| 5,633,425 A | 5/1997 | Lonberg et al. |
| 5,658,727 A | 8/1997 | Barbas et al. |
| 5,661,016 A | 8/1997 | Lonberg et al. |
| 5,698,426 A | 12/1997 | Huse |
| 5,731,168 A | 3/1998 | Carter et al. |
| 5,733,743 A | 3/1998 | Johnson et al. |
| 5,750,753 A | 5/1998 | Kimae et al. |
| 5,770,429 A | 6/1998 | Lonberg et al. |
| 5,780,225 A | 7/1998 | Wigler et al. |
| 5,798,229 A | 8/1998 | Strittmatter et al. |
| 5,821,047 A | 10/1998 | Garrard et al. |
| 5,969,108 A | 10/1999 | McCafferty et al. |
| 6,010,902 A | 1/2000 | Ledbetter et al. |
| 6,106,834 A | 8/2000 | Lazarovits et al. |
| 6,809,185 B1 | 10/2004 | Schoonjans et al. |
| 7,183,076 B2 | 2/2007 | Arathoon et al. |
| 8,088,378 B2 | 1/2012 | Chen et al. |
| 8,409,577 B2 | 4/2013 | Thompson et al. |
| 10,358,493 B2 | 7/2019 | Finney et al. |
| 10,370,447 B2 | 8/2019 | Finney et al. |
| 2003/0027247 A1 | 2/2003 | Wang et al. |
| 2003/0202975 A1 | 10/2003 | Tedder |
| 2005/0033031 A1 | 2/2005 | Cuoto |

(Continued)

FOREIGN PATENT DOCUMENTS

| EP | 0392745 A2 | 10/1990 |
| EP | 0438474 B1 | 5/1996 |

(Continued)

OTHER PUBLICATIONS

Lloyd et al., Protein Engineering, Design & Selection 22:159-168 (Year: 2009).*
Edwards et al., J Mol Biol 334(1): 103-118 (Year: 2003).*
Adair et al., "Therapeutic Antibodies," Drug Design Reviews Online 2(3):209-217 (2005).
Altschul et al., "Basic local alignment search tool," J Mol Biol 215(3):403-410 (1990).
Altschul et al., "Gapped BLAST and PSI-BLAST: a new generation of protein database search programs," Nucleic Acids Res 25(17):3389-3402 (1997).

(Continued)

*Primary Examiner* — Phuong Huynh
(74) *Attorney, Agent, or Firm* — Medler Ferro Woodhouse & Mills PLLC

(57) ABSTRACT

The present invention relates to heterodimerically-tethered bispecific protein complexes (according to the general formula of $(A-X)_2:(Y-B)_2$) and libraries/multiplexes thereof for use in research and therapy and in particular an in vitro/ex vivo method of detecting synergistic biological function of otherwise unknown pairs of targets. Such complexes may be used to capture soluble molecules secreted from a particular cell, in therapy, in research and for experimental purposes such as in assays to characterise patient populations by identifying cell populations relevant to a pathology or prognosis.

11 Claims, 3 Drawing Sheets
Specification includes a Sequence Listing.

(56) References Cited

U.S. PATENT DOCUMENTS

| | | |
|---|---|---|
| 2005/0048578 A1 | 3/2005 | Zhang |
| 2006/0252130 A1 | 11/2006 | Boehm et al. |
| 2007/0141672 A1 | 6/2007 | Shin |
| 2011/0076270 A1 | 3/2011 | Aversa et al. |
| 2013/0142787 A1 | 6/2013 | Chang et al. |
| 2013/0209463 A1 | 8/2013 | Rotman et al. |
| 2013/0336977 A1 | 12/2013 | Thompson et al. |
| 2014/0099254 A1 | 4/2014 | Chang et al. |
| 2014/0212425 A1 | 7/2014 | Chang et al. |
| 2015/0239974 A1 | 8/2015 | Chang et al. |
| 2017/0081404 A1 | 3/2017 | Finney et al. |
| 2017/0204178 A1 | 7/2017 | Finney et al. |
| 2017/0204183 A1 | 7/2017 | Finney et al. |
| 2018/0201678 A1 | 7/2018 | Finney et al. |
| 2018/0237521 A1 | 8/2018 | Finney et al. |
| 2018/0273620 A1 | 9/2018 | Finney et al. |
| 2018/0334513 A1 | 11/2018 | Wright |
| 2018/0334514 A1 | 11/2018 | Wright |
| 2018/0346603 A1 | 12/2018 | Bhatta et al. |
| 2018/0346604 A1 | 12/2018 | Rapecki |
| 2018/0355063 A1 | 12/2018 | Finney |
| 2019/0322739 A1 | 10/2019 | Finney et al. |

FOREIGN PATENT DOCUMENTS

| | | |
|---|---|---|
| EP | 0463151 B1 | 6/1996 |
| EP | 0546073 B1 | 9/1997 |
| EP | 1242457 B1 | 8/2004 |
| EP | 1570267 B1 | 10/2011 |
| EP | 2706069 A1 | 3/2014 |
| WO | WO86/01533 A1 | 3/1986 |
| WO | WO89/00195 A1 | 1/1989 |
| WO | WO89/01476 A1 | 2/1989 |
| WO | WO90/02809 A1 | 3/1990 |
| WO | WO91/09967 A1 | 7/1991 |
| WO | WO91/10737 A1 | 7/1991 |
| WO | WO92/01047 A1 | 1/1992 |
| WO | WO92/02551 A1 | 2/1992 |
| WO | WO92/18619 A1 | 10/1992 |
| WO | WO92/22583 A1 | 12/1992 |
| WO | WO93/06231 A1 | 4/1993 |
| WO | WO93/11162 A1 | 6/1993 |
| WO | WO93/11236 A1 | 6/1993 |
| WO | WO95/15982 A1 | 6/1995 |
| WO | WO95/20401 A1 | 8/1995 |
| WO | WO96/26964 A1 | 9/1996 |
| WO | WO98/20734 A1 | 5/1998 |
| WO | WO02/072832 A2 | 9/2002 |
| WO | WO03/012069 A2 | 2/2003 |
| WO | WO03/031581 A2 | 4/2003 |
| WO | WO03/048327 A2 | 6/2003 |
| WO | WO03/093320 A2 | 11/2003 |
| WO | WO2004/039840 A1 | 5/2004 |
| WO | WO2004/051268 A1 | 6/2004 |
| WO | WO2004/081051 A1 | 9/2004 |
| WO | WO2004/106377 A1 | 12/2004 |
| WO | WO2005/003169 A2 | 1/2005 |
| WO | WO2005/003170 A2 | 1/2005 |
| WO | WO2005/003171 A2 | 1/2005 |
| WO | WO2005/026210 A2 | 3/2005 |
| WO | WO2005/113605 A1 | 12/2005 |
| WO | WO2005/117984 A2 | 12/2005 |
| WO | WO2005/118642 A2 | 12/2005 |
| WO | WO2006/004910 A2 | 1/2006 |
| WO | WO2006/119897 A2 | 11/2006 |
| WO | WO2007/060406 A1 | 5/2007 |
| WO | WO2007/085837 A1 | 8/2007 |
| WO | WO2007/087453 A2 | 8/2007 |
| WO | WO2007/146968 A2 | 12/2007 |
| WO | WO2008/070569 A2 | 6/2008 |
| WO | WO2008/119353 A1 | 10/2008 |
| WO | WO2009/012268 A1 | 1/2009 |
| WO | WO2009/040562 A1 | 4/2009 |
| WO | WO2010/035012 A1 | 4/2010 |
| WO | WO2011/025904 A1 | 3/2011 |
| WO | WO2011/061492 A2 | 5/2011 |
| WO | WO2011/086091 A1 | 7/2011 |
| WO | WO2011/130305 A2 | 10/2011 |
| WO | WO2011/131746 A2 | 10/2011 |
| WO | WO2012/023053 A2 | 2/2012 |
| WO | WO2012/116453 A1 | 9/2012 |
| WO | WO2012/151199 A1 | 11/2012 |
| WO | WO2012/162561 A2 | 11/2012 |
| WO | WO2013/060867 A2 | 5/2013 |
| WO | WO2013/078455 A2 | 5/2013 |
| WO | WO2013/085893 A1 | 6/2013 |
| WO | WO2014/001326 A1 | 1/2014 |
| WO | WO2014/011518 A1 | 1/2014 |
| WO | WO2014/011519 A1 | 1/2014 |
| WO | WO2014/011520 A1 | 1/2014 |
| WO | WO2014/011521 A1 | 1/2014 |
| WO | WO2014/096390 A1 | 6/2014 |
| WO | WO2014/131694 A1 | 9/2014 |
| WO | WO2015/021089 A1 | 2/2015 |
| WO | WO2015/057834 A1 | 4/2015 |
| WO | WO2015/181282 A1 | 12/2015 |
| WO | WO2015/197772 A1 | 12/2015 |
| WO | WO2015/197789 A1 | 12/2015 |
| WO | WO2016/009029 A1 | 1/2016 |
| WO | WO2016/009030 A2 | 1/2016 |
| WO | WO2016/168773 A2 | 10/2016 |
| WO | WO2017/009473 A1 | 1/2017 |
| WO | WO2017/009476 A1 | 1/2017 |
| WO | WO2017/093402 A1 | 6/2017 |
| WO | WO2017/093406 A1 | 6/2017 |
| WO | WO2017/093408 A1 | 6/2017 |
| WO | WO2017/093410 A1 | 6/2017 |

OTHER PUBLICATIONS

Ames et al., "Conversion of murine Fabs isolated from a combinatorial phage display library to full length immunoglobulins," J Immunol Methods 184(2):177-186 (1995).

Angal et al., "A single amino acid substitution abolishes the heterogeneity of chimeric mouse/human (IgG4) antibody," Mol Immunol 30(1):105-108 (1993).

Armour et al., "Recombinant human IgG molecules lacking Fcgamma receptor I binding and monocyte triggering activities," Eur J Immunol 29(8):2613-2624 (1999).

Arndt et al., "Costimulation improves the killing capability of T cells redirected to tumor cells expressing low levels of CD33: description of a novel modular targeting system," *Leukemia* 28:59-69 (2014).

Babcook et al., "A novel strategy for generating monoclonal antibodies from single, isolated lymphocytes producing antibodies of defined specificities," Proc Natl Acad Sci USA 93(15):7843-7848 (1996).

Bartalena et al., "Thyroid hormone transport proteins," Clin Lab Med 13(3):583-598 (1993).

Berger et al., "Antigen recognition by conformational selection," FEBS Lett 450:149-153 (1999).

Bradshaw et al., "Concurrent detection of secreted products from human lymphocytes by microengraving: cytokines and antigen-reactive antibodies," Clin Immunol 129(1):10-18 (2008).

Bree et al., "Pharmacokinetics of intravenously administered 125I-labelled human alpha 1-acid glycoprotein," Clin Pharmacokinet 11(4):336-342 (1986).

Brinkmann et al., "Phage display of disulfide-stabilized Fv fragments," J Immunol Methods 182(1):41-50 (1995).

Brosterhus et al., "Enrichment and detection of live antigen-specific CD4(+) and CD8(+) T cells based on cytokine secretion," Eur J Immunol 29(12):4053-4059 (1999).

Bruhns et al., "Specificity and affinity of human Fcgamma receptors and their polymorphic variants for human IgG subclasses," Blood 113(16):3716-3725 (2009).

Burton et al., "Human antibodies from combinatorial libraries," Adv Immunol 57:191-280 (1994).

Caldas et al., "Humanization of the anti-CD18 antibody 6.7: an unexpected effect of a framework residue in binding to antigen," Mol Immunol 39:941-952 (2003).

(56) References Cited

OTHER PUBLICATIONS

Campbell et al., "Rapid detection, enrichment and propagation of specific T cell subsets based on cytokine secretion," *Clin Exp Immunol* 163:1-10 (2010).
Carnahan et al., "Epratuzumab, a CD22-targeting recombinant humanized antibody with a different mode of action from rituximab," Molecular Immunology 44(6):1331-1341 (2007).
Casset et al., "A peptide mimetic of an anti-CD4 monoclonal antibody by rational design," Biochem Biophys Res Comm 307:198-205 (2003).
Chan et al., "Therapeutic antibodies for autoimmunity and inflammation," Nat Rev Immunol 10(5):301-316 (2010).
Chang et al., "Loop-Sequence Features and Stability Determinants in Antibody Variable Domains by High-Throughput Experiments," Structure 22:9-21 (2014).
Chen et al., "Enhancement and destruction of antibody function by somatic mutation: unequal occurrence is controlled by V gene combinatorial associations," *EMBO J* 14(12):2784-2794 (1995).
Chien et al., "Significant structural and functional change of an antigen-binding site by a distant amino acid substitution: Proposal of a structural mechanism," Proc Natl Acad Sci USA 86:5532-5536 (1989).
Chothia et al., "Canonical structures for the hypervariable regions of immunoglobulins," J Mol Biol 196(4):901-917 (1987).
Chu et al., "Suppression of rheumatoid arthritis B cells by XmAb5871, an anti-CD19 antibody that coengages B cell antigen receptor complex and Fcγ receptor IIb inhibitory receptor," Arthritis Rheumatol 66:1153-1164 (2014).
Clargo et al., "The rapid generation of recombinant functional monoclonal antibodies from individual, antigen-specific bone marrow-derived plasma cells isolated using a novel fluorescence-based method," MAbs 6(1):143-159 (2014).
Crameri et al., "DNA shuffling of a family of genes from diverse species accelerates directed evolution," Nature 391:288-291 (1998).
Czerwinski et al., "Construction of dimeric F(ab) useful in blood group serology," Transfusion 42(2):257-264 (2002).
Datta-Mannan et al., "Humanized IgG1 variants with differential binding properties to the neonatal Fc receptor: relationship to pharmacokinetics in mice and primates," Drug Metab Dispos 35(1):86-94 (2007).
De Pascalis et al., "Grafting of 'Abbreviated' Complementarity-Determining Regions Containing Specificity-Determining Residues Essential for Ligand Contact to Engineer a Less Immunogenic Humanized Monoclonal Antibody," J Immunol 169:3076-3084 (2002).
Dennis et al., "Albumin Binding as a General Strategy for Improving the Pharmacokinetics of Proteins," J Biol Chem 277(38):35035-35043 (2002).
Dmitrova et al., "A new LexA-based genetic system for monitoring and analyzing protein heterodimerization in *Escherichia coli*," *Mol Gen Genet* 257:205-212 (1998).
Doerner et al., "Therapeutic antibody engineering by high efficiency cell screening," *FEBS Lett* 588:278-287 (2014).
Dubowchik et al., "Receptor-mediated and enzyme-dependent targeting of cytotoxic anticancer drugs," Pharmacol Ther 83(2):67-123 (1999).
Dunkin et al., "Immune cell therapy in IBD," Dig Dis 32:61-66 (2014).
Feldman et al., "Adoptive Cell Therapy—Tumor-Infiltrating Lymphocytes, T-Cell Receptors, and Chimeric Antigen Receptors," Semin Oncol 42(4):626-639 (2015).
Finney et al., "Chimeric receptors providing both primary and costimulatory signaling in T cells from a single gene product," J Immunol 161:2791-2797 (1998).
Gish et al., "Identification of protein coding regions by database similarity search," Nat Genet 3(3):266-272 (1993).
Gitlin et al., "The selectivity of the human placenta in the transer of plasma proteins from mother to fetus," J Clin Invest 43:1938-1951 (1964).

Giusti et al., "Somatic diversification of S107 from an antiphosphocoline to an anti-DNA autoantibody is due to a single base change in its heavy chain variable region," Proc Natl Acad Sci USA 84:2926-2930 (1987).
Glockshuber et al., "A comparison of strategies to stabilize immunoglobulin Fv-fragments," Biochemistry 29(6):1362-1367 (1990).
Gold et al., "The B Cell Antigen Receptor Activates the Akt (Protein Kinase B)/Glycogen Synthase Kinase-3 Signaling Pathway via Phosphatidylinositol 3-Kinase," *J Immunol* 163:1894-1905 (1999).
Goldenberg et al., "Multifunctional Antibodies by the Dock-and-Lock Method for Improved Cancer Imaging and Therapy by Pretargeting," *J Nuc Med* 49(1):158-163 (2008).
Gussow et al., "Humanization of Monoclonal Antibodies," Meth Enzymol 203:99-121 (1991).
Hanes et al., "Ribosome display efficiently selects and evolves high-affinity antibodies in vitro from immune libraries," *Proc Natl Acad Sci USA* 95:14130-14135 (1998).
Harris, "Processing of C-terminal lysine and arginine residues of proteins isolated from mammalian cell culture," J Chromatogr A 705(1):129-134 (1995).
Hermiston et al., "CD45: A Critical Regulator of Signaling Thresholds in Immune Cells," Ann Rev Immunol 21:107-137 (2003).
Hinnebusch, "Evidence for translational regulation of the activator of general amino acid control in yeast," Proc Natl Acad Sci USA 81:6442-6446 (1984).
Hinton et al., "Engineered human IgG antibodies with longer serum half-lives in primates," J Biol Chem 279(8):6213-6216 (2004).
Hollinger et al., "Engineered antibody fragments and the rise of single domains," Nat Biotechnol 23(9):1126-1136 (2005).
Holm et al., "Functional mapping and single chain construction of the anti-cytokeratin 8 monoclonal antibody TS11," Mol Immunol 44:1075-1084 (2007).
Holmes, "Buy buy bispecific antibodies," Nat Rev Drug Discov 10(11):798-800 (2011).
Holt et al., "Anti-serum albumin domain antibodies for extending the half-lives of short lived drugs," Protein Eng Des Sel 21(5):283-288 (2008).
Hope et al., "GCN4 protein, synthesized in vitro, binds HIS3 regulatory sequences: implications for general control of amino acid biosynthetic genes in yeast," Cell 43(1):177-188 (1985).
Idusogie et al., "Mapping of the C1q binding site on rituxan, a chimeric antibody with a human IgG1 Fc," J Immunol 164(8):4178-1484 (2000).
Idusogie et al., "Engineered antibodies with increased activity to recruit complement," J Immunol 166(4):2571-2575 (2001).
Jourdan et al., "An in vitro model of differentiation of memory B cells into plasmablasts and plasma cells including detailed phenotypic and molecular characterization," Blood 114(25):5173-5181 (2009).
Jung et al., "Design of interchain disulfide bonds in the framework region of the Fv fragment of the monoclonal antibody B3," Proteins 19(1):35-47 (1994).
Karnell et al., "CD19 and CD32b Differentially Regulate Human B Cell Responsiveness," J Immunol 192(4):1480-1490 (2014).
Kashmiri et al., "SDR grafting—a new approach to antibody humanization," Methods 36(1):25-34 (2005).
Keller et al., "Independent Metalloregulation of Ace1 and Mac1 in *Saccharomyces cerevisiae*," Eukaryot Cell 4(11):1863-1871 (2005).
Kettleborough et al., "Isolation of tumor cell-specific single-chain Fv from immunized mice using phage-antibody libraries and the re-construction of whole antibodies from these antibody fragments," Eur J Immunol 24(4):952-958 (1994).
Ko et al., "Engineering Antibodies for Dual Specificity and Enhanced Potency," *Biotechnol Bioprocess Eng* 20:201-210 (2015).
Kohler et al., "Continuous cultures of fused cells secreting antibody of predefined specificity," Nature 256:495-497 (1975).
Konterman et al., "Dual targeting strategies with bispecific antibodies," *mAbs*, 4(2):182-197 (2012).
Kozbor et al., "The production of monoclonal antibodies from human lymphocytes," Immunol Today 4(3):72-79 (1983).
Kudo et al., "T lymphocytes expressing a CD16 signaling receptor exert antibody-dependent cancer cell killing," Cancer Res 74(1):93-103 (2014).

(56) References Cited

OTHER PUBLICATIONS

Labrijn et al., "Therapeutic IgG4 antibodies engage in Fab-arm exchange with endogenous human IgG4 in vivo," Nat Biotechnol 27(8):767-771 (2009).
Lazar et al., "Engineered antibody Fc variants with enhanced effector function," Proc Natl Acad Sci USA 103(11):4005-4010 (2006).
Love et al., "A microengraving method for rapid selection of single cells producing antigen-specific antibodies," Nat Biotechnol 24(6):703-707 (2006).
Low et al., "Mimicking Somatic Hypermutation: Affinity Maturation of Antibodies Displayed on Bacteriophage Using a Bacterial Mutator Strain," J Mol Biol 260(3):359-368 (1996).
Luo et al., "Vl-linker-Vh orientation-dependent expression of single chain Fv-containing an engineered disulfide-stabilized bond in the framework regions," J Biochem 118(4):825-831 (1995).
Luo et al., "Design and Applications of Bispecific Heterodimers: Molecular Imaging and Beyond," *Mol Pharm* 11:1750-1761 (2014).
MacCallum et al., "Antibody-antigen Interactions: Contact Analysis and Binding Site Topography," J Mol Biol 262:732-745 (1996).
Madden et al., "Applications of network BLAST server," Methods Enzymol 266:131-141 (1996).
Mahoney et al., "Combination cancer immunotherapy and new immunomodulatory targets," Nat Rev Drug Discov 14:561-584 (2015).
Mariuzza et al., "The Structural Basis of Antigen-Antibody Recognition," Ann Rev Biophys Biophys Chem 16:139-159 (1987).
Marks et al., "By-passing immunization: building high affinity human antibodies by chain shuffling," Bio/Technology 10(7):779-783 (1992).
Merchant et al., "An efficient route to human bispecific IgG," Nat Biotechnol 16(7):677-681 (1998).
Moore et al., "Application of dual affinity retargeting molecules to achieve optimal redirected T-cell killing of B-cell lymphoma," Blood 117(17):4542-4551 (2011).
Muller et al., "Bispecific antibodies for cancer immunotherapy: Current perspectives," BioDrugs 24:89-98 (2010).
Nunez-Prado et al., "The coming of age of engineered multivalent antibodies," Drug Discov Today 20(5):588-594 (2015).
Nygren et al., "Scaffolds for engineering novel binding sites in proteins," Curr Opin Struct Biol 7(4):463-469 (1997).
Patten et al., "Applications of DNA shuffling to pharmaceuticals and vaccines," Curr Opin Biotechnol 8(6):724-733 (1997).
Persic et al., "An integrated vector system for the eukaryotic expression of antibodies or their fragments after selection from phage display libraries," Gene 187(1):9-18 (1997).
Pfeifer et al., "Anti-CD22 and anti-CD79B antibody drug conjugates are active in different molecular diffuse large B-cell lymphoma subtypes," *Leukemia* 29:1578-1586 (2015).
Peters, "Serum albumin," Adv Protein Chem 37:161-245 (1985).
Pule et al., "Artificial T-cell receptors," Cytotherapy 5(3):211-226 (2003).
Rajagopal et al., "A form of anti-Tac(Fv) which is both single-chain and disulfide stabilized: comparison with its single-chain and disulfide-stabilized homologs," Protein Eng 10(12):1453-1459 (1997).
Reiter et al., "Stabilization of the Fv fragments in recombinant immunotoxins by disulfide bonds engineered into conserved framework regions," Biochemistry 33(18):5451-5159 (1994).
Reiter et al., "Improved binding and antitumor activity of a recombinant anti-erbB2 immunotoxin by disulfide stabilization of the Fv fragment," J Biol Chem 269(28):18327-18331 (1994).
Richards et al., "Optimization of antibody binding to FcgammaRIIa enhances macrophage phagocytosis of tumor cells," Mol Cancer Ther 7(8):2517-2527 (2008).
Ridgway et al., "'Knobs-into-holes' engineering of antibody CH3 domains for heavy chain heterodimerization," Protein Eng 9:617-621 (1996).
Rodgers et al., "Switch-mediated activation and retargeting of CAR-T cells for B-cell malignancies," *Proc Natl Acad Sci USA* 113(4):E459-E468 (2016).

Rudikoff et al., "Single amino acid substitution altering antigen-binding specificity," *Proc Natl Acad Sci USA* 79:1979-1983 (1982).
Ryan et al., "Antibody targeting of B-cell maturation antigen on malignant plasma cells," Mol Cancer Ther 6(11):3009-3018 (2007).
Schoonjans et al., "A new model for intermediate molecular weight recombinant bispecific and trispecific antibodies by efficient heterodimerization of single chain variable domains through fusion to a Fab-chain," *Biomol Eng* 17:193-202 (2001).
Shields et al., "High resolution mapping of the binding site on human IgG1 for Fc gamma RI, Fc gamma RII, Fc gamma RIII, and FcRn and design of IgG1 variants with improved binding to the Fc gamma R," J Biol Chem 276(9):6591-6604 (2001).
Spang et al., "Heterodimeric Barnase-Barstar Vaccine Molecules: Influence of One versus Two Targeting Units Specific for Antigen Presenting Cells," *PLoS ONE* 7(9):e45393 (2012).
Stavenhagen et al., "Enhancing the potency of therapeutic monoclonal antibodies via Fc optimization," Adv Enzyme Regul 48:152-164 (2008).
Stavenhagen et al., "Fc optimization of therapeutic antibodies enhances their ability to kill tumor cells in vitro and controls tumor expansion in vivo via low-affinity activating Fcgamma receptors," Cancer Res 16(18):8882-8890 (2007).
Steurer et al., "Ex vivo coating of islet cell allografts with murine CTLA4/Fc promotes graft tolerance," J Immunol 155(3):1165-1174 (1995).
Thireos et al., "5' untranslated sequences are required for the translational control of a yeast regulatory gene," Proc Natl Acad Sci USA 81:5096-5100 (1984).
Thompson et al., "Affinity maturation of a high-affinity human monoclonal antibody against the third hypervariable loop of human immunodeficiency virus: use of phage display to improve affinity and broaden strain reactivity," J Mol Biol 256(1):77-88 (1996).
Thorpe et al., "The preparation and cytotoxic properties of antibody-toxin conjugates," Immunol Rev 62:119-158 (1982).
Vaccaro et al., "Engineering the Fc region of immunoglobulin G to modulate in vivo antibody levels," Nat Biotechnol 23(10):1283-1288 (2005).
Vajdos et al., "Comprehensive Functional Maps of the Antigen-binding Site of an Anti-ErbB2 Antibody Obtained with Shotgun Scanning Mutagenesis," J Mol Biol 320:415-428 (2002).
Van Der Stegen et al., "The pharmacology of second-generation chimeric antigen receptors," Nat Rev Drug Discov 14:499-509 (2015).
Vaughan et al., "Human antibodies by design," Nat Biotechnol 16(6):535-539 (1998).
Veri et al., "Therapeutic Control of B Cell Activation via a Recruitment of Fcγ Receptor IIB (CD32B) Inhibitory Function with a Novel Bispecific Antibody Scaffold," *Arthritis Rheum* 62(7):1933-1943 (2010).
Verma et al., "Antibody engineering: comparison of bacterial, yeast, insect and mammalian expression systems," J Immunol Methods 216:165-181 (1998).
Waldemann et al, "Metabolism of immunoglobulins," Prog Allergy 13:1-110 (1969).
Walker et al., "CD22: an inhibitory enigma," Immunology 123(3):314-325 (2008).
Wang et al., "Antibody Engineering Using Phage Display with a Coiled-Coil Heterodimeric Fv Antibody Fragment," *PLoS ONE* 6(4):e19023 (2011).
Wienands, "The B-cell antigen receptor: formation of signaling complexes and the function of adaptor proteins," Curr Top Microbiol Immunol 245:53-76 (2000).
Willcox et al., "Production of soluble αβ T-cell receptor heterodimers suitable for biophysical analysis of ligand binding," *Protein Sci* 8:2418-2423 (1999).
Winkler et al., "Changing the Antigen Binding Specificity by Single Point Mutations of an Anti-p24 (HIV-1) Antibody," J Immunol 165:4505-4514 (2000).
Wu et al., "Humanization of a Murine Monoclonal Antibody by Simultaneous Optimization of Framework and CDR Residues," J Mol Biol 294:151-162 (1999).

(56) References Cited

OTHER PUBLICATIONS

Yang et al., "CDR walking mutagenesis for the affinity maturation of a potent human anti-HIV-1 antibody into the picomolar range," J Mol Biol 254(3):392-403 (1995).

Young et al., "Thermal stabilization of a single-chain Fv antibody fragment by introduction of a disulphide bond," FEBS Lett 377(2):135-139 (1995).

Yu et al., "Interaction between Bevacizumab and Murine VEGF-A: A Reassessment," *Invest Ophthalmol Vis Sci* 49(2):522-527 (2008).

Yu et al., "Rationalization and Design of the Complementarity Determining Region Sequences in an Antibody-Antigen Recognition Surface," PLOS One 7(3):e33340 (2012).

Zahnd et al., "Directed in Vitro Evolution and Crystallographic Analysis of a Peptide-binding Single Chain Antibody Fragment (scFv) with Low Picomolar Affinity," *J Biol Chem* 279(18):18870-18877 (2004).

Zhang et al., "PowerBLAST: a new network BLAST application for interactive or automated sequence analysis and annotation," Genome Res 7(6):649-656 (1997).

Zhu et al., "Remodeling domain interfaces to enhance heterodimer formation," Protein Sci 6(4):781-788 (1997).

International Search Report issued in PCT/EP2016/079432, dated Feb. 27, 2017.

Hernández-Molina et al., "The meaning of anti-Ro and anti-La antibodies in primary Sjögren's syndrome," Autoimmunity Reviews 10:123-125 (2011).

Non-Final Office Action issued in U.S. Appl. No. 15/311,198, dated Jul. 10, 2018.

Final Office Action issued in U.S. Appl. No. 15/311,198, dated Dec. 21, 2018.

Notice of Allowance issued in U.S. Appl. No. 15/311,198, dated Apr. 10, 2019.

Kussie et al., "A single engineered amino acid substitution changes antibody fine specificity" The Journal of Immunology (1994) 152:146-152.

Ward et al., "Binding activities of a repertoire of single immunoglobulin variable domains secreted from *Escherichia coli*," Nature (1989) 341:544-546.

Non-final Office Action dated Nov. 12, 2019, issued in U.S. Appl. No. 15/779,428.

\* cited by examiner

Fig. 2

|  | $A_1X$ | $A_2X$ | $A_3X$ | $A_4X$ |
|---|---|---|---|---|
| $B_1Y$ | $A_1X\ B_1Y$ | $A_2X\ B_1Y$ | $A_3X\ B_1Y$ | $A_4X\ B_1Y$ |
| $B_2Y$ | $A_1X\ B_2Y$ | $A_2X\ B_2Y$ | $A_3X\ B_2Y$ | $A_4X\ B_2Y$ |
| $B_3Y$ | $A_1X\ B_3Y$ | $A_2X\ B_3Y$ | $A_3X\ B_3Y$ | $A_4X\ B_3Y$ |
| $B_4Y$ | $A_1X\ B_4Y$ | $A_2X\ B_4Y$ | $A_3X\ B_4Y$ | $A_4X\ B_4Y$ |

SEQUENCE LISTING

<160> NUMBER OF SEQ ID NOS: 103

<210> SEQ ID NO 1
<211> LENGTH: 44
<212> TYPE: PRT
<213> ORGANISM: Artificial Sequence
<220> FEATURE:
<223> OTHER INFORMATION: CN4(7P14P) sequence

<400> SEQUENCE: 1

Ala Ser Gly Gly Gly Arg Met Lys Gln Leu Glu Pro Lys Val Glu Glu
1               5                   10                  15

Leu Leu Pro Lys Asn Tyr His Leu Glu Asn Glu Val Ala Arg Leu Lys
            20                  25                  30

Lys Leu Val Gly Glu Arg His His His His His His

<210> SEQ ID NO 2
<211> LENGTH: 132
<212> TYPE: DNA
<213> ORGANISM: Artificial Sequence
<220> FEATURE:
<223> OTHER INFORMATION: DNA encoding

<400> SEQUENCE: 2

```
gctagcggag gcggaagaat gaaacaactt gaacccaagg ttgaagaatt gcttccgaaa      60
aattatcact tggaaaatga ggttgccaga ttaaagaaat tagttggcga acgccatcac     120
catcaccatc ac                                                         132
```

<210> SEQ ID NO 3
<211> LENGTH: 262
<212> TYPE: PRT
<213> ORGANISM: Artificial Sequence
<220> FEATURE:
<223> OTHER INFORMATION: 52SR4 ds scFv sequence

<400> SEQUENCE: 3

```
Asp Ala Val Val Thr Gln Glu Ser Ala Leu Thr Ser Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Ser Trp Val Gln Glu Lys Pro Asp His Leu Phe Thr Gly
        35                  40                  45

Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Val Leu Trp Tyr Ser Asp
                85                  90                  95

His Trp Val Phe Gly Cys Gly Thr Lys Leu Thr Val Leu Gly Gly Gly
            100                 105                 110

Gly Gly Ser Gly Gly Gly Gly Ser Gly Gly Gly Gly Ser Gly Gly Gly
        115                 120                 125

Gly Ser Asp Val Gln Leu Gln Gln Ser Gly Pro Gly Leu Val Ala Pro
    130                 135                 140

Ser Gln Ser Leu Ser Ile Thr Cys Thr Val Ser Gly Phe Leu Leu Thr
145                 150                 155                 160

Asp Tyr Gly Val Asn Trp Val Arg Gln Ser Pro Gly Lys Cys Leu Glu
                165                 170                 175

Trp Leu Gly Val Ile Trp Gly Asp Gly Ile Thr Asp Tyr Asn Ser Ala
            180                 185                 190

Leu Lys Ser Arg Leu Ser Val Thr Lys Asp Asn Ser Lys Ser Gln Val
        195                 200                 205

Phe Leu Lys Met Asn Ser Leu Gln Ser Gly Asp Ser Ala Arg Tyr Tyr
    210                 215                 220

Cys Val Thr Gly Leu Phe Asp Tyr Trp Gly Gln Gly Thr Thr Leu Thr
225                 230                 235                 240

Val Ser Ser Ala Ala Ala His His His His His His Glu Gln Lys Leu
                245                 250                 255

Ile Ser Glu Glu Asp Leu
            260
```

<210> SEQ ID NO 4
<211> LENGTH: 792
<212> TYPE: DNA
<213> ORGANISM: Artificial Sequence
<220> FEATURE:
<223> OTHER INFORMATION: DNA encoding

<400> SEQUENCE: 4

```
gatgcggtgg tgacccagga aagcgcgctg accagcagcc cgggcgaaac cgtgaccctg      60
acctgccgca gcagcaccgg cgcggtgacc accagcaact atgcgagctg ggtgcaggaa     120
aaaccggatc atctgtttac cggcctgatt ggcggcacca caaccgcgc gccgggcgtg      180 ccggcgcgct ttagcggcag cctgattggc gataaagcgg cgctgaccat taccggcgcg     240
cagaccgaag atgaagcgat ttattttgc gtgctgtggt atagcgacca ttgggtgttt      300
ggctgcggca ccaaactgac cgtgctgggt ggaggcggtg gctcaggcgg aggtggctca     360
ggcggtggcg gtctggcgg cggcggcagc gatgtgcagc tgcagcagag cggcccgggc      420
ctggtggcgc cgagccagag cctgagcatt acctgcaccg tgagcggctt ctctcctgacc    480 gattatggcg tgaactgggt cgccagagc ccgggcaaat gcctggaatg gctgggcgtg      540
atttggggcg atggcattac cgattataac agcgcgctga aaagccgcct gagcgtgacc     600
aaagataaca gcaaaagcca ggtgtttctg aaaatgaaca gcctgcagag cggcgatagc     660
gcgcgctatt attgcgtgac cggcctgttt gattattggg gccagggcac cacccctgacc    720 gtgagcagcg cggccgccca tcaccatcac catcacgaac agaaactgat tagcgaagaa     780
gatctgtaat ag                                                         792
```

<210> SEQ ID NO 5
<211> LENGTH: 8
<212> TYPE: PRT
<213> ORGANISM: Artificial Sequence
<220> FEATURE:
<223> OTHER INFORMATION: FLEXIBLE PEPTIDE LINKER

<400> SEQUENCE: 5

Asp Lys Thr His Thr Cys Ala Ala
1               5

<210> SEQ ID NO 6
<211> LENGTH: 11
<212> TYPE: PRT
<213> ORGANISM: Artificial Sequence
<220> FEATURE:
<223> OTHER INFORMATION: FLEXIBLE PEPTIDE LINKER

<400> SEQUENCE: 6

Asp Lys Thr His Thr Cys Pro Pro Cys Pro Ala
1               5                   10

<210> SEQ ID NO 7
<211> LENGTH: 18
<212> TYPE: PRT
<213> ORGANISM: Artificial Sequence
<220> FEATURE:
<223> OTHER INFORMATION: FLEXIBLE PEPTIDE LINKER

<400> SEQUENCE: 7

Asp Lys Thr His Thr Cys Pro Pro Cys Pro Ala Thr Cys Pro Pro Cys
1               5                   10                  15

Pro Ala

```
<210> SEQ ID NO 8
<211> LENGTH: 25
<212> TYPE: PRT
<213> ORGANISM: Artificial Sequence
<220> FEATURE:
<223> OTHER INFORMATION: FLEXIBLE PEPTIDE LINKER

<400> SEQUENCE: 8

Asp Lys Thr His Thr Cys Pro Pro Cys Pro Ala Thr Cys Pro Pro Cys
1               5                   10                  15

Pro Ala Thr Cys Pro Pro Cys Pro Ala
            20                  25

<210> SEQ ID NO 9
<211> LENGTH: 30
<212> TYPE: PRT
<213> ORGANISM: Artificial Sequence
<220> FEATURE:
<223> OTHER INFORMATION: FLEXIBLE PEPTIDE LINKER

<400> SEQUENCE: 9

Asp Lys Thr His Thr Cys Pro Pro Cys Pro Ala Gly Lys Pro Thr Leu
1               5                   10                  15

Tyr Asn Ser Leu Val Met Ser Asp Thr Ala Gly Thr Cys Tyr
            20                  25                  30

<210> SEQ ID NO 10
<211> LENGTH: 31
<212> TYPE: PRT
<213> ORGANISM: Artificial Sequence
<220> FEATURE:
<223> OTHER INFORMATION: FLEXIBLE PEPTIDE LINKER

<400> SEQUENCE: 10

Asp Lys Thr His Thr Cys Pro Pro Cys Pro Ala Gly Lys Pro Thr His
1               5                   10                  15

Val Asn Val Ser Val Val Met Ala Glu Val Asp Gly Thr Cys Tyr
            20                  25                  30

<210> SEQ ID NO 11
<211> LENGTH: 15
<212> TYPE: PRT
<213> ORGANISM: Artificial Sequence
<220> FEATURE:
<223> OTHER INFORMATION: FLEXIBLE PEPTIDE LINKER

<400> SEQUENCE: 11

Asp Lys Thr His Thr Cys Cys Val Glu Cys Pro Pro Cys Pro Ala
1               5                   10                  15

<210> SEQ ID NO 12
<211> LENGTH: 26
<212> TYPE: PRT
<213> ORGANISM: Artificial Sequence
<220> FEATURE:
<223> OTHER INFORMATION: FLEXIBLE PEPTIDE LINKER

<400> SEQUENCE: 12

Asp Lys Thr His Thr Cys Pro Arg Cys Pro Glu Pro Lys Ser Cys Asp
1               5                   10                  15

Thr Pro Pro Pro Cys Pro Arg Cys Pro Ala
            20                  25

<210> SEQ ID NO 13
```

```
<211> LENGTH: 11
<212> TYPE: PRT
<213> ORGANISM: Artificial Sequence
<220> FEATURE:
<223> OTHER INFORMATION: FLEXIBLE PEPTIDE LINKER

<400> SEQUENCE: 13

Asp Lys Thr His Thr Cys Pro Ser Cys Pro Ala
1               5                   10

<210> SEQ ID NO 14
<211> LENGTH: 7
<212> TYPE: PRT
<213> ORGANISM: Artificial Sequence
<220> FEATURE:
<223> OTHER INFORMATION: Flexible linker

<400> SEQUENCE: 14

Ser Gly Gly Gly Gly Ser Glu
1               5

<210> SEQ ID NO 15
<211> LENGTH: 6
<212> TYPE: PRT
<213> ORGANISM: Artificial Sequence
<220> FEATURE:
<223> OTHER INFORMATION: Flexible linker

<400> SEQUENCE: 15

Asp Lys Thr His Thr Ser
1               5

<210> SEQ ID NO 16
<211> LENGTH: 6
<212> TYPE: PRT
<213> ORGANISM: Artificial Sequence
<220> FEATURE:
<223> OTHER INFORMATION: Flexible linker

<400> SEQUENCE: 16

Ser Gly Gly Gly Gly Ser
1               5

<210> SEQ ID NO 17
<211> LENGTH: 11
<212> TYPE: PRT
<213> ORGANISM: Artificial Sequence
<220> FEATURE:
<223> OTHER INFORMATION: Flexible linker

<400> SEQUENCE: 17

Ser Gly Gly Gly Gly Ser Gly Gly Gly Gly Ser
1               5                   10

<210> SEQ ID NO 18
<211> LENGTH: 16
<212> TYPE: PRT
<213> ORGANISM: Artificial Sequence
<220> FEATURE:
<223> OTHER INFORMATION: Flexible linker

<400> SEQUENCE: 18

Ser Gly Gly Gly Gly Ser Gly Gly Gly Ser Gly Gly Gly Gly Ser
1               5                   10                  15

<210> SEQ ID NO 19
<211> LENGTH: 21
```

```
<212> TYPE: PRT
<213> ORGANISM: Artificial Sequence
<220> FEATURE:
<223> OTHER INFORMATION: Flexible linker

<400> SEQUENCE: 19

Ser Gly Gly Gly Gly Ser Gly Gly Gly Gly Ser Gly Gly Gly Gly Ser
1               5                   10                  15

Gly Gly Gly Gly Ser
            20

<210> SEQ ID NO 20
<211> LENGTH: 26
<212> TYPE: PRT
<213> ORGANISM: Artificial Sequence
<220> FEATURE:
<223> OTHER INFORMATION: Flexible linker

<400> SEQUENCE: 20

Ser Gly Gly Gly Gly Ser Gly Gly Gly Gly Ser Gly Gly Gly Gly Ser
1               5                   10                  15

Gly Gly Gly Gly Ser Gly Gly Gly Gly Ser
            20                  25

<210> SEQ ID NO 21
<211> LENGTH: 11
<212> TYPE: PRT
<213> ORGANISM: Artificial Sequence
<220> FEATURE:
<223> OTHER INFORMATION: Flexible linker

<400> SEQUENCE: 21

Ala Ala Ala Gly Ser Gly Gly Ala Ser Ala Ser
1               5                   10

<210> SEQ ID NO 22
<211> LENGTH: 16
<212> TYPE: PRT
<213> ORGANISM: Artificial Sequence
<220> FEATURE:
<223> OTHER INFORMATION: Flexible linker
<220> FEATURE:
<221> NAME/KEY: misc_feature
<222> LOCATION: (7)..(7)
<223> OTHER INFORMATION: Xaa can be any naturally occurring amino acid

<400> SEQUENCE: 22

Ala Ala Ala Gly Ser Gly Xaa Gly Gly Gly Ser Gly Ala Ser Ala Ser
1               5                   10                  15

<210> SEQ ID NO 23
<211> LENGTH: 21
<212> TYPE: PRT
<213> ORGANISM: Artificial Sequence
<220> FEATURE:
<223> OTHER INFORMATION: Flexible linker
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 23

Ala Ala Ala Gly Ser Gly Xaa Gly Gly Gly Ser Xaa Gly Gly Gly Ser
1               5                   10                  15
```

Gly Ala Ser Ala Ser
            20

<210> SEQ ID NO 24
<211> LENGTH: 26
<212> TYPE: PRT
<213> ORGANISM: Artificial Sequence
<220> FEATURE:
<223> OTHER INFORMATION: Flexible linker
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 24

Ala Ala Ala Gly Ser Gly Xaa Gly Gly Gly Ser Xaa Gly Gly Gly Ser
1               5                   10                  15

Xaa Gly Gly Gly Ser Gly Ala Ser Ala Ser
            20                  25

<210> SEQ ID NO 25
<211> LENGTH: 31
<212> TYPE: PRT
<213> ORGANISM: Artificial Sequence
<220> FEATURE:
<223> OTHER INFORMATION: Flexible linker
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid

<400> SEQUENCE: 25

Ala Ala Ala Gly Ser Gly Xaa Gly Gly Gly Ser Xaa Gly Gly Gly Ser
1               5                   10                  15

Xaa Gly Gly Gly Ser Xaa Gly Gly Gly Ser Gly Ala Ser Ala Ser
            20                  25                  30

<210> SEQ ID NO 26
<211> LENGTH: 13
<212> TYPE: PRT
<213> ORGANISM: Artificial Sequence
<220> FEATURE:
<223> OTHER INFORMATION: Flexible linker
<220> FEATURE:
<221> NAME/KEY: misc_feature
<222> LOCATION: (7)..(7)
<223> OTHER INFORMATION: Xaa can be any naturally occurring amino acid

<400> SEQUENCE: 26

Ala Ala Ala Gly Ser Gly Xaa Ser Gly Ala Ser Ala Ser

-continued

```
<210> SEQ ID NO 27
<211> LENGTH: 28
<212> TYPE: PRT
<213> ORGANISM: Artificial Sequence
<220> FEATURE:
<223> OTHER INFORMATION: Flexible linker

<400> SEQUENCE: 27

Pro Gly Gly Asn Arg Gly Thr Thr Thr Arg Arg Pro Ala Thr Thr
1               5                   10                  15

Thr Gly Ser Ser Pro Gly Pro Thr Gln Ser His Tyr
            20                  25

<210> SEQ ID NO 28
<211> LENGTH: 11
<212> TYPE: PRT
<213> ORGANISM: Artificial Sequence
<220> FEATURE:
<223> OTHER INFORMATION: Flexible linker

<400> SEQUENCE: 28

Ala Thr Thr Thr Gly Ser Ser Pro Gly Pro Thr
1               5                   10

<210> SEQ ID NO 29
<211> LENGTH: 6
<212> TYPE: PRT
<213> ORGANISM: Artificial Sequence
<220> FEATURE:
<223> OTHER INFORMATION: Flexible linker

<400> SEQUENCE: 29

Ala Thr Thr Thr Gly Ser
1               5

<210> SEQ ID NO 30
<211> LENGTH: 13
<212> TYPE: PRT
<213> ORGANISM: Artificial Sequence
<220> FEATURE:
<223> OTHER INFORMATION: Flexible linker

<400> SEQUENCE: 30

Ala Ala Ala Ala Ala Ala Ala Ala Ala Ala Ala Ala Ala
1               5                   10

<210> SEQ ID NO 31
<211> LENGTH: 21
<212> TYPE: PRT
<213> ORGANISM: Artificial Sequence
<220> FEATURE:
<223> OTHER INFORMATION: Flexible linker

<400> SEQUENCE: 31

Glu Pro Ser Gly Pro Ile Ser Thr Ile Asn Ser Pro Pro Ser Lys Glu
1               5                   10                  15

Ser His Lys Ser Pro
            20

<210> SEQ ID NO 32
<211> LENGTH: 15
<212> TYPE: PRT
<213> ORGANISM: Artificial Sequence
<220> FEATURE:
```

```
<223> OTHER INFORMATION: Flexible linker

<400> SEQUENCE: 32

Gly Thr Val Ala Ala Pro Ser Val Phe Ile Phe Pro Pro Ser Asp
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Flexible linker

<400> SEQUENCE: 33

Gly Gly Gly Gly Ile Ala Pro Ser Met Val Gly Gly Gly Gly Ser
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Flexible linker

<400> SEQUENCE: 34

Gly Gly Gly Gly Lys Val Glu Gly Ala Gly Gly Gly Gly Gly Ser
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Flexible linker

<400> SEQUENCE: 35

Gly Gly Gly Gly Ser Met Lys Ser His Asp Gly Gly Gly Gly Ser
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Flexible linker

<400> SEQUENCE: 36

Gly Gly Gly Gly Asn Leu Ile Thr Ile Val Gly Gly Gly Gly Ser
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Flexible linker

<400> SEQUENCE: 37

Gly Gly Gly Gly Val Val Pro Ser Leu Pro Gly Gly Gly Gly Ser
1               5                   10                  15

<210> SEQ ID NO 38
<211> LENGTH: 12
<212> TYPE: PRT
<213> ORGANISM: Artificial Sequence
<220> FEATURE:
<223> OTHER INFORMATION: Flexible linker
```

```
<400> SEQUENCE: 38

Gly Gly Glu Lys Ser Ile Pro Gly Gly Gly Ser
1               5                   10

<210> SEQ ID NO 39
<211> LENGTH: 18
<212> TYPE: PRT
<213> ORGANISM: Artificial Sequence
<220> FEATURE:
<223> OTHER INFORMATION: Flexible linker

<400> SEQUENCE: 39

Arg Pro Leu Ser Tyr Arg Pro Pro Phe Pro Phe Gly Phe Pro Ser Val
1               5                   10                  15

Arg Pro

<210> SEQ ID NO 40
<211> LENGTH: 18
<212> TYPE: PRT
<213> ORGANISM: Artificial Sequence
<220> FEATURE:
<223> OTHER INFORMATION: Flexible linker

<400> SEQUENCE: 40

Tyr Pro Arg Ser Ile Tyr Ile Arg Arg His Pro Ser Pro Ser Leu
1               5                   10                  15

Thr Thr

<210> SEQ ID NO 41
<211> LENGTH: 18
<212> TYPE: PRT
<213> ORGANISM: Artificial Sequence
<220> FEATURE:
<223> OTHER INFORMATION: Flexible linker

<400> SEQUENCE: 41

Thr Pro Ser His Leu Ser His Ile Leu Pro Ser Phe Gly Leu Pro Thr
1               5                   10                  15

Phe Asn

<210> SEQ ID NO 42
<211> LENGTH: 18
<212> TYPE: PRT
<213> ORGANISM: Artificial Sequence
<220> FEATURE:
<223> OTHER INFORMATION: Flexible linker

<400> SEQUENCE: 42

Arg Pro Val Ser Pro Phe Thr Phe Pro Arg Leu Ser Asn Ser Trp Leu
1               5                   10                  15

Pro Ala

<210> SEQ ID NO 43
<211> LENGTH: 18
<212> TYPE: PRT
<213> ORGANISM: Artificial Sequence
<220> FEATURE:
<223> OTHER INFORMATION: Flexible linker

<400> SEQUENCE: 43

Ser Pro Ala Ala His Phe Pro Arg Ser Ile Pro Arg Pro Gly Pro Ile
1               5                   10                  15
```

Arg Thr

<210> SEQ ID NO 44
<211> LENGTH: 18
<212> TYPE: PRT
<213> ORGANISM: Artificial Sequence
<220> FEATURE:
<223> OTHER INFORMATION: Flexible linker

<400> SEQUENCE: 44

Ala Pro Gly Pro Ser Ala Pro Ser His Arg Ser Leu Pro Ser Arg Ala
1               5                   10                  15

Phe Gly

<210> SEQ ID NO 45
<211> LENGTH: 18
<212> TYPE: PRT
<213> ORGANISM: Artificial Sequence
<220> FEATURE:
<223> OTHER INFORMATION: Flexible linker

<400> SEQUENCE: 45

Pro Arg Asn Ser Ile His Phe Leu His Pro Leu Leu Val Ala Pro Leu
1               5                   10                  15

Gly Ala

<210> SEQ ID NO 46
<211> LENGTH: 18
<212> TYPE: PRT
<213> ORGANISM: Artificial Sequence
<220> FEATURE:
<223> OTHER INFORMATION: Flexible linker

<400> SEQUENCE: 46

Met Pro Ser Leu Ser Gly Val Leu Gln Val Arg Tyr Leu Ser Pro Pro
1               5                   10                  15

Asp Leu

<210> SEQ ID NO 47
<211> LENGTH: 18
<212> TYPE: PRT
<213> ORGANISM: Artificial Sequence
<220> FEATURE:
<223> OTHER INFORMATION: Flexible linker

<400> SEQUENCE: 47

Ser Pro Gln Tyr Pro Ser Pro Leu Thr Leu Thr Leu Pro Pro His Pro
1               5                   10                  15

Ser Leu

<210> SEQ ID NO 48
<211> LENGTH: 18
<212> TYPE: PRT
<213> ORGANISM: Artificial Sequence
<220> FEATURE:
<223> OTHER INFORMATION: Flexible linker

<400> SEQUENCE: 48

Asn Pro Ser Leu Asn Pro Pro Ser Tyr Leu His Arg Ala Pro Ser Arg
1               5                   10                  15

Ile Ser

<210> SEQ ID NO 49

```
<211> LENGTH: 17
<212> TYPE: PRT
<213> ORGANISM: Artificial Sequence
<220> FEATURE:
<223> OTHER INFORMATION: Flexible linker

<400> SEQUENCE: 49

Leu Pro Trp Arg Thr Ser Leu Leu Pro Ser Leu Pro Leu Arg Arg Arg
1               5                   10                  15

Pro

<210> SEQ ID NO 50
<211> LENGTH: 18
<212> TYPE: PRT
<213> ORGANISM: Artificial Sequence
<220> FEATURE:
<223> OTHER INFORMATION: Flexible linker

<400> SEQUENCE: 50

Pro Pro Leu Phe Ala Lys Gly Pro Val Gly Leu Leu Ser Arg Ser Phe
1               5                   10                  15

Pro Pro

<210> SEQ ID NO 51
<211> LENGTH: 18
<212> TYPE: PRT
<213> ORGANISM: Artificial Sequence
<220> FEATURE:
<223> OTHER INFORMATION: Flexible linker

<400> SEQUENCE: 51

Val Pro Pro Ala Pro Val Val Ser Leu Arg Ser Ala His Ala Arg Pro
1               5                   10                  15

Pro Tyr

<210> SEQ ID NO 52
<211> LENGTH: 17
<212> TYPE: PRT
<213> ORGANISM: Artificial Sequence
<220> FEATURE:
<223> OTHER INFORMATION: Flexible linker

<400> SEQUENCE: 52

Leu Arg Pro Thr Pro Pro Arg Val Arg Ser Tyr Thr Cys Cys Pro Thr
1               5                   10                  15

Pro

<210> SEQ ID NO 53
<211> LENGTH: 18
<212> TYPE: PRT
<213> ORGANISM: Artificial Sequence
<220> FEATURE:
<223> OTHER INFORMATION: Flexible linker

<400> SEQUENCE: 53

Pro Asn Val Ala His Val Leu Pro Leu Leu Thr Val Pro Trp Asp Asn
1               5                   10                  15

Leu Arg

<210> SEQ ID NO 54
<211> LENGTH: 18
<212> TYPE: PRT
<213> ORGANISM: Artificial Sequence
<220> FEATURE:
```

<223> OTHER INFORMATION: Flexible linker

<400> SEQUENCE: 54

Cys Asn Pro Leu Leu Pro Leu Cys Ala Arg Ser Pro Ala Val Arg Thr
1               5                   10                  15
Phe Pro

<210> SEQ ID NO 55
<211> LENGTH: 11
<212> TYPE: PRT
<213> ORGANISM: Artificial Sequence
<220> FEATURE:
<223> OTHER INFORMATION: Linker

<400> SEQUENCE: 55

Asp Leu Cys Leu Arg Asp Trp Gly Cys Leu Trp
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Linker

<400> SEQUENCE: 56

Asp Ile Cys Leu Pro Arg Trp Gly Cys Leu Trp
1               5                   10

<210> SEQ ID NO 57
<211> LENGTH: 15
<212> TYPE: PRT
<213> ORGANISM: Artificial Sequence
<220> FEATURE:
<223> OTHER INFORMATION: Linker

<400> SEQUENCE: 57

Met Glu Asp Ile Cys Leu Pro Arg Trp Gly Cys Leu Trp Gly Asp
1               5                   10                  15

<210> SEQ ID NO 58
<211> LENGTH: 20
<212> TYPE: PRT
<213> ORGANISM: Artificial Sequence
<220> FEATURE:
<223> OTHER INFORMATION: Linker

<400> SEQUENCE: 58

Gln Arg Leu Met Glu Asp Ile Cys Leu Pro Arg Trp Gly Cys Leu Trp
1               5                   10                  15
Glu Asp Asp Glu
            20

<210> SEQ ID NO 59
<211> LENGTH: 20
<212> TYPE: PRT
<213> ORGANISM: Artificial Sequence
<220> FEATURE:
<223> OTHER INFORMATION: Linker

<400> SEQUENCE: 59

Gln Gly Leu Ile Gly Asp Ile Cys Leu Pro Arg Trp Gly Cys Leu Trp
1               5                   10                  15
Gly Arg Ser Val
            20

```
<210> SEQ ID NO 60
<211> LENGTH: 21
<212> TYPE: PRT
<213> ORGANISM: Artificial Sequence
<220> FEATURE:
<223> OTHER INFORMATION: Linker

<400> SEQUENCE: 60

Gln Gly Leu Ile Gly Asp Ile Cys Leu Pro Arg Trp Gly Cys Leu Trp
1               5                   10                  15

Gly Arg Ser Val Lys
            20

<210> SEQ ID NO 61
<211> LENGTH: 15
<212> TYPE: PRT
<213> ORGANISM: Artificial Sequence
<220> FEATURE:
<223> OTHER INFORMATION: Linker

<400> SEQUENCE: 61

Glu Asp Ile Cys Leu Pro Arg Trp Gly Cys Leu Trp Glu Asp Asp
1               5                   10                  15

<210> SEQ ID NO 62
<211> LENGTH: 18
<212> TYPE: PRT
<213> ORGANISM: Artificial Sequence
<220> FEATURE:
<223> OTHER INFORMATION: Linker

<400> SEQUENCE: 62

Arg Leu Met Glu Asp Ile Cys Leu Pro Arg Trp Gly Cys Leu Trp Glu
1               5                   10                  15

Asp Asp

<210> SEQ ID NO 63
<211> LENGTH: 16
<212> TYPE: PRT
<213> ORGANISM: Artificial Sequence
<220> FEATURE:
<223> OTHER INFORMATION: Linker

<400> SEQUENCE: 63

Met Glu Asp Ile Cys Leu Pro Arg Trp Gly Cys Leu Trp Glu Asp Asp
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: Linker

<400> SEQUENCE: 64

Met Glu Asp Ile Cys Leu Pro Arg Trp Gly Cys Leu Trp Glu Asp
1               5                   10                  15

<210> SEQ ID NO 65
<211> LENGTH: 18
<212> TYPE: PRT
<213> ORGANISM: Artificial Sequence
<220> FEATURE:
<223> OTHER INFORMATION: Linker
```

```
<400> SEQUENCE: 65

Arg Leu Met Glu Asp Ile Cys Leu Ala Arg Trp Gly Cys Leu Trp Glu
1               5                   10                  15

Asp Asp

<210> SEQ ID NO 66
<211> LENGTH: 20
<212> TYPE: PRT
<213> ORGANISM: Artificial Sequence
<220> FEATURE:
<223> OTHER INFORMATION: Linker

<400> SEQUENCE: 66

Glu Val Arg Ser Phe Cys Thr Arg Trp Pro Ala Glu Lys Ser Cys Lys
1               5                   10                  15

Pro Leu Arg Gly
            20

<210> SEQ ID NO 67
<211> LENGTH: 20
<212> TYPE: PRT
<213> ORGANISM: Artificial Sequence
<220> FEATURE:
<223> OTHER INFORMATION: Linker

<400> SEQUENCE: 67

Arg Ala Pro Glu Ser Phe Val Cys Tyr Trp Glu Thr Ile Cys Phe Glu
1               5                   10                  15

Arg Ser Glu Gln
            20

<210> SEQ ID NO 68
<211> LENGTH: 11
<212> TYPE: PRT
<213> ORGANISM: Artificial Sequence
<220> FEATURE:
<223> OTHER INFORMATION: Linker

<400> SEQUENCE: 68

Glu Met Cys Tyr Phe Pro Gly Ile Cys Trp Met
1               5                   10

<210> SEQ ID NO 69
<211> LENGTH: 11
<212> TYPE: PRT
<213> ORGANISM: Artificial Sequence
<220> FEATURE:
<223> OTHER INFORMATION: peptide sequence

<400> SEQUENCE: 69

Gly Ala Pro Ala Pro Ala Ala Pro Ala Pro Ala
1               5                   10

<210> SEQ ID NO 70
<211> LENGTH: 4
<212> TYPE: PRT
<213> ORGANISM: Artificial Sequence
<220> FEATURE:
<223> OTHER INFORMATION: peptide sequence

<400> SEQUENCE: 70

Pro Pro Pro Pro
1
```

```
<210> SEQ ID NO 71
<211> LENGTH: 6
<212> TYPE: PRT
<213> ORGANISM: Artificial sequence
<220> FEATURE:
<223> OTHER INFORMATION: Linker

<400> SEQUENCE: 71

Ala Ser Gly Gly Gly Gly
1               5

<210> SEQ ID NO 72
<211> LENGTH: 8
<212> TYPE: PRT
<213> ORGANISM: Artificial Sequence
<220> FEATURE:
<223> OTHER INFORMATION: Linker

<400> SEQUENCE: 72

Ala Ser Gly Gly Gly Gly Ser Gly
1               5

<210> SEQ ID NO 73
<211> LENGTH: 5
<212> TYPE: PRT
<213> ORGANISM: Artificial Sequence
<220> FEATURE:
<223> OTHER INFORMATION: Linker

<400> SEQUENCE: 73

Ala Ser Gly Gly Gly
1               5

<210> SEQ ID NO 74
<211> LENGTH: 7
<212> TYPE: PRT
<213> ORGANISM: Artificial Sequence
<220> FEATURE:
<223> OTHER INFORMATION: Linker

<400> SEQUENCE: 74

Ala Ala Ala Ser Gly Gly Gly
1               5

<210> SEQ ID NO 75
<211> LENGTH: 43
<212> TYPE: PRT
<213> ORGANISM: Artificial Sequence
<220> FEATURE:
<223> OTHER INFORMATION: GCN4 peptide variant

<400> SEQUENCE: 75

Gly Gly Gly Gly Ser Gly Gly Gly Ser Gly Gly Gly Ser Gly
1               5                   10                  15

Gly Gly Ser Tyr His Leu Glu Asn Glu Val Ala Arg Leu Lys Lys
            20                  25                  30

Leu Val Gly Glu Arg His His His His His His
        35                  40

<210> SEQ ID NO 76
<211> LENGTH: 43
<212> TYPE: PRT
<213> ORGANISM: artificial sequence
<220> FEATURE:
<223> OTHER INFORMATION: GCN4 peptide variant

<400> SEQUENCE: 76
```

Gly Gly Gly Gly Ser Gly Gly Gly Gly Ser Gly Gly Gly Ser Gly
1               5                   10                  15

Gly Gly Gly Ser Tyr His Leu Glu Asn Glu Val Ala Arg Leu Lys Ala
            20                  25                  30

Leu Val Gly Glu Arg His His His His His His
        35                  40

<210> SEQ ID NO 77
<211> LENGTH: 43
<212> TYPE: PRT
<213> ORGANISM: Artificial Sequence
<220> FEATURE:
<223> OTHER INFORMATION: GCN4 peptide variant

<400> SEQUENCE: 77

Gly Gly Gly Gly Ser Gly Gly Gly Gly Ser Gly Gly Gly Ser Gly
1               5                   10                  15

Gly Gly Gly Ser Tyr His Leu Glu Asn Glu Val Ala Arg Leu Ala Lys
            20                  25                  30

Leu Val Gly Glu Arg His His His His His His
        35                  40

<210> SEQ ID NO 78
<211> LENGTH: 43
<212> TYPE: PRT
<213> ORGANISM: Artificial Sequence
<220> FEATURE:
<223> OTHER INFORMATION: GCN4 peptide variant

<400> SEQUENCE: 78

Gly Gly Gly Gly Ser Gly Gly Gly Gly Ser Gly Gly Gly Ser Gly
1               5                   10                  15

Gly Gly Gly Ser Tyr His Leu Glu Asn Glu Val Ala Arg Leu Gln Lys
            20                  25                  30

Leu Val Gly Glu Arg His His His His His His
        35                  40

<210> SEQ ID NO 79
<211> LENGTH: 43
<212> TYPE: PRT
<213> ORGANISM: Artificial Sequence
<220> FEATURE:
<223> OTHER INFORMATION: GCN4 peptide variant

<400> SEQUENCE: 79

Gly Gly Gly Gly Ser Gly Gly Gly Gly Ser Gly Gly Gly Ser Gly
1               5                   10                  15

Gly Gly Gly Ser Tyr His Leu Glu Asn Glu Val Ala Arg Leu Asn Lys
            20                  25                  30

Leu Val Gly Glu Arg His His His His His His
        35                  40

<210> SEQ ID NO 80
<211> LENGTH: 43
<212> TYPE: PRT
<213> ORGANISM: Artificial Sequence
<220> FEATURE:
<223> OTHER INFORMATION: GCN4 peptide variant

<400> SEQUENCE: 80

Gly Gly Gly Gly Ser Gly Gly Gly Gly Ser Gly Gly Gly Ser Gly
1               5                   10                  15

-continued

Gly Gly Gly Ser Tyr His Leu Glu Asn Glu Val Ala Arg Leu Ala Ala
                20                  25                  30

Leu Val Gly Glu Arg His His His His His
            35                  40

<210> SEQ ID NO 81
<211> LENGTH: 43
<212> TYPE: PRT
<213> ORGANISM: Artificial Sequence
<220> FEATURE:
<223> OTHER INFORMATION: GCN4 peptide variant

<400> SEQUENCE: 81

Gly Gly Gly Gly Ser Gly Gly Gly Ser Gly Gly Gly Gly Ser Gly
1               5                   10                  15

Gly Gly Gly Ser Tyr His Leu Glu Asn Glu Val Ala Arg Leu Gln Ala
                20                  25                  30

Leu Val Gly Glu Arg His His His His His
            35                  40

<210> SEQ ID NO 82
<211> LENGTH: 43
<212> TYPE: PRT
<213> ORGANISM: Artificial Sequence
<220> FEATURE:
<223> OTHER INFORMATION: GCN4 peptide variant

<400> SEQUENCE: 82

Gly Gly Gly Gly Ser Gly Gly Gly Ser Gly Gly Gly Gly Ser Gly
1               5                   10                  15

Gly Gly Gly Ser Tyr His Leu Glu Asn Glu Val Ala Arg Leu Asn Ala
                20                  25                  30

Leu Val Gly Glu Arg His His His His His
            35                  40

<210> SEQ ID NO 83
<211> LENGTH: 44
<212> TYPE: PRT
<213> ORGANISM: Artificial Sequence
<220> FEATURE:
<223> OTHER INFORMATION: GCN4 peptide variant

<400> SEQUENCE: 83

Ala Ser Gly Gly Gly Ala Met Lys Gln Leu Glu Pro Lys Val Glu Glu
1               5                   10                  15

Leu Leu Pro Lys Asn Tyr His Leu Glu Asn Glu Val Ala Arg Leu Lys
                20                  25                  30

Lys Leu Val Gly Glu Arg His His His His His
            35                  40

<210> SEQ ID NO 84
<211> LENGTH: 44
<212> TYPE: PRT
<213> ORGANISM: Artificial Sequence
<220> FEATURE:
<223> OTHER INFORMATION: GCN4 peptide variant

<400> SEQUENCE: 84

Ala Ser Gly Gly Gly Arg Met Lys Gln Leu Glu Pro Lys Val Glu Glu
1               5                   10                  15

Leu Leu Pro Lys Asn Tyr His Leu Glu Asn Glu Val Ala Arg Leu Lys
                20                  25                  30

Ala Leu Val Gly Glu Arg His His His His His
        35                  40

<210> SEQ ID NO 85
<211> LENGTH: 44
<212> TYPE: PRT
<213> ORGANISM: Artificial Sequence
<220> FEATURE:
<223> OTHER INFORMATION: GCN4 peptide variant

<400> SEQUENCE: 85

Ala Ser Gly Gly Gly Ala Met Lys Gln Leu Glu Pro Lys Val Glu Glu
1               5                   10                  15

Leu Leu Pro Lys Asn Tyr His Leu Glu Asn Glu Val Ala Arg Leu Lys
            20                  25                  30

Ala Leu Val Gly Glu Arg His His His His His His
        35                  40

<210> SEQ ID NO 86
<211> LENGTH: 44
<212> TYPE: PRT
<213> ORGANISM: Artificial Sequence
<220> FEATURE:
<223> OTHER INFORMATION: GCN4 peptide variant

<400> SEQUENCE: 86

Ala Ser Gly Gly Gly Arg Met Lys Gln Leu Glu Pro Lys Val Glu Glu
1               5                   10                  15

Leu Leu Pro Lys Asn Tyr His Leu Glu Asn Glu Val Ala Arg Leu Ala
            20                  25                  30

Lys Leu Val Gly Glu Arg His His His His His His
        35                  40

<210> SEQ ID NO 87
<211> LENGTH: 44
<212> TYPE: PRT
<213> ORGANISM: Artificial Sequence
<220> FEATURE:
<223> OTHER INFORMATION: GCN4 peptide variant

<400> SEQUENCE: 87

Ala Ser Gly Gly Gly Arg Met Lys Gln Leu Glu Pro Lys Val Glu Glu
1               5                   10                  15

Leu Leu Pro Lys Asn Tyr His Leu Glu Asn Glu Val Ala Arg Leu Gln
            20                  25                  30

Lys Leu Val Gly Glu Arg His His His His His His
        35                  40

<210> SEQ ID NO 88
<211> LENGTH: 44
<212> TYPE: PRT
<213> ORGANISM: Artificial Sequence
<220> FEATURE:
<223> OTHER INFORMATION: GCN4 peptide variant

<400> SEQUENCE: 88

Ala Ser Gly Gly Gly Arg Met Lys Gln Leu Glu Pro Lys Val Glu Glu
1               5                   10                  15

Leu Leu Pro Lys Asn Tyr His Leu Glu Asn Glu Val Ala Arg Leu Asn
            20                  25                  30

Lys Leu Val Gly Glu Arg His His His His His His
        35                  40

<210> SEQ ID NO 89
<211> LENGTH: 44
<212> TYPE: PRT
<213> ORGANISM: Artificial Sequence
<220> FEATURE:
<223> OTHER INFORMATION: GCN4 peptide variant

<400> SEQUENCE: 89

Ala Ser Gly Gly Gly Ala Met Lys Gln Leu Glu Pro Lys Val Glu Glu
1               5                   10                  15

Leu Leu Pro Lys Asn Tyr His Leu Glu Asn Glu Val Ala Arg Leu Ala
            20                  25                  30

Lys Leu Val Gly Glu Arg His His His His His His
        35                  40

<210> SEQ ID NO 90
<211> LENGTH: 44
<212> TYPE: PRT
<213> ORGANISM: Artificial Sequence
<220> FEATURE:
<223> OTHER INFORMATION: GCN4 peptide variant

<400> SEQUENCE: 90

Ala Ser Gly Gly Gly Ala Met Lys Gln Leu Glu Pro Lys Val Glu Glu
1               5                   10                  15

Leu Leu Pro Lys Asn Tyr His Leu Glu Asn Glu Val Ala Arg Leu Gln
            20                  25                  30

Lys Leu Val Gly Glu Arg His His His His His His
        35                  40

<210> SEQ ID NO 91
<211> LENGTH: 44
<212> TYPE: PRT
<213> ORGANISM: Artificial Sequence
<220> FEATURE:
<223> OTHER INFORMATION: GCN4 peptide variant

<400> SEQUENCE: 91

Ala Ser Gly Gly Gly Ala Met Lys Gln Leu Glu Pro Lys Val Glu Glu
1               5                   10                  15

Leu Leu Pro Lys Asn Tyr His Leu Glu Asn Glu Val Ala Arg Leu Asn
            20                  25                  30

Lys Leu Val Gly Glu Arg His His His His His His
        35                  40

<210> SEQ ID NO 92
<211> LENGTH: 44
<212> TYPE: PRT
<213> ORGANISM: Artificial Sequence
<220> FEATURE:
<223> OTHER INFORMATION: GCN4 peptide variant

<400> SEQUENCE: 92

Ala Ser Gly Gly Gly Arg Met Lys Gln Leu Glu Pro Lys Val Glu Glu
1               5                   10                  15

Leu Leu Pro Lys Asn Tyr His Leu Glu Asn Glu Val Ala Arg Leu Ala
            20                  25                  30

Ala Leu Val Gly Glu Arg His His His His His His
        35                  40

<210> SEQ ID NO 93

<211> LENGTH: 44
<212> TYPE: PRT
<213> ORGANISM: Artificial Sequence
<220> FEATURE:
<223> OTHER INFORMATION: GCN4 peptide variant

<400> SEQUENCE: 93

Ala Ser Gly Gly Gly Arg Met Lys Gln Leu Glu Pro Lys Val Glu Glu
1               5                   10                  15

Leu Leu Pro Lys Asn Tyr His Leu Glu Asn Glu Val Ala Arg Leu Gln
            20                  25                  30

Ala Leu Val Gly Glu Arg His His His His His His
        35                  40

<210> SEQ ID NO 94
<211> LENGTH: 44
<212> TYPE: PRT
<213> ORGANISM: Artificial Sequence
<220> FEATURE:
<223> OTHER INFORMATION: GCN4 peptide variant

<400> SEQUENCE: 94

Ala Ser Gly Gly Gly Arg Met Lys Gln Leu Glu Pro Lys Val Glu Glu
1               5                   10                  15

Leu Leu Pro Lys Asn Tyr His Leu Glu Asn Glu Val Ala Arg Leu Asn
            20                  25                  30

Ala Leu Val Gly Glu Arg His His His His His His
        35                  40

<210> SEQ ID NO 95
<211> LENGTH: 44
<212> TYPE: PRT
<213> ORGANISM: Artificial Sequence
<220> FEATURE:
<223> OTHER INFORMATION: GCN4 peptide variant

<400> SEQUENCE: 95

Ala Ser Gly Gly Gly Ala Met Lys Gln Leu Glu Pro Lys Val Glu Glu
1               5                   10                  15

Leu Leu Pro Lys Asn Tyr His Leu Glu Asn Glu Val Ala Arg Leu Ala
            20                  25                  30

Ala Leu Val Gly Glu Arg His His His His His His
        35                  40

<210> SEQ ID NO 96
<211> LENGTH: 44
<212> TYPE: PRT
<213> ORGANISM: Artificial Sequence
<220> FEATURE:
<223> OTHER INFORMATION: GCN4 peptide variant

<400> SEQUENCE: 96

Ala Ser Gly Gly Gly Ala Met Lys Gln Leu Glu Pro Lys Val Glu Glu
1               5                   10                  15

Leu Leu Pro Lys Asn Tyr His Leu Glu Asn Glu Val Ala Arg Leu Gln
            20                  25                  30

Ala Leu Val Gly Glu Arg His His His His His His
        35                  40

<210> SEQ ID NO 97
<211> LENGTH: 44
<212> TYPE: PRT
<213> ORGANISM: Artificial Sequence
<220> FEATURE:
<223> OTHER INFORMATION: GCN4 peptide variant

<400> SEQUENCE: 97

Ala Ser Gly Gly Gly Ala Met Lys Gln Leu Glu Pro Lys Val Glu Glu
1               5                   10                  15

Leu Leu Pro Lys Asn Tyr His Leu Glu Asn Glu Val Ala Arg Leu Asn
                20                  25                  30

Ala Leu Val Gly Glu Arg His His His His His His
            35                  40

<210> SEQ ID NO 98
<211> LENGTH: 243
<212> TYPE: PRT
<213> ORGANISM: Artificial Sequence
<220> FEATURE:
<223> OTHER INFORMATION: 52SR4 scFV variant

<400> SEQUENCE: 98

Asp Ala Val Val Thr Gln Glu Ser Ala Leu Thr Ser Ser Pro Gly Glu
1               5                   10                  15

Thr Val Thr Leu Thr Cys Arg Ser Ser Thr Gly Ala Val Thr Thr Ser
                20                  25                  30

Asn Tyr Ala Ser Trp Val Gln Glu Lys Pro Asp His Leu Phe Thr Gly
            35                  40                  45

Leu Ile Gly Gly Thr Asn Asn Arg Ala Pro Gly Val Pro Ala Arg Phe
        50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Val Leu Trp Tyr Ser Asp
                85                  90                  95

His Trp Val Phe Gly Cys Gly Thr Lys Leu Thr Val Leu Gly Gly Gly
            100                 105                 110

Gly Gly Ser Gly Gly Gly Gly Ser Gly Gly Gly Ser Gly Gly Gly Gly
        115                 120                 125

Gly Ser Asp Val Gln Leu Gln Gln Ser Gly Pro Gly Leu Val Ala Pro
130                 135                 140

Ser Gln Ser Leu Ser Ile Thr Cys Thr Val Ser Gly Phe Leu Leu Thr
145                 150                 155                 160

Asp Tyr Gly Val Asn Trp Val Arg Gln Ser Pro Gly Lys Cys Leu Glu
                165                 170                 175

Trp Leu Gly Val Ile Trp Gly Asp Gly Ile Thr Asp Tyr Asn Ser Ala
            180                 185                 190

Leu Lys Ser Arg Leu Ser Val Thr Lys Asp Asn Ser Lys Ser Gln Val
        195                 200                 205

Phe Leu Lys Met Asn Ser Leu Gln Ser Gly Asp Ser Ala Arg Tyr Tyr
    210                 215                 220

Cys Val Thr Gly Leu Phe Asp Tyr Trp Gly Gln Gly Thr Thr Leu Thr
225                 230                 235                 240

Val Ser Ser

<210> SEQ ID NO 99
<211> LENGTH: 292
<212> TYPE: PRT
<213> ORGANISM: Artificial Sequence
<220> FEATURE:
<223> OTHER INFORMATION: 52SR4 scFv variant

<400> SEQUENCE: 99

Asp Val Gln Leu Gln Gln Ser Gly Pro Gly Leu Val Ala Pro Ser Gln
1               5                   10                  15

Ser Leu Ser Ile Thr Cys Thr Val Ser Gly Phe Leu Leu Thr Asp Tyr
            20                  25                  30

Gly Val Asn Trp Val Arg Gln Ser Pro Gly Lys Cys Leu Glu Trp Leu
        35                  40                  45

Gly Val Ile Trp Gly Asp Gly Ile Thr Asp Tyr Asn Ser Ala Leu Lys
    50                  55                  60

Ser Arg Leu Ser Val Thr Lys Asp Asn Ser Lys Ser Gln Val Phe Leu
65                  70                  75                  80

Lys Met Asn Ser Leu Gln Ser Gly Asp Ser Ala Arg Tyr Tyr Cys Val
                85                  90                  95

Thr Gly Leu Phe Asp Tyr Trp Gly Gln Gly Thr Thr Leu Thr Val Ser
            100                 105                 110

Ser Pro Ala Arg Phe Ser Gly Ser Leu Ile Gly Asp Lys Ala Ala Leu
        115                 120                 125

Thr Ile Thr Gly Ala Gln Thr Glu Asp Glu Ala Ile Tyr Phe Cys Val
    130                 135                 140

Leu Trp Tyr Ser Asp His Trp Val Phe Gly Cys Gly Thr Lys Leu Thr
145                 150                 155                 160

Val Leu Gly Gly Gly Gly Ser Gly Gly Gly Ser Gly Gly
                165                 170                 175

Gly Ser Gly Gly Gly Ser Asp Ala Val Val Thr Gln Glu Ser Ala
            180                 185                 190

Leu Thr Ser Ser Pro Gly Glu Thr Val Thr Leu Thr Cys Arg Ser Ser
        195                 200                 205

Thr Gly Ala Val Thr Thr Ser Asn Tyr Ala Ser Trp Val Gln Glu Lys
    210                 215                 220

Pro Asp His Leu Phe Thr Gly Leu Ile Gly Gly Thr Asn Asn Arg Ala
225                 230                 235                 240

Pro Gly Val Pro Ala Arg Phe Ser Gly Ser Leu Ile Gly Asp Lys Ala
                245                 250                 255

Ala Leu Thr Ile Thr Gly Ala Gln Thr Glu Asp Glu Ala Ile Tyr Phe
            260                 265                 270

Cys Val Leu Trp Tyr Ser Asp His Trp Val Phe Gly Cys Gly Thr Lys
        275                 280                 285

Leu Thr Val Leu
    290

<210> SEQ ID NO 100
<211> LENGTH: 20
<212> TYPE: PRT
<213> ORGANISM: Artificial Sequence
<220> FEATURE:
<223> OTHER INFORMATION: signal sequence

<400> SEQUENCE: 100

Met Ser Val Pro Thr Gln Val Leu Gly Leu Leu Leu Leu Trp Leu Thr
1               5                   10                  15

Asp Ala Arg Cys
            20

<210> SEQ ID NO 101
<211> LENGTH: 19
<212> TYPE: PRT

```
<213> ORGANISM: Artificial Sequence
<220> FEATURE:
<223> OTHER INFORMATION: signal sequence

<400> SEQUENCE: 101

Met Glu Trp Ser Trp Val Phe Leu Phe Leu Ser Val Thr Thr Gly
1               5                   10                  15

Val His Ser

<210> SEQ ID NO 102
<211> LENGTH: 19
<212> TYPE: PRT
<213> ORGANISM: Artificial Sequence
<220> FEATURE:
<223> OTHER INFORMATION: signal sequence

<400> SEQUENCE: 102

Met Asp Trp Leu Trp Thr Leu Leu Phe Leu Met Ala Ala Gln Ser
1               5                   10                  15

Ala Gln Ala

<210> SEQ ID NO 103
<211> LENGTH: 19
<212> TYPE: PRT
<213> ORGANISM: Artificial Sequence
<220> FEATURE:
<223> OTHER INFORMATION: signal sequence

<400> SEQUENCE: 103

Met Gly Trp Ser Trp Thr Phe Leu Phe Leu Leu Ser Gly Thr Ser Gly
1               5                   10                  15

Val Leu Ser
```

MULTISPECIFIC ANTIBODIES

REFERENCE TO AN ELECTRONIC SEQUENCE LISTING

The contents of the electronic sequence listing (00890016US1seqlist.txt; Size: 38 KB; and Date of Creation May 22, 2018) is herein incorporated by reference in its entirety.

FIELD OF INVENTION

The present disclosure relates to a new multispecific protein complex format and a method, in particular an in vitro/ex vivo method, of detecting synergistic biological function in a heterodimerically-tethered multispecific protein complex, libraries/multiplexes of the multispecific protein complexes, and kits and compositions thereof. The disclosure further relates to use of the multispecific protein complex to capture soluble molecules secreted from a particular cell, use in therapy, use in research and experimental purposes (in particular in assays to characterise patient populations by identifying cell populations relevant to a pathology or prognosis). The present disclosure also extends to methods of preparing said multispecific complexes.

BACKGROUND OF INVENTION

Biological mechanisms in vivo are extremely complicated cascades of signals, which are difficult to deconvolute and understand. Activation of T cells requires at least two signals.

The recognition of the antigen by the T cell receptor is considered the first signal and the second signal arises from co-stimulation which results from the ligation of additional surface molecules on the T cell with additional molecules on an antigen presenting cell.

Thus T cell activation can be used to illustrate that the modulation of biological functions can require multiple signals. Other biological processes are equally complicated or more complicated. Whilst in vitro screening based on cells has and can assist with gaining insights into in vivo mechanisms the problem still arises of how to identify appropriate ligand pairs which modulate the biological function.

Bispecific antibodies are widely expected to play a major role in the next generation of biotherapeutics (D. Holmes, Nature Rev Drug Disc November 2011:10; 798). They have the potential to deliver superior, long term, broad efficacy in a greater proportion of patients. This can be achieved by either co-engaging different antigens simultaneously within a common disease pathway, thereby reducing redundancy; or by targeting antigens from independent pathways to provide an additive or synergistic effect.

Bispecific antibodies facilitate access to novel biology such as:
1) cross-linking receptors on a cell,
2) inducing cell mediated effects,
3) localizing a cytokine to a cell to regulate signaling or locally block cytokine function, 4) engaging multiple epitopes simultaneously to generate "new activity", increase function or specificity, which may not be exhibited by a single monoclonal antibody or indeed mixtures of un-linked antibodies ('poly-monoclonals').

Current strategies to engage dual targets are largely based on rational design of known mechanisms and include: cross-linking inhibitory receptors, co-engagement/clustering of receptors, blocking multiple stimulatory pathways, selective engagement of inhibitory receptors and blocking distinct pathways such as co-stimulation & cytokine signaling. However, the current state of the art in relation to known mechanisms and targets is a limiting factor to progress in this area.

Whilst bispecific antibodies have enormous potential as biological therapeutics they also present an increased set of challenges within discovery and development compared to monoclonal antibodies. Two key areas of difficulty are, 1) the development of a successful bispecific antibody format, and 2) selecting the pairs of targets to which the bispecific antibody will crosslink or co-engage.

Many promising bispecific antibody formats have now been developed that could potentially work as successful therapeutics including DVD-Ig (Abbvie), DuoBodies (Genmab), Knobs-in-Holes (Genentech), Common light chain (Merus). However, in each of these cases these formats are not ideally suited to high throughput target-dual-antigen discovery screening to enable the discovery of novel antigen pairs for crosslinking with bispecific antibodies.

Typically for a single bispecific antibody construct at least two variable regions need to be sub-cloned from the original source of discovery vectors (e.g. phage display, hybridoma or single B-cell cloning) into appropriate bispecific expression vectors, each arm of the bispecific has to be expressed and the resulting bispecific antibody purified. This cloning and subsequent expression effort quickly becomes a significant practical bottleneck if large numbers of pairs of variable regions are to be combined in an attempt to screen for the most efficacious combination of discovered variable regions or to discover novel antigen pairs.

For example, if 50 unique antibodies are discovered against a panel of 50 cell surface targets, then a total of 2500 bispecific antibodies could potentially be generated (envisaged as an X-by-Y grid). With the bispecific antibody formats described above this would require at least 100 individual cloning reactions (50-X and 50-Y) followed by 2500 antibody expression experiments. Increasing the number of starting monoclonal antibodies to 100 would increase the minimal number of cloning reactions to 200 (100-X and 100-Y) and the expression number to 10,000.

Generally the root cause of this 'expression bottleneck' is the fact that the formats described above require both protein chain 'halves' of the final bispecific construct to be expressed simultaneously within a single expression experiment in the same cell. Therefore, for many formats, to produce 2500 bispecific antibodies, 2500 expression experiments are required. The 'expression bottleneck' is further exacerbated if the bispecific antibody format is monocistronic (i.e. cloned and expressed as a single chain protein), for example single chain diabodies, as the number of cloning experiments would be 2500 and 10,000 respectively for the numbers given above.

Furthermore after expression, extensive purification may be required to isolate the desired construct.

Some bispecific approaches employ a common light chain in the bispecific constructs in order to reduce the amount of cloning, although this doesn't reduce the number of expression experiments. Furthermore, using a common chain, such as a common light chain, makes the challenge of antibody discovery harder as it is more difficult to find the starting antibody variable domains as the antibody needs to bind its antigen with a high enough affinity through one chain, such as the heavy chain, alone.

Accordingly the use of current bispecific formats in large scale and high throughput screening to identify novel antigen pairs is impractical and has led to the continued use of solely hypothesis driven approaches to bispecific antigen targeting.

We propose that rather than designing and testing a limited selection of bispecific antibodies that engage given epitopes on two known targets, the true potential of exploiting access to novel biology with bispecific antibodies can only be achieved through a broad functional screening effort with a large, diverse combinatorial panel of bispecific antibodies or protein ligands. To facilitate this screening a format and a method is required that enables the generation of large numbers of diverse bispecific proteins which can be readily constructed and screened for functional effects in a variety of functional screens. This approach allows for the serendipitous identification of synergistic pairs.

Thus it would be useful to generate and screen a large number of multispecific protein complexes present as combinations of various antigen specificities. In particular, it would be useful to be able to generate and screen a large number of different multispecific antibody complexes in a quick and efficient manner. There are a range of existing methods for manufacturing multispecific antibodies as already described above. However, each of these methods has its disadvantages, as do alternative methods as further described in more detail below.

The problem of how to efficiently identify targets for bispecific and multispecific constructs has not been adequately addressed in the art. For example, WO2014/001326 employs chemical conjugation of a protein to a DNA fragment, wherein the DNA fragment hybridises to a complementary DNA sequence that links two such proteins together for generating tailor-made patient-specific multispecific molecules comprising at least two targeting entities. There are number of difficulties associated with this approach if it were to be applied to identifying new multispecific combinations, for example conjugation of the protein to the DNA can result in damage to the activity and/or structure of the protein. In particular protein-DNA hybrids are not naturally occurring thus there is a potential for interference. In addition the chemical conjugation required for joining the protein and DNA adds complexity, time and expense to the process.

Coupling and conjugation techniques exist for generating antibody drug conjugates and in vivo targeting technologies. Traditional chemical cross-linking is labour intensive as the relevant species may need to be purified from homodimers and other undesirable by-products. In addition, the chemical modification steps can alter the integrity of the proteins, thus leading to poor stability or altered biological function. As a result, the production of bispecific antibodies by chemical cross-linking is often inefficient and can also lead to a loss of antibody activity.

Another method of manufacturing bispecific antibodies is by cell-fusion (e.g. hybrid hybridomas), wherein the engineered cells express two heavy and two light antibody chains that assemble randomly. Since there are 4 possible variants to choose from, this results in the generation of 10 possible bispecific antibody combinations, of which only some (in many cases, only one) combinations would be desired. Hence, generating bispecific antibodies by cell-fusion results in low production yields and also requires an additional purification step in order to isolate the desired bispecific antibodies from the other bispecific antibodies produced. These disadvantages increase manufacturing time and costs.

Recombinant DNA techniques have also been employed for generating bispecific antibodies. For example, recombinant DNA techniques have also been used to generate 'knob into hole' bispecific antibodies. The 'knob into hole' technique involves engineering sterically complementary mutations in multimerization domains at the CH3 domain interface (see e.g., Ridgway et al., Protein Eng. 9:617-621 (1996); Merchant et al., Nat. Biotechnol. 16(7): 677-81 (1998); see also U.S. Pat. Nos. 5,731,168 and 7,183,076). One constraint of this strategy is that the light chains of the two parent antibodies have to be identical to prevent mispairing and formation of undesired and/or inactive molecules when expressed in the same cell. Each bispecific (heavy and light chains thereof) must be expressed in a single cell and the protein product generally contains about 20% of homodimer, which is subsequently removed by purification.

Other approaches are based on the natural exchange of chains in full-length IgG4 molecules (Genmab Duobody). The exchange is a dynamic process and this may lead to difficulties in relation to what the entity tested actually is.

Thus there is a need for new methods of generating multispecific protein complexes to enable the more efficient and higher throughput screening of multispecific antibodies. In particular, there is a need for a format and a method wherein a selection of any two antibodies or antibody fragments from a pool of available antibodies or antibody fragments can be readily combined to efficiently produce a multiplex of different multispecific antibodies, whilst, for example avoiding or minimising the formation of homodimers. Assembling different multispecific antibodies efficiently is particularly important when screening for synergistic biological function for new combinations of antigen specificities, in particular where heterodimers are essential for discovering that function.

SUMMARY OF INVENTION

In one aspect there is provided a new bispecific format particularly suitable for use in screening because all individual components can be expressed from a cell as individual units, essentially without aggregation and the units can be assembled simply by mixing without employing conjugation or coupling chemistry and with minimal homodimerisation.

Thus the present invention provides a multispecific protein complex having the formula $(A-X)_2:(Y-B)_2$ wherein:

A-X is a first fusion protein;
Y-B is a second fusion protein;
X:Y is a heterodimeric-tether;
: is a binding interaction between X and Y;
A is a first protein component of the multispecific protein complex which is one half of a full length antibody comprising a light chain (VLCL) paired with a full length heavy chain (VHCH1CH2CH3);
B is a second protein component of the multispecific protein complex selected from a Fab or Fab' fragment, a sdAb or a scFv;
X is a first binding partner of a binding pair selected from:
  i. an antigen, scFv or sdAb linked to A, optionally via a linker, and
  ii. an antigen, scFv or sdAb inserted between CH1 and CH2 of the heavy chain of A, optionally via a linker; and
Y is a second binding partner of the binding pair independently selected from an antigen, a Fab fragment, a Fab' fragment, a scFv and a sdAb linked to B such as the light chain or heavy chain of a Fab or Fab';

with the proviso that when X is an antigen Y is a Fab fragment, a Fab' fragment, a scFv or a sdAb specific to the antigen presented by X and when Y is an antigen X is a scFv or a sdAb specific to the antigen represented by Y.

Within the present disclosure, the fusion proteins' terms "A-X" and "Y-B" may be analogously indicated as "X-A" or "B-Y". The same applies to term for the heterodimeric-tether "X:Y" which can also be indicated herein as "Y:X". More specifically, X and Y may be fused to A and B, respectively, either at the N-terminal or at the C-terminal of A and B.

The multispecific protein complexes of the invention each comprise a full length antibody comprising two A-X units which dimerise to generate the full length antibody comprising an Fc domain. As such protein component A comprises one half of a full length antibody i.e. a light chain comprising both a variable (VL) and constant (CL) domain which is paired with a full length heavy chain which comprises a variable (VH) linked to a constant domain (CH1) which in turn is linked to two further constant domains (CH2CH3);

In one embodiment X is fused, optionally via a linker, to the C-terminal of the heavy chain of A i.e. the C-terminal of CH3.

In one embodiment X is fused, optionally via a linker, to the C-terminal of the light chain of A i.e. the C-terminal of CHL.

In one embodiment X is inserted, optionally via one or more linkers, between CH1 and CH2 of the heavy chain of A.

In one embodiment B is a Fab fragment.

In one embodiment B is a dsAb, such as a VHH or a scFv.

In one embodiment Y is fused, optionally via a linker, to the C-terminal of the heavy chain in the Fab or Fab' fragment (B), in particular Y is fused via a linker, to the C-terminal of the heavy chain in the Fab or Fab' fragment.

In one embodiment Y is fused, optionally via a linker, to the C-terminal of the light chain in the Fab or Fab' fragment (B), in particular Y is fused via a linker, to the C-terminal of the light chain in the Fab or Fab' fragment.

In one embodiment the variable X or Y is an antibody binding fragment such as a Fab fragment, a Fab' fragment, scFv, Fv, VH, VL or sdAb and the other variable is a peptide.

In one embodiment the variable X or Y is a Fab fragment, a Fab' fragment, a scFv, or sdAb and the other variable is a peptide, for example a Fab fragment, a Fab' fragment, a scFv, or sdAb specific to the peptide GCN4, a variant, a derivative or a fragment thereof (SEQ ID NO:1 or amino acids 1 to 38 of SEQ ID NO:1).

In one embodiment the variable X or Y is a scFv or sdAb and the other variable is a peptide, such as GCN4, a variant, a derivative or a fragment thereof (SEQ ID NO:1 or amino acids 1 to 38 of SEQ ID NO:1 in Table 1A, wherein the amino acids in bold are optional and the amino acids in italics are the sequence of the linker). In one embodiment X or Y is a scFv 52SR4 (SEQ ID NOs:3, 98 or 99 or amino acids 1 to 243 of SEQ ID NO:3). The nucleotide sequence encoding the GCN4 peptide according to SEQ ID NO: 1 is shown in SEQ ID NO: 1A as SEQ ID NO: 2.

TABLE 1A

| | |
|---|---|
| GCN4(7P14P) SEQ ID NO: 1 | *ASGGG*RMKQLEPKVEELLPKNYHLENEVARLKKLVGERHHHHHH |
| GCN4(7P14P) SEQ ID NO: 2 | GCTAGCGGAGGCGGAAGAATGAAACAACTTGAACCCAAGGTTGAAGAATTGCTT CCGAAAAATTATCACTTGGAAAATGAGGTTGCCAGATTAAAGAAATTAGTTGGC GAACGCCATCACCATCACCATCAC |
| 52SR4 ds scFv SEQ ID NO: 3 | DAVVTQESALTSSPGETVTLTCRSSTGAVTTSNYASWVQEKPDHLFTGLIGGTN NRAPGVPARFSGSLIGDKAALTITGAQTEDEAIYFCVLWYSDHWVFGCGTKLTV LGGGGGSGGGGSGGGGSGGGGSDVQLQQSGPGLVAPSQSLSITCTVSGFLLTDY GVNWVRQSPGKCLEWLGVIWGDGITDYNSALKSRLSVTKDNSKSQVFLKMNSLQ SGDSARYYCVTGLFDYWGQGTTLTVSSAAAHHHHHHEQKLISEEDL |
| 52SR4 ds scFv- SEQ ID NO: 4 | GATGCGGTGGTGACCCAGGAAAGCGCGCTGACCAGCAGCCCGGGCGAAACCGTG ACCCTGACCTGCCGCAGCAGCACCGGCGCGGTGACCACCAGCAACTATGCGAGC TGGGTGCAGGAAAAACCGGATCATCTGTTTACCGGCCTGATTGGCGGCACCAAC AACCGCGCGCCGGGCGTGCCGGCGCGCTTTAGCGGCAGCCTGATTGGCGATAAA GCGGCGCTGACCATTACCGGCGCGCAGACCGAAGATGAAGCGATTTATTTTTGC GTGCTGTGGTATAGCGACCATTGGGTGTTTGGCTGCGGCACCAAACTGACCGTG CTGGGTGGAGGCGGTGGCTCAGGCGGAGGTGGCTCAGGCGGTGGCGGGTCTGGC GGCGGCGGCAGCGATGTGCAGCTGCAGCAGAGCGGCCCGGGCCTGGTGGCGCCG AGCCAGAGCCTGAGCATTACCTGCACCGTGAGCGGCTTTCTCCTGACCGATTAT GGCGTGAACTGGGTGCGCCAGAGCCCGGGCAAATGCCTGGAATGGCTGGGCGTG ATTTGGGGCGATGGCATTACCGATTATAACAGCGCGCTGAAAAGCCGCCTGAGC GTGACCAAAGATAACAGCAAAAGCCAGGTGTTTCTGAAAATGAACAGCCTGCAG AGCGGCGATAGCGCGCGCTATTATTGCGTGACCGGCCTGTTTGATTATTGGGGC CAGGGCACCACCCTGACCGTGAGCAGCGCGGCCGCCCATCACCATCACCATCAC GAACAGAAACTGATTAGCGAAGAAGATCTGTAATAG |
| SEQ ID NO: 98 | DAVVTQESALTSSPGETVTLTCRSSTGAVTTSNYASWVQEKPDHLFTGLIGGTN NRAPGVPARFSGSLIGDKAALTITGAQTEDEAIYFCVLWYSDHWVFGCGTKLTV LGGGGGSGGGGSGGGGSGGGGSDVQLQQSGPGLVAPSQSLSITCTVSGFLLTDY GVNWVRQSPGKCLEWLGVIWGDGITDYNSALKSRLSVTKDNSKSQVFLKMNSLQ SGDSARYYCVTGLFDYWGQGTTLTVSS |
| SEQ ID NO: 99 | DVQLQQSGPGLVAPSQSLSITCTVSGFLLTDYGVNWVRQSPGKCLEWLGVIWGD GITDYNSALKSRLSVTKDNSKSQVFLKMNSLQSGDSARYYCVTGLFDYWGQGTT LTVSSPARFSGSLIGDKAALTITGAQTEDEAIYFCVLWYSDHWVFGCGTKLTVL GGGGSGGGGSGGGGSGGGGSDAVVTQESALTSSPGETVTLTCRSSTGAVTTSN YASWVQEKPDHLFTGLIGGTNNRAPGVPARFSGSLIGDKAALTITGAQTEDEAI YFCVLWYSDHWVFGCGTKLTVL |

TABLE 1A-continued

| SEQ ID NO: 100 | MSVPTQVLGLLLLWLTDARC |
| --- | --- |
| SEQ ID NO: 101 | MEWSWVFLFFLSVTTGVHS |
| SEQ ID NO: 102 | MDWLWTLLFLMAAAQSAQA |
| SEQ ID NO: 103 | MGWSWTFLFLLSGTSGVLS |

In one embodiment X is independently selected from an antigen, a scFv, a sdAb and a peptide, with the proviso that when X is a peptide or antigen, Y is an antibody or binding fragment thereof, such as a scFv, Fab or sdAb and when X is a scFv, Fab or sdAb then Y is an antigen or a peptide.

In one embodiment Y is independently selected from an antigen, a scFv, a sdAb, an antigen or a peptide, with the proviso that when Y is an antigen or a peptide X is an antibody or binding fragment, such as a scFv, Fab or sdAb and when Y is a scFv, Fab or a sdAb then X is an antigen, such as a peptide.

In one embodiment X or Y is a peptide GCN4, a variant, a derivative or a fragment thereof (SEQ ID NO:1 or amino acids 1 to 38 of SEQ ID NO:1), such as an epitope fragment thereof. In one embodiment X is a peptide, for example GCN4, a variant, a derivative or a fragment thereof (SEQ ID NO:1 or amino acids 1 to 38 of SEQ ID NO:1).

In one embodiment Y is a peptide, for example GCN4, a variant, a derivative or a fragment thereof (SEQ ID NO:1 or amino acids 1 to 38 of SEQ ID NO:1).

In one embodiment X or Y is a peptide in the range 5 to 25 amino acids in length, for example 5, 6, 7, 8, 9, 10, 11, 12, 13, 14, 15, 16, 17, 18, 19, 20, 21, 22, 23, 24 or 25 amino acids in length.

Other variants of the GCN4 peptides are shown in Table 1B (SEQ ID NO: 75-97), wherein the amino acids in bold are optional and the amino acids in italics form the sequence of the linker. It should be noted that despite variants according to sequences shown in SEQ ID NOs: 75 to 82 comprise a linker of a repetition for four times of four glycine residues and one serine (G4S), variants with linkers shorter (1×G4S, 2×G4S or 3×G4S) or longer (5×G45 etc.) are also contemplated herein).

TABLE 1B

| SEQ ID NO: 75 | *GGGGSGGGGSGGGGSGGGGS*YHLENEVARLKKLVGERHHHHHH |
| --- | --- |
| SEQ ID NO: 76 | *GGGGSGGGGSGGGGSGGGGS*YHLENEVARLKALVGERHHHHHH |
| SEQ ID NO: 77 | *GGGGSGGGGSGGGGSGGGGS*YHLENEVARLAKLVGERHHHHHH |
| SEQ ID NO: 78 | *GGGGSGGGGSGGGGSGGGGS*YHLENEVARLQKLVGERHHHHHH |
| SEQ ID NO: 79 | *GGGGSGGGGSGGGGSGGGGS*YHLENEVARLNKLVGERHHHHHH |
| SEQ ID NO: 80 | *GGGGSGGGGSGGGGSGGGGS*YHLENEVARLAALVGERHHHHHH |
| SEQ ID NO: 81 | *GGGGSGGGGSGGGGSGGGGS*YHLENEVARLQALVGERHHHHHH |
| SEQ ID NO: 82 | *GGGGSGGGGSGGGGSGGGGS*YHLENEVARLNALVGERHHHHHH |
| SEQ ID NO: 83 | *ASGGGA*MKQLEPKVEELLPKNYHLENEVARLKKLVGERHHHHHH |
| SEQ ID NO: 84 | *ASGGGR*MKQLEPKVEELLPKNYHLENEVARLKALVGERHHHHHH |
| SEQ ID NO: 85 | *ASGGGA*MKQLEPKVEELLPKNYHLENEVARLKALVGERHHHHHH |
| SEQ ID NO: 86 | *ASGGGR*MKQLEPKVEELLPKNYHLENEVARLAKLVGERHHHHHH |
| SEQ ID NO: 87 | *ASGGGR*MKQLEPKVEELLPKNYHLENEVARLQKLVGERHHHHHH |
| SEQ ID NO: 88 | *ASGGGR*MKQLEPKVEELLPKNYHLENEVARLNKLVGERHHHHHH |
| SEQ ID NO: 89 | *ASGGGA*MKQLEPKVEELLPKNYHLENEVARLAKLVGERHHHHHH |
| SEQ ID NO: 90 | *ASGGGA*MKQLEPKVEELLPKNYHLENEVARLQKLVGERHHHHHH |
| SEQ ID NO: 91 | *ASGGGA*MKQLEPKVEELLPKNYHLENEVARLNKLVGERHHHHHH |
| SEQ ID NO: 92 | *ASGGGR*MKQLEPKVEELLPKNYHLENEVARLAALVGERHHHHHH |
| SEQ ID NO: 93 | *ASGGGR*MKQLEPKVEELLPKNYHLENEVARLQALVGERHHHHHH |
| SEQ ID NO: 94 | *ASGGGR*MKQLEPKVEELLPKNYHLENEVARLNALVGERHHHHHH |

TABLE 1B-continued

SEQ ID NO: 95    A*SGGG*AMKQLEPKVEELLPKNYHLENEVARLAALVGERHHHHHH

SEQ ID NO: 96    A*SGGG*AMKQLEPKVEELLPKNYHLENEVARLQALVGERHHHHHH

SEQ ID NO: 97    A*SGGG*AMKQLEPKVEELLPKNYHLENEVARLNALVGERHHHHHH

It should be understood that A-X and Y-B fusions may be generated in various orientations which means that the polynucleotide constructs encoding such fusion may be designed to express X or A in both orientations (A-X where A's C-terminal is fused to X's N-terminal or X-A where X's C-terminal is fused to A's N-terminal). The same applies to the Y-B fusion.

Irrespective of whether A, X, Y or B is at the N-terminal of the fusion, the polynucleotide sequence to generate such fusions will comprise a nucleotide sequence designed to encode a signal peptide sequence, at the very N-terminal of the fusion, for assisting extracellular release. The signal peptide is ultimately cleaved from the mature fusion. Preferred signal peptide sequences are shown in Table 1A with SEQ ID NOs: 100-103.

In one embodiment the binding affinity between X and Y is 5 nM or stronger, for example 900 pM or stronger, such as 800, 700, 600, 500, 400 or 300 pM.

In one embodiment at least one of A or B is specific to an antigen independently selected from the group comprising: cell surface receptors such as T cell or B cell signalling receptors, co-stimulatory molecules, checkpoint inhibitors, natural killer cell receptors, Immunoglobulin receptors, immunoglobulin-like receptors, matrix metalloproteases and membrane type matrix metalloproteases tissue inhibitors of metalloproteases, TNFR family receptors, B7 family receptors, adhesion molecules, integrins, cytokine/chemokine receptors, GPCRs, growth factor receptors, kinase receptors, tissue-specific antigens, cancer antigens, pathogen recognition receptors, complement receptors, hormone receptors or soluble molecules such as cytokines, chemokines, leukotrienes, growth factors, hormones, enzymes, and ion channels, including post translationally modified version thereof, fragments thereof comprising at least one epitope.

In one embodiment at least one of A or B is specific to a cell marker, for example a B or T cell marker.

In one embodiment the multispecific protein complexes of the present disclosure are employed as preformed complexes $(A-X)_2$:$(Y-B)_2$ or as a mixture of components $(A-X)_2$ and B-Y added at the same or different times. It should be understood that each X of the $(A-X)_2$ binds to an Y of the B-Y protein fusion of the $(B-Y)_2$.

In one embodiment the complexes are employed in a method where A docks with a cell surface marker and B binds a soluble molecule secreted from a cell, or vice versa, where A binds a soluble molecule secreted from a cell and B docks with a cell surface marker.

In one embodiment A is specific to a protein (such as a cell surface marker) on a first cell and B is specific to a protein (such as a cell surface marker) on a different cell type or sub-type.

It should be understood that an alternative to the present format may be made by including A and X, each in one of the arms of a standard IgG. Hence, the variable regions of one of the two arms of an IgG will bind to, for example a cell surface marker or a soluble molecule and the variable regions of the other arm will bind to Y.

In one embodiment the soluble molecule of interest is selected from the group comprising hormones, cytokines, chemokines, chemoattractants, leukotrienes, prostaglandins, vasoactive amines, enzymes, complement and fragments of complement, lipids, sphingolipids, second messenger components (for example; nitric oxide, cyclic AMP etc.), vitamins, minerals, cations, anions, sugars, clotting factors, acute phase proteins, gamma globulins (including immunoglobulins), albumins, soluble cell membrane receptors, splice variants of cell expressed proteins, nucleic acids, small membrane vesicles (such as exosomes, microvesicles, liposomes etc.), secretory peptides, immune complexes and intracellular proteins from dead or dying cells.

In an activated status a cell may secret one or more cytokines. Thus in one embodiment the the soluble molecule is a cytokine for example GM-CSF, IFNγ, TNFα, TGFβ, CCL20, IL-2, IL-4, IL-5, IL-6, IL-9, IL-10, IL12, IL-13, IL-17, IL-18, IL-21, IL-22, IL-24, IL-26, IL-27 and IL-33. The multispecific complexes of the present disclosure may be employed for the detection of cytokine producing cells for isolation, examination, for neutralisation, and/or for targeting. This has many applications, for example it is thought that Th2 cytokine producing cells have a deleterious function in lung disease, such as asthma, for example by secreting one or more cytokines selected from the group IL-17, IL-13 and IL-5.

In one embodiment the soluble molecule of interest is a chemokine, for example selected from the group comprising CCL1, 2, 3, 4, 5, 6, 7, 8, 9/10, 11, 12, 13, 14, 15, 16, 17, 18, 19, 20, 21, 22, 23, 24, 25, 26, 27, 28, CXCL 1, 2, 3, 4, 5, 6, 7, 8, 9, 10, 11, 12, 13, 14, 15, 16, 17, XCL1, XCL2 and CX3CL1.

In one embodiment an immunoglobulin is secreted from a B-cell or plasma cell (i.e. is a soluble molecule within the context of the present disclosure), for example A is specific for the constant region of an antibody light chain or a constant region of an antibody heavy chain, expressed and secreted from the cell.

Thus in one embodiment A of the $(A-X)_2$ fusion protein is specific to a particular antibody isotype, for example selected from the group comprising IgG1, IgG2, IgG3, IgG4, IgA1, IgA2, IgE and IgM. These markers may be particularly useful for identifying class switched cells. Alternatively, A may be antigen which is capable of specifically binding to the binding domain of the immunoglobulin secreted from the cell.

In one embodiment the protein component B of the Y-B fusion is specific to an antibody, for example B is specific to a constant region of an antibody light chain or a constant region of an antibody heavy chain, in an immunoglobulin secreted by the cell. B may be is specific to a particular antibody isotype, for example selected from the group comprising IgG1, IgG2, IgG3, IgG4, IgA1, IgA2, IgE and IgM. Alternatively, B may be antigen which is capable of specifically binding to the binding domain of the immunoglobulin secreted from the cell.

Thus in one embodiment the method employs the $(A-X)_2$ binding to a cell surface marker whilst B of the Y-B is employed to capture secreted immunoglobulin.

Generally if B is specific to the immunoglobulin secreted from the cell, for example B is an antibody or binding fragment specific to an epitope in the constant region of the secreted immunoglobulin or B is an antigen to which the binding domain of the secreted immunoglobulin is specific then A will generally be directed to (specific to) a cell surface marker which is other than the corresponding surface expressed immunoglobulin.

Alternatively a B-cell marker other than an immunoglobulin can be employed to anchor the bi/multispecific protein complex to the cell surface via one binding domain in, for example B then A may comprise an antibody or binding fragment specific to an epitope in the constant region of the secreted immunoglobulin or A is an antigen to which the binding domain of the secreted immunoglobulin is specific.

The present method may be employed for the detection of antibody producing cells for isolation, examination or targeting, for example autoantibody or pathogen-specific antibody producing plasma cells (especially in the case of surface IgG negative cells).

Thus the present method can be applied to the isolation of immunoglobulin subclass specific responses, for example the specific capture of IgG4 and not other subclasses of IgG which may prove useful in the treatment or detection of IgG4-like diseases.

In one embodiment the cell surface marker is selected from a stably expressed cell lineage marker and a marker stably expressed on non-lineage cells.

In one embodiment the cell marker is selected from a B cell marker or T cell marker.

In one embodiment the B cell marker is independently selected from the group comprising CD19, CD20, CD21, CD22, CD23, CD24, CD27, CD35, CD38, CD40, B220 (also known as CD45), CD43, CD138, CXCR4, BCMA and IL-6R, for example CD38, CD138, CD45, CD27, CD19 or CD20, such as CD38 or CD138.

The skilled person is aware that some antibody expressing cells also express immunoglobulin on their surface. This surface bound immunoglobulin can be employed as a cell surface marker for an antibody producing cell. In one embodiment a binding domain in A or B is specific for the constant region of an antibody light chain or a constant region of an antibody heavy chain, expressed as part of an immunoglobulin on the surface of the cell, for example pan-specific to antibody isotypes or specific to a particular antibody isotype, for example selected from the group comprising IgG1, IgG2, IgG3, IgG4, IgA1, IgA2, IgE and IgM. In one embodiment the T cell marker is, for example selected from the group comprising CD2, CD3, CD4, CD5, CD6, CD7, CD8, CD25, CD127 CD196 (CCR6), CD197 (CCR7), CD62L, CD69 and CD45.

The complexes of the present disclosure can be used for the identification of cell populations, for example T cell populations based on their secretion phenotype by capturing a soluble molecule secreted from the cell as discussed above. An example of this is the capture of IL-17 on CD4 positive T cells to identify or isolate T helper 17 cells which have been associated with the onset and maintenance of autoimmunity.

In an activated status a cell may secrete one or more cytokines for example as described herein. The multispecific complexes of the present disclosure may be employed for the detection of cytokine producing cells for isolation, examination, for neutralisation, and/or for targeting.

It is thought that Th2 cytokine producing cells have a deleterious function in lung disease, such as asthma, for example by secreting one or more cytokines selected from the group IL-17, IL-13 and IL-5.

Chemokines which may be targeted by a binding domain in a multispecific antibody complex according to the disclosure as described above.

The antibody format of the disclosure is such that bi and multispecific antibody can be readily assembled and these can be used to screen patients (and, for example ex vivo samples therefrom, such as a blood sample) to gain insights into the disease mechanisms and/or prognosis and/or to defined patient sub-groups and/or to assign a patient to a sub-group.

The antibody complexes of the present disclosure can be prepared rapidly to include a binding domain specific for cell surface marker by which to anchor the complex on the surface of the requisite cell. A further binding domain specific to:
  a further cell surface marker,
  an antibody or binding fragment which has a binding domain specific to a cell surface marker,
  a soluble factor secreted from the cell, or
  an antigen.

Thus the bi/multispecific formats according to the disclosure are useful in the detection, identification, isolation, characterisation and/or quantification of the cells.

In one embodiment a first binding domain selected from A or B is specific to CD38, CD138, CD45, CD27, CD19 or CD20 (such as CD38 or CD138); and
a second binding domain selected from A and B is specific to CH1, CK, Fc pan isotypes, IgG1, IgG2, IgG3, IgG4, IgE or IgA.

In one aspect there is provided a method employing a heterodimerically-tethered multispecific protein complex of formula $(A-X)_2:(Y-B)_2$ according to the present disclosure wherein said method comprising the steps of:
  i) introducing to cells for analysis a combination of the fusion proteins A-X and B-Y in an uncomplexed form or $(A-X)_2:(Y-B)_2$ is added in a heterodimerically-tethered bispecific protein complex form, and
  ii) detecting the capture (for example binding) of a soluble molecule of interest by protein component B.

Furthermore, the present inventors have devised a method of detecting synergistic function in a heterodimerically-tethered multispecific protein complex of formula $(A-X)_2:(Y-B)_2$ according to the present disclosure wherein said method comprising the steps of:
  (i) testing for activity in a functional assay for part or all of a multiplex comprising at least one heterodimerically-tethered multispecific protein complex; and
  (ii) analysing the readout(s) from the functional assay to detect synergistic biological function in the heterodimerically-tethered multispecific protein complex.

Also provided is a method employing a heterodimerically-tethered bispecific protein complex of formula $(A-X)_2:(Y-B)_2$, according to the present disclosure wherein said method comprising the steps of introducing:
  (i) a combination of the fusion proteins A-X and B-Y in an uncomplexed form, or
  (ii) $(A-X)_2:(Y-B)_2$ in a heterodimerically-tethered bispecific protein complex form,
to a population of cells.

The elements described above in context of the complex per se apply equally to the complex when employed in the methods of the present disclosure.

In one embodiment $(A-X)_2$ and B-Y are added in step i) at the same time as individual components.

In one embodiment (A-X)$_2$ and B-Y are added in step i) at the same time as a preformed complex.

In one embodiment (A-X)$_2$ and B-Y are added in step i) at different times as individual components.

The format of the present disclosure is ideal for use in screening because there is no difficulty expressing the unit (A-X)$_2$ or the unit B-Y. The amount of purification required after expression of each unit (A-X)$_2$ or B-Y is minimal or in fact, unnecessary.

The multispecific complex can be formed in a 1:2 molar ratio (with 2 B-Y units) by simply admixing the relevant units i.e. without recourse to conjugation and coupling chemistry. The binding partners X and Y drive the equilibrium further in favour of forming the requisite heterodimer multispecific complex. Again little or no purification is required after formation of the complex after heterodimerisation. Thus large number's of (A-X)$_2$ and B-Y can be readily prepared and combined.

The simplicity of the multispecific complex of the invention and the methods of preparing it are a huge advantage in the context of facilitating high-through-put screening of variable domain pairs to find new target antigen combinations and also to optimise variable region sequences for a given combination.

In one embodiment the heterodimerically-tethered multispecific protein complex of the present disclosure or units thereof i.e. (A-X)$_2$ and B-Y are employed in vivo. In particular, the heterodimerically-tethered multispecific protein complex is prepared by mixing (A-X)$_2$ and B-Y in vitro. Thus in one embodiment the method comprises an in vitro mixing step bringing (A-X)$_2$ and B-Y into contact.

Thus generally the fusion proteins (A-X)$_2$ and B-Y are not co-expressed in the same cell. This is advantageous because it allows, for example 100 fusion proteins to expressed and optionally purified and the subsequent mixing of the 100 fusion proteins in the various permutations can provide 10,000 heterodimerically-tethered multispecific protein complexes, of which 5,000 are unique pairs.

In contrast certain prior art methods require co-expression of multispecifics and thus for 10,000 complexes, 10,000 transfections, expressions and purifications are required.

However, if desired the (A-X)$_2$ and B-Y may be expressed in the same cell.

The binding partners X and Y have affinity for each other and act as biological equivalent of Velcro® or a bar and magnet and hold the complex together. Advantageously, this means that the fusion proteins (A-X)$_2$ and Y-B can be readily assembled into a multispecific protein complex simply by mixing the fusion proteins together. Thus the multispecific protein complex of the present disclosure has a modular structure which allows for two different proteins, A and B, to be easily assembled in order to produce large panels of permutations of multispecific protein complexes with different combinations of antigen specificities in, for example a grid-like fashion. This allows for the efficient and systematic screening of a large number of multispecific protein complexes in order to detect additive, synergistic or novel biological function.

Given X and Y are specific for each other this significantly reduces the ability to form homodimers. X and Y are collectively referred to herein as a binding pair or binding partners. In one embodiment X does not have high affinity for other Xs. In one embodiment Y does not have high affinity for other Ys. Advantageously, when X and Y do not form homodimers, this prevents the formation of undesired monospecific protein complexes, increases yield of the desired multispecific protein complexes, and removes the need for onerous purification steps to remove the monospecific protein complexes.

This allows rapid assembly of multispecific protein complexes with a yield and/or purity which cannot be obtained efficiently by most prior art methods, in particular prior art methods generally require extensive purification steps. The yield of multispecific complex is typically 75% or higher in the present invention.

Further advantageously, the multispecific protein complexes allow for the screening of complexes wherein the constituent proteins (including antigens bound by the constituent proteins) do not have a known relationship or are in different potentially unrelated pathways, such as, two proteins which function in two distinct pathways and, for example which the skilled person would not normally expect to come into contact with each other can be tested in a multispecific protein complex to identify additive, synergistic and/or novel function. Furthermore multiple binding regions (such as variable regions) to a given antigen or epitope can be investigated in parallel to identify nuances in biological function. This allows combinations of variable region sequences directed to a given pair of antigens to be investigated and optimised.

The present method allows the science to show the results and does not rely on pre-conceived ideas and technical prejudice about the biological function. This approach is potentially very powerful.

Advantageously the X and Y components allow a multiplex comprising multispecific protein complexes made up of different permutations of fusion proteins to be assembled rapidly and easily.

In one embodiment the proteins A and B are antibodies or antibody fragments. When the antibody or antibody fragments are held together as a complex via X and Y, this forms a multispecific antibody complex.

DESCRIPTION OF DRAWINGS

FIG. 2 Is a diagrammatic representation of a grid format for screening according to the present disclosure.

DETAILED DESCRIPTION

Figure 1:
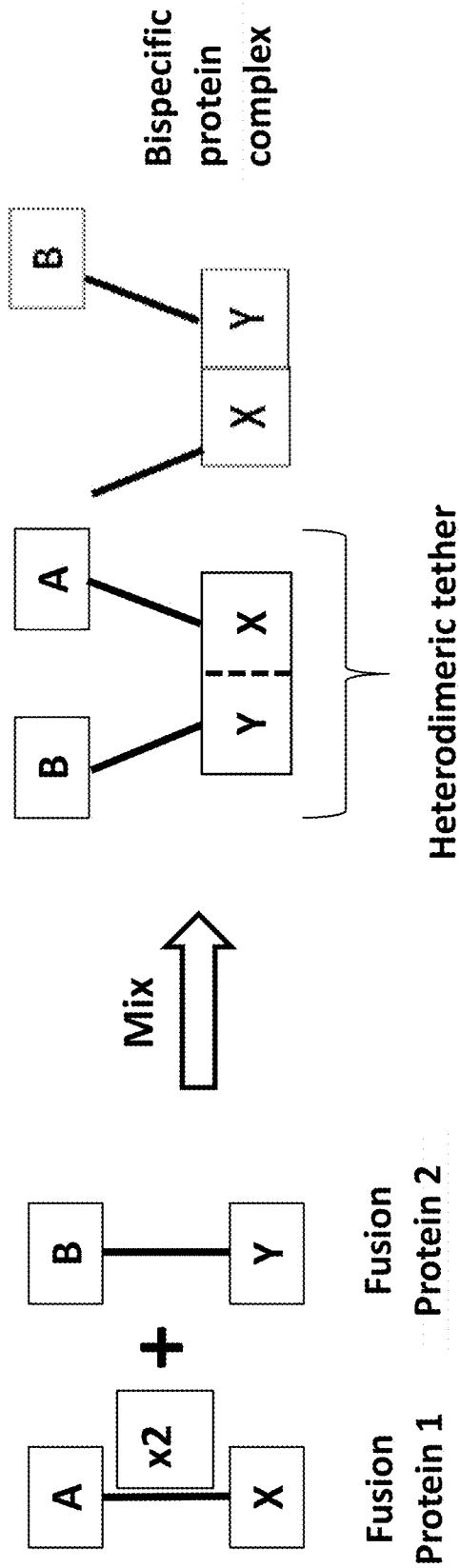
FIG. 1 Is a diagrammatic representation illustrating mixing of (A-X)$_2$ and B-Y units according to the present disclosure.

"Multispecific protein complex" as used herein refers to a molecule comprising two proteins (A and B referred to herein as multispecific components, also referred to herein as the first protein component and second protein component, respectively of the multispecific) which are retained together by a heterodimeric-tether. One or both of the proteins may comprise a further binding domain, such that the complex overall has more than two binding sites (excluding the heterodimeric tether).

Accordingly the multispecific protein complex may comprise three or more binding domains and may be for example, tri-specific. Where there are three binding sites these may independently bind the same or different antigens. In one example the complex binds two different antigens, i.e. two binding sites bind the same antigen and the third binding site binds a second, different antigen. In one example the three binding sites bind three different antigens.

"Fusion proteins" as employed herein comprise a protein component A or B fused to a binding partner X or Y (as appropriate). In one embodiment the fusion protein is a translational protein expressed by recombinant techniques from a genetic construct, for example expressed in a host from a DNA construct. In the context of the present disclosure one of the key characteristics of a fusion protein is that it can be expressed as a "single protein/unit" from a cell (of course in the case of fusion proteins comprising a Fab/Fab' fragment there will be two chains but this will be considered a single protein for the purpose of the present specification with one chain, preferably the heavy chain fused at its C-terminus to X or Y as appropriate, optionally via a linker as described herein below; other orientations such as fusion to the N-terminus to X and Y are also possible).

The function of the heterodimeric tether X:Y is to retain the proteins A and B in proximity to each other so that synergistic function of A and B can be effected or identified, for example employing the method described herein.

Unit as employed herein refers to $(A-X)_2$ and B-Y.

Component(s) as employed herein refers to a unit or a component.

The term "heterodimeric-tether" as used herein refers to a tether comprising two different binding partners X and Y which form an interaction: (such as a binding) between each other which has an overall affinity that is sufficient to retain the two binding partners together. In one embodiment X and/or Y are unsuitable for forming homodimers.

Heterodimerically-tethered and heterodimeric-tether are used interchangeably herein.

In one embodiment "unsuitable for forming homodimers" as employed herein refers to formation of the heterodimers of X-Y are more preferable, for example more stable, such as thermodynamically stable, once formed than homodimers. In one embodiment the binding interaction between X and Y is monovalent.

In one embodiment the X-Y interaction is more favourable than the X-X or Y-Y interaction.

This reduces the formation of homodimers X-X or Y-Y when the fusion proteins $(A-X)_2$ and B-Y are mixed. Typically greater than 75% heterodimer is formed following 1:1 molar ratio mixing.

If desired, a purification step (in particular a one-step purification), such as column chromatography may be employed, for example to purify the fusion protein units and/or multispecific protein complexes according to the present disclosure.

In one embodiment a purification step is provided after expression of the or each fusion protein, although typically aggregate levels are low. Thus in one embodiment prior to in vitro mixing, the fusion protein(s) is/are provided in substantially pure form. Substantially pure form as employed herein refers to wherein the fusion protein is 90, 91, 92, 93, 94, 95, 96, 97, 98, 99 or 100% monomer.

In one embodiment no purification of the fusion protein or proteins is performed.

In one embodiment each fusion protein unit is expressed in a different expression experiment/run.

In one embodiment no purification of the fusion protein or proteins is performed before mixing to generate a multispecific protein complex. In one embodiment no purification of the fusion protein or proteins is performed before and/or after mixing.

In one embodiment no purification is required after the multispecific protein complex formation.

In one embodiment after mixing, and generally without further purification, at least 50% of the composition is the desired multispecific protein complex, for example at least 60, 65, 70, 75, 80% of the composition is the required multispecific protein complex.

The present disclosure also extends to a method of preparing a multispecific complex according to the present disclosure comprising admixing a fusion protein $(A-X)_2$ and B-Y, for example in a 1:2 molar ratio.

In one embodiment the mixing occurs in vitro.

In one embodiment mixing occurs in a cell, for example a host cell.

In one embodiment, the mixing occurs in vivo, i.e. the fusion proteins $(A-X)_2$ and B-Y interact with each other within a subject's body to form the heterodimeric-tether and in consequence, the multispecific protein complex.

In one embodiment, X and Y are completely specific for each other and do not bind to any other peptides/proteins in a cell or within a subject's body. This can be achieved for example by ensuring that X and Y are not naturally present in the target cell or in the target subject's body. This can be achieved, for example by selecting X or Y to be from a species or entity which is different to the subject (e.g. a yeast protein) and ensuring the other variable is specific to it. Advantageously, this prevents the binding of the fusion proteins A-X and/or B-Y to an undesired target, thereby generating unwanted off-target effects.

In one embodiment one (or at least one) of the binding partners is incapable of forming a homodimer, for example an amino acid sequence of the binding partner is mutated to eliminate or minimise the formation of homodimers.

In one embodiment both of the binding partners are incapable of forming a homodimer, for example an amino acid sequence of the peptide binding partner is mutated to eliminate or minimise the formation of homodimers and a VHH specific thereto is employed.

Incapable of forming homodimers or aggregates as employed herein, refers to a low or zero propensity to form homodimers or aggregate. Low as employed herein refers to 5% or less, such as 4, 3, 2, 1, 0.5% or less aggregate, for example after mixing or expression or purification.

Small amounts of aggregate in the fusion proteins or residual in the heterodimerically-tethered multispecific protein complex generally has minimal effect on the screening method of the present disclosure. Therefore, in one embodiment no purification of fusion protein(s) and/or multispecific protein complex(es) is/are employed in the method, in particular after the mixing step.

In one embodiment: is a binding interaction based on attractive forces, for example Van der Waals forces, such as hydrogen bonding and electrostatic interactions, in particular, based on antibody specificity for an antigen (such as a peptide).

In one embodiment: is a covalent bond formed from a specific chemical interaction, such as click chemistry. In one embodiment: is not a covalent bond. In one embodiment conjugation/coupling chemistry is not employed to prepare the multispecific protein complexes of the present disclosure.

"Form the complex" as employed herein refers to an interaction, including a binding interaction or a chemical reaction, which is sufficiently specific and strong when the fusion protein components A-X and B-Y are brought into contact under appropriate conditions that the complex is assembled and the fusion proteins are retained together.

"Retained together" as employed herein refers to the holding of the components (the fusion proteins) in the proximity of each other, such that after X:Y binding the complex can be handled as if it were one molecule, and in many instances behaves and acts like a single molecule. In one embodiment the retention renders the complex suitable for use in the method disclosed herein, i.e. suitable for use in at least one functional screen.

Specificity as employed herein refers to where, for example the partners in the interaction e.g. X:Y or A and antigen or B and antigen only recognise each other or have significantly higher affinity for each other in comparison to non-partners, for example at least 2, 3, 4, 5, 6, 7, 8, 9, 10 times higher affinity, than for example a background level of binding to an unrelated non partner protein.

Specificity in relation to X and Y as employed herein refers to where the binding partners X and Y in the interaction only recognise each other or have significantly higher affinity for each other in comparison to non-partners, for example at least 2, 3, 4, 5, 6, 7, 8, 9, 10 times higher affinity.

In one embodiment the binding interaction is reversible. In one embodiment the binding interaction is essentially irreversible.

Essentially irreversible as employed herein refers to a slow off rate (dissociation constant) of the antibody or binding fragment.

In one embodiment, the binding interaction between X and Y has a low dissociation constant. Examples of a low dissociation constant include $1-9 \times 10^{-2}$ $s^{-1}$ or less, for example $1-9 \times 10^{-3}$ $s^{-1}$, $1-9 \times 10^{-4}$ $s^{-1}$, $1-9 \times 10^{-5} s^{-1}$, $1-9 \times 10^{-6}$ $s^{-1}$ or $1-9 \times 10^{-7}$ $s^{-1}$. Particularly suitable dissociation constants include $2 \times 10^{-4} s^{-1}$ or less, for example $1 \times 10^{-5} s^{-1}$, $1 \times 10^{-6} s^{-1}$ or $1 \times 10^{-7} s^{-1}$.

Whilst not wishing to be bound by theory it is thought that the low dissociation constant (also referred to as off rate) allows the molecules to be sufficiently stable to render the multispecific protein complex useful, in particular in functional screening assays.

In one embodiment, the affinity of X and Y for each other is 5 nM or stronger, for example 900 pM or stronger, such as 800, 700, 600, 500, 400, 300, 200, 100 or 50 pM or stronger.

In another embodiment, the affinity of X and Y for each other is 10 pM or stronger, for example 9, 8, 7, 6 or 5 pM.

Affinity is a value calculated from the on and off rate of the entity. The term "affinity" as used herein refers to the strength of the sum total of non-covalent interactions between a single binding site of a molecule (e.g. an antibody) and its binding partner (e.g. a peptide). The affinity of a molecule for its binding partner can generally be represented by the dissociation constant (KD). Affinity can be measured by common methods known in the art, including those described herein, such as surface plasmon resonance methods, in particular BIAcore.

However, the ability to hold the complex together is not just about affinity. Whilst not wishing to be bound by theory, we hypothesise that in fact there are three significant components: the on-rate, off-rate and the affinity. The calculation for affinity is based on on-rate and off-rate. So if the on-rate is low and the off-rate is fast, then the affinity will be low and that will not be sufficient to hold the multispecific protein complex together. However, a slow on-rate could be compensated for by a slow off-rate giving an overall suitable affinity. In some embodiments a high on-rate may be sufficient to hold the complex together.

If the binding partners (X and Y) employed in the complex have a slow on-rate then additional time may be required after mixing the components to allow the complex to form.

If the affinity between the binding partners is sufficiently high, it may be possible for the multispecific protein complex to perform its desired biological function even if the affinity of the proteins (A and B) of the multispecific protein complex only bind weakly to their targets.

Conversely, if the proteins (A and B) are able to bind strongly to their targets, it may be possible to achieve the same biological function even if the affinity of the binding partners (X and Y) for each other is lower. In other words, a 'trinity' relationship exists such that a higher affinity between the binding partners can compensate for a lower affinity for the targets and vice versa.

The multispecific protein complexes of the present invention may be used in any suitable application, including functional screening. This novel format is particularly useful in multiplex functional screening to identify protein targets based on function, and optimal epitopes on those target proteins, which could be targeted by multispecific therapies. Furthermore where proteins A and B are antibodies or binding fragments thereof the multispecific protein complexes may also be used for multiplex functional screening to identify optimal variable region pairs for use in multispecific antibody therapeutics.

"Multiplex" as employed herein is a population of entities for testing comprising:

at least two component fusion proteins ($(A-X)_2$ and $(Y-B)_2$) combined to generate at least one heterodimerically-tethered multispecific protein complex and at least one relevant biological comparator in the same or a different format, or at least two heterodimerically-tethered multispecific protein complexes with optionally at least one relevant biological comparator in the same or a different format.

Clearly to be useful, the different format employed as the comparator must be suitable for testing in a functional in vitro assay employed in the disclosure. In one example the comparator in the multiplex is a monovalent mixture of $(A-X)_2$ and B-Y or a bivalent monospecific complex of $(A-X)_2-Y-A$.

In one embodiment the multiplex comprises 1 to hundreds of thousands of heterodimerically-tethered multispecific protein complexes, for example 2 to 500,000 of said complexes, such as 2 to 100,000 or 2 to 10,000, in particular generated from mixing in a grid 2 to 100s of first and second fusion proteins ($(A-X)_2$ and Y-B). In one embodiment the multiplex comprises for example 2 to 1,000, such as 2 to 900, 2 to 800, 2 to 700, 2 to 600, 2 to 500, 2 to 400, 2 to 300, 2 to 200, 2 to 100, 2 to 90, 3 to 80, 4 to 70, 5 to 60, 6 to 50, 7 to 40, 8 to 30, 9 to 25, 10 to 20 or 15 multispecific protein complexes.

In one embodiment the number of heterodimerically-tethered multispecific proteins in this multiplex is $n^2$ where n is 1, 2, 3, 4, 5, 6, 7, 8, 9, 10, 11, 12, 13, 14, 15 or more.

The multiplex may be in the form of an array, for example a microtitre plate, wherein each well of the microplate may contain a different multispecific protein complex. The multispecific protein complexes may be tethered to a solid substrate surface, for example attached to a bead, or they may be suspended in a liquid (e.g. a solution or media) form, for example within a well or within a droplet.

In one embodiment every 'A' in the multiplex is a different protein, preferably an antibody or binding fragment thereof that binds to a target antigen and every 'B' is a different protein preferably an antibody or binding fragment thereof that binds to a target antigen.

In one embodiment the multiplex is provided in a grid as discussed below, for example an 8×8, 16×16 or 16×20, which equates to 64, 256 or 320 samples respectively.

"Grid" as employed herein refers to a two dimensional plot or array where one variable, such a protein A (in $(A-X)_2$) is varied along one axis, such as the X-axis (horizontal axis) and another variable such as protein B (in B-Y) is varied along the other axis, such as the Y axis (vertical axis). This arrangement assists in systematically evaluating the various combinations (permutations) of the variables.

In one embodiment the multiplex is provided on 96 well plates and the samples analysed may be multiples thereof i.e. 96, 192, 384 etc.

Advantageously, a grid arrangement is particularly advantageous for efficiently screening the biological function of multispecific protein complexes according to the present disclosure. An example of such a grid, whereby 4 first fusion proteins can be readily combined with 4 second fusion proteins to produce 16 multispecific protein complexes.

Other variations of a screening grid will be apparent to the skilled addressee, for example the first protein (A) in the first fusion protein $(A-X)_2$ may be kept constant whilst the second protein (B) in the second fusion protein (B-Y) is varied. This may be useful for quickly screening a large number of different second proteins for synergistic function with the pre-selected first protein.

In another embodiment, protein A is varied along one axis by changing the antibody variable regions of protein A such that each antibody variant is specific for the same antigen but has a different combination of variable regions. Protein B may either be kept constant or may also be varied in the same fashion or varied such that the antigen specificity changes (across or down the grid) for the B proteins.

Advantageously, such a screening grid may potentially allow for the detection of small differences in synergistic function when the multispecific protein complexes are specific for the same antigens but with different combinations of variable regions.

In one embodiment, a "common" first fusion protein $(A-X)_2$ according to the present disclosure may be present within each well. A range of different second fusion proteins (B-Y) according to the present disclosure may then be dispensed into each well. Subsequently, the specific binding interaction of the two binding partners (X and Y) physically brings the two fusion proteins together to form the multispecific protein complexes. This results in a multiplex comprising multispecific protein complexes which all bind to a common first target antigen (bound by A) but are also capable of binding to a second target antigen (bound by B) which may be different for each multispecific protein complex.

In one embodiment the B-Y fusion proteins comprise different variable regions to the same target antigen to allow optimisation of the variable regions and/or epitopes of the given target antigen bound by B when combined with the variable regions in $(A-X)_2$.

"Common" first fusion protein as employed herein refers to fusions proteins wherein the A or B component thereof, bind the same proteins or epitope, in particular where the A or B component have complete identity in the common fusion protein i.e. the common first fusion protein always comprises the same variable region sequence.

The skilled person is also aware of different variations of the above, such that the desired specificities of the multispecific protein complexes at each position in the multiplex can be readily controlled. This allows for the efficient screening of different combinations of multispecific protein complexes when such multiplexes are used in functional assays. In one embodiment factorial design is employed to define the variables employed in the grid.

In one embodiment the method of the present disclosure is conducive to high-throughput analysis.

In one embodiment, multiple multispecific protein complexes are tested in parallel or essentially simultaneously.

Simultaneously as employed herein refers to the where the samples/molecules/complexes are analysed in the same analysis, for example in the same "run". This may be advantageous as generally the reagents employed for a given sample run will be the same batch, concentration, cell source etc and therefore have the same properties. Furthermore the environmental conditions under which the analysis is performed, such as temperature and humidity are likely to be similar.

In one embodiment simultaneously refers to concomitant analysis where the signal output is analysed by an instrument at essentially the same time. This signal may require deconvolution to interpret the results obtained.

Advantageously, testing multiple multispecific protein complexes allows for more efficient screening of a large number of multispecific protein complexes and the identification of new and interesting relationships.

In one embodiment, the multiple multispecific protein complexes are tested by using a multiplex as defined above and subjecting the same to one or more functional assays.

The term "biological function" as used herein refers to an activity that is natural to or the purpose of, the biological entity being tested, for example a natural activity of a cell, protein or similar. Ideally the presence of the biological function can be tested using an in vitro functional assay, including assays employing mammalian cells, such as living cells, such as B or T cells, or tissue ex vivo. Natural function as employed herein also includes aberrant function, such as functions associated with diseases, such as cancers.

A relevant "biological comparator" as employed herein refers to a suitable entity for assessing activity, in the same assay as that employed for the multispecific protein complex, to establish if there is any change or novel activity or function. Suitable comparators for $(A-X)_2:(Y-B)_2$ may include a purified protein (including recombinant proteins) in a natural form or presented in the same format as the multispecific e.g., where A and B are the same entity, such as $(A-X)_2:(Y-A)_2$ or B-X:Y-B i.e. a bivalent monospecific complex. Alternatively the fusion protein $(A-X)_2$ or B-Y in an uncomplexed form may be employed as a comparator alone or as an uncomplexed mixture such as $(A-X)_2$ and B-X together or $(A-Y)_2$ and B-Y together. Alternatively, multiple comparators of different formats (in particular as described herein) may be employed. The person skilled in the art is able to identify and include a suitable control/comparator based on common general knowledge or information that is found in the literature.

The term "synergistic function" or "synergistic biological function" as used herein refers to a biological activity or level of biological activity or an effect on a biological function or activity that:
  is not observed with individual fusion protein components until a multispecific is employed (and may include activity observed with a combination of antibodies to the said antigens, which are not in an multispecific format, but in particular refers to activity only observed when the two binding domains are linked in a multispecific format) or
  higher or lower activity in comparison to the activity observed when the first and second proteins of a multispecific protein complex of the present disclosure are employed individually, for example activity which is only observed in a multispecific form.

Therefore, "synergistic" includes novel biological function or novel activity. Synergistic function as employed herein does not generally include simple targeting i.e. based only on binding but will generally involve some inhibition, activation, signalling or similar after binding.

Novel biological function or novel activity as employed herein refers to a biological function or activity which is not apparent or is absent until the two or more synergistic entities (protein A and protein B) are brought together (as a multispecific or otherwise) or a previously unidentified function.

Higher as employed herein refers to an increase in activity including an increase from zero e.g., some activity in the multispecific where the individual uncomplexed multispecific component or components has/have no activity in the relevant functional assay, also referred to herein as new activity or novel biological function. Higher as employed herein also includes a greater than additive function in the multispecific in a relevant functional assay in comparison to the individual uncomplexed multispecific components (tested alone or in combination with being linked), for example 10, 20, 30, 40, 50, 60, 70, 80, 90, 100, 200, 300% or more increase in a relevant activity.

In one embodiment the uncomplexed proteins together have the same activity as the multispecific and this activity or function was previously unknown. This is also a novel synergistic function in the context of the present specification.

In one embodiment the synergistic function is a higher function.

In one embodiment the synergistic function is a lower function.

Lower function as employed herein refers to where the multispecific in the relevant functional assay has less or no activity in comparison to the individual uncomplexed multispecific component (s) which has/have activity in the relevant functional assay, also referred to herein as new activity or novel biological function (such as a natural protein i.e. a recombinant isolated protein which is not in a fusion protein nor part of any other complex other than one in which occurs in vivo-including an active domain or fragment of said protein) analysed as an individual protein or analysed as a mixture of proteins under the same conditions, for example 10, 20, 30, 40, 50, 60, 70, 80, 90, 100, 200, 300% or more decrease in a relevant activity. Greater than 100% decrease in activity refers to a gain in positive activity in a different direction, for example where an entity is an agonist decrease in activity over 100% may render the entity an antagonist and vice versa.

In one embodiment the activity of the multispecific complex is lower than the sum of the known function of protein A and protein B.

In some embodiments the multispecific protein complexes of the present disclosure have simply additive biological function. Additive biological function as employed herein refers to function, which is the same as the sum of each of the components A and B individually, when tested under the same conditions. An additive function may be a novel function if the activity or function was previously unknown or unidentified.

Screening is performed using any suitable assay known in the art, depending on the desired function to be identified.

In one embodiment, the functional assay employed in a method of the present disclosure is an in vitro or ex vivo assay.

A "functional assay," as used herein, is an assay that can be used to determine one or more desired properties or activities of the multispecific protein complexes, antibody complexes or the mixture of antibodies subject to the assay conditions. Suitable functional assays may be binding assays, apoptosis assays, antibody-dependent cellular cytotoxicity (ADCC) assays, complement-dependent cytotoxicity (CDC) assays, inhibition of cell growth or proliferation (cytostatic effect) assays, cell-killing (cytotoxic effect) assays, cell-signalling assays, cytokine production assays, antibody production and isotype switching, cellular differentiation assays, colony forming assays, chemotaxis assays, cell adhesion assays, cell migration assays, cell cycle assays, metabolic assays (whole cell and organelle function), assays for measuring inhibition of binding of pathogen to target cell, assays to measure the secretion of vascular endothelial growth factor (VEGF) or other secreted molecules, assays for bacteriostasis, bactericidal activity, neutralization of viruses, assays to measure the attraction of components of the immune system to the site where antibodies are bound, including in situ hybridization methods, labeling methods, and the like.

In one embodiment in vivo assays, such as animal models, including mouse tumor models, models of auto-immune disease, virus-infected or bacteria-infected rodent or primate models, and the like, may be employed.

The skilled person is well able to select a suitable functional assay based on the target/proteins being investigated. However, the complexes may be subject to a panel of "standard" assays without preselecting assays thought to be relevant in an attempt identify new functionality.

In the context of multispecific antibody complexes, the efficacy of multispecific antibody complexes according to the present disclosure can be compared to individual antibodies or mixtures of antibodies (or fragments) in such models by methods generally known to one of ordinary skill in the art.

For example, the multispecific antibody complexes may be tested for the ability to inhibit proliferation, affect viability or metabolic activity of cells (for example with a stain such as allamar blue or by monitoring luminescence due to luciferase expressed by the cells), or cause apoptosis of cancer cells, which are biological functions that include properties other than binding to an antigen.

By choosing functional assays closely related to a particular disease of interest, the methods of the disclosure make it possible to identify potentially therapeutic antibodies that bind to known or unknown target molecules. It is thus possible to identify new target molecules and/or to directly identify potentially therapeutic antibodies using the methods of the disclosure. Advantageously, the present method is not limited to any particular assay(s) and provides the user with complete flexibility to select the most appropriate functional assay depending on the requirements.

When screening the multispecific antibody complexes for desired biological function, various strategies may be employed. For example, medium containing the antibodies can be directly screened for the biological activity. Alternatively, the antibodies can be bound to beads coated or to microtiter plates prior to screening for biological activity. Alternatively a fusion protein maybe purified via a His tag in a nickel capture purification step. Such strategies may increase local concentrations of the antibodies leading to clearer results from the functional assays.

The functional assays may be repeated a number of times as necessary with or without different samples of a particular multispecific antibody complex to enhance the reliability of the results, Various statistical tests known to the skilled person can be employed to identify statistically significant results and thus identify multi specific antibody complexes with biological functions.

When establishing a functional assay for screening the skilled person can set a suitable threshold over which an identified activity is deemed a 'hit'. Where more than one functional assay is used the threshold for each assay may be set at a suitable level to establish a manageable hit rate. In one example the hit rate may be 3-5%. In one example the criteria set when searching for pairs of antigens that inhibit B cell function may be at least 30% inhibition of at least two phospho-readouts in a B cell activation assay.

In the multispecific protein complexes of the present invention the following protein and peptide components may be used.

In one embodiment, at least one of the first binding partner, X, and the second binding partner, Y, of the binding pair are independently selected from a peptide and a protein; for example the first binding partner or second binding partner is a peptide.

Suitable peptides include the group comprising GCN4, Fos/Jun (human and murine Fos have a Uniprot number P01100 and P01101 respectively and human and murine jun have a Uniprot number 05412 and 05627 respectively), HA-tag which correspond to amino acids 98 to 106 of human influenza hemagglutinin, polyhistidine (His), c-myc and FLAG. Other peptides are also contemplated as suitable for use in the present disclosure and particularly suitable peptides are affinity tags for protein purification because such peptides have a tendency to bind with high affinity to their respective binding partners.

In one embodiment the peptide is not E5B9.

The term "peptide" as used herein refers to a short polymer of amino acids linked by peptide bonds, wherein the peptide contains in the range of 2 to 100 amino acids, for example 5 to 99, such as 6 to 98, 7 to 97, 8 to 96 or 5 to 25. In one embodiment a peptide employed in the present disclosure is an amino acid sequence of 50 amino acid residues or less, for example 40, 30, 20, 10 or less. The peptides used in the present disclosure are of a sufficient length to be fit for purpose, for example if the peptide is a linker, it needs to be suitably long to allow the fragment which it links to perform its biological function; alternatively if the peptide is a binding partner, it must be capable of binding specifically to another entity such as an antibody.

In one embodiment, the other binding partner of the binding pair (the alternative first or second binding partner) is an antigen.

In one embodiment, the protein is an antibody or an antibody fragment.

The term "antibody" as used herein refers to an immunoglobulin molecule capable of specific binding to a target antigen, such as a carbohydrate, polynucleotide, lipid, polypeptide, peptide, protein etc., via at least one antigen recognition site (also referred to as a binding site herein), located in the variable region of the immunoglobulin molecule.

As used herein, the term "antibody" or "antibody molecule" includes antibodies and antigen-binding fragments thereof.

The term "antigen-binding fragments" or "antibody fragments" as employed herein refers to fragments of an antibody and includes but is not limited to Fab, modified Fab, Fab', modified Fab', F(ab')2, Fv, single domain antibodies (sdAb), scFv, bi, tri or tetra-valent antibodies, Bis-scFv, diabodies, triabodies, tetrabodies and epitope-binding fragments of any of the above (see for example Holliger and Hudson, 2005, Nature Biotech. 23(9):1126-1136; Adair and Lawson, 2005, Drug Design Reviews—Online 2(3), 209-217). The methods for creating and manufacturing these antibody fragments are well known in the art (see for example Verma et al., 1998, Journal of Immunological Methods, 216:165-181). Other antibody fragments for use in the present disclosure include the Fab and Fab' fragments described in International patent applications WO05/003169, WO05/003170 and WO05/003171. Multi-valent antibodies may comprise multiple specificities e.g. multispecific or may be monospecific (see for example WO92/22853, WO05/113605, WO2009/040562 and WO2010/035012).

An "antigen-binding fragment" as employed herein refers to a fragment, for example of an antibody or of another molecule, capable of binding a target peptide or antigen with sufficient affinity to characterise the fragment as specific for the peptide or antigen.

The term "Fab fragment" as used herein refers to an antibody fragment comprising a light chain fragment comprising a VL (variable light) domain and a constant domain of a light chain (CL), and a VH (variable heavy) domain and a first constant domain (CH1) of a heavy chain. In one example the heavy chain sequences of the Fab fragment "terminates" at the interchain cysteine of CH1. In one embodiment the Fab fragment employed in a fusion protein of the present disclosure, such as A-X and/or B-Y is monovalent.

A Fab' fragment as employed herein refers to a Fab fragment further comprising all or part of a hinge region. In one embodiment the Fab' fragment employed in a fusion protein of the present disclosure, such as A-X and/or B-Y is monovalent.

The term "single-chain Fv" or abbreviated as "scFv", as used herein refers to an antibody fragment that comprises VH and VL antibody domains linked (for example by a peptide linker) to form a single polypeptide chain. The constant regions of the heavy and light chain are omitted in this format. Single-chain Fv as employed herein includes disulfide stabilised versions thereof wherein in addition to the peptide linker a disulfide bond is present between the variable regions.

Disulfide stabilised scFv may eliminate the propensity of some variable regions to dynamically "breath", which relates to variable regions separating and coming together again.

The term "single domain antibody" as used herein refers to an antibody fragment consisting of a single monomeric variable antibody domain. Examples of single domain antibodies include VH or VL or sdAb.

The term "sdAb" or "single domain antibodie(s)" as used herein refers to molecules comprising a single antigen-binding domain. They may be artificially created or naturally occurring and include, but are not limited to, VH only, VL only, camelid VHHs, human domain antibodies, shark derived antibodies such as IgNARs and other non-antibody single domain binding formats, including but not limited to, adnectins, lipocalins, Kunitz domain-based binders, avimers, knottins, fynomers, atrimers, cytotoxic T-lymphocyte associated protein-4 (CTLA4)-based binders, darpins, affibodies, affilins, armadillo repeat proteins.

In B, Fc regions such as CH2, CH3 and CH4 are absent. However, constant domains such as CH1, CKappa/CLambda may be present.

In one embodiment, the antibody heavy chain comprises a CH1 domain and the antibody light chain comprises a CL domain, either kappa or lambda.

In one embodiment, the antibody heavy chain comprises a CH1 domain, a CH2 domain and a $CH_3$ domain and the antibody light chain comprises a CL domain, either kappa or lambda.

Multispecific protein complex and multispecific antibody complex are employed interchangeably herein.

"Multispecific antibody complex" as employed herein refers to a multispecific protein complex comprising at least two antibody binding sites wherein the component antibodies, fragments or both are complexed together by a heterodimeric-tether.

A multispecific antibody complex usually refers to a molecule comprising at least two antigen binding sites, wherein the binding sites have non-identical specificity.

In one embodiment, the two proteins (for example antibodies, fragments or a combination of an antibody and a fragment) target the same antigen, for example binding to two different epitopes on the same target antigen, also referred to herein as a biparatopic multispecific.

In another embodiment, the two proteins (for example antibodies, fragments or a combination of an antibody and a fragment) may have different antigen specificities, for example binding to two different target antigens.

In yet another embodiment, the two proteins are identical, i.e. binding to the same epitope on the same target antigen and the complex is therefore monospecific.

In one embodiment each antibody or fragment employed in the multispecific antibody complex of the disclosure comprises one binding site i.e. each binding site is monovalent for each target antigen.

The full length antibody or antibody fragment employed in the fusion proteins ((A-X)$_2$ or B-Y) may be monospecific, monovalent, multivalent or multispecific.

Advantageously, the use of two multispecific antibody or antibody fragments allows the multispecific antibody complex of the present disclosure to potentially be specific for up to 4 different antigens (i.e. the complex may be tetraspecific). This allows avidity type effects to be investigated.

In one embodiment, the antibody or antibody fragment employed in the second fusion protein (B-Y) is a monospecific antibody or antibody fragment, in particular a monovalent Fab, Fab', scFv or similar.

"Monospecific" as employed herein refers to the ability to bind only one target antigen.

"Monovalent" as employed herein refers to the antibody or antibody fragment having a single binding site and therefore only binding the target antigen only once. "Multivalent" as used herein refers to antibodies or fragments thereof having at least two binding sites capable of binding to two or more epitopes with the same, identical specificity, e.g. repeating identical units on the surface of a virus particle.

In one embodiment, the antibody employed in the first fusion protein (A-X)$_2$ is multivalent, that is has two or more binding domains.

In one embodiment, the antibody or antibody fragment employed in the second fusion protein (B-Y) is multivalent, that is has two or more binding domains.

In one embodiment, the antibody employed in the first fusion protein (A-X)$_2$ is multivalent and the antibody or antibody fragment employed in the second fusion protein (B-X) is monovalent.

In one embodiment, the antibody employed in the first fusion protein (A-X)$_2$ is multivalent and the antibody or antibody fragment employed in the second fusion protein (B-Y) is multivalent.

In one embodiment (A-X)$_2$ or B-Y is not a fusion protein comprising two scFvs one specific to the antigen CD33 and one specific to the antigen CD3 or alternatively a multispecific complex format specific to these two antigens.

In one embodiment the (A-X)$_2$ or B-Y is not a fusion protein comprising a scFv (or alternatively another antibody format) specific to CD3 linked to a peptide E5B9.

A "binding domain or site" as employed herein is the part of the antibody that contacts the antigen/epitope and participates in a binding interaction therewith. In one embodiment the binding domain contains at least one variable domain or a derivative thereof, for example a pair of variable domains or derivatives thereof, such as a cognate pair of variable domains or a derivative thereof.

In one embodiment the binding domain comprises 3 CDRs, in particular where the binding domain is a domain antibody such as a VH, VL or VHH. In one embodiment the binding domain comprises two variable domains and 6 CDRs and a framework and together these elements contribute to the specificity of the binding interaction of the antibody or binding fragment with the antigen/epitope.

A "cognate pair" as employed herein refers to a heavy and light chain pair isolated from a host immune cell such as a B-cell as a pre-formed couple. This definition does not include variable domains isolated from a library, wherein the original pairings from a host immune cell such as a B-cell is not retained. Cognate pairs may be advantageous because they are often affinity matured in the host and therefore may have high affinity for the antigen to which they are specific.

A "derivative of a naturally occurring domain" as employed herein is intended to refer to where one, two, three, four, five or more amino acids in a naturally occurring sequence have been replaced or deleted, for example to optimize the properties of the domain such as by eliminating undesirable properties but wherein the characterizing feature(s) of the domain is/are retained. Examples of modifications are those to remove glycosylation sites or solvent exposed lysines. These modifications can be achieved by replacing the relevant amino acid residues with a conservative amino acid substitution.

In one embodiment, the multispecific antibody complexes of the present disclosure or antibody/fragment components thereof are processed to provide improved affinity for a target antigen or antigens. Such variants can be obtained by a number of affinity maturation protocols including mutating the CDRs (Yang et al., J. Mol. Biol., 254, 392-403, 1995), chain shuffling (Marks et al., Bio/Technology, 10, 779-783, 1992), use of mutator strains of *E. coli* (Low et al., J. Mol. Biol., 250, 359-368, 1996), DNA shuffling (Patten et al., Curr. Opin. Biotechnol., 8, 724-733, 1997), phage display (Thompson et al., J. Mol. Biol., 256, 77-88, 1996) and sexual PCR (Crameri et al., Nature, 391, 288-291, 1998). Vaughan et al. (supra) discusses these methods of affinity maturation.

In one embodiment, the first antibody or antibody fragment (A) is specific to a first antigen and the second antibody or antibody fragment (B) is specific to a second antigen, wherein the first and second antigens are different. Advantageously, the bispecific antibody complex may be specific for two different antigens. This presents the possibility of the antibody complex binding to two different antigens, each located on a different entity, thereby bringing the two entities into close physical proximity with each other.

Alternatively, the first antibody or antibody fragment (A) may be specific for a first epitope and the second antibody or antibody fragment (B) may be specific for a second epitope, wherein the first and second epitopes are both on the same antigen. This can greatly enhance the avidity of the multispecific antibody complex for the antigen due to the multiple interactions between the antigen and multispecific antibody complex.

In one embodiment, the first antibody (A) of a multispecific antibody complex of the present disclosure may be an IgG, optionally with an inactive or active Fc region. In one embodiment, the second (B) antibody fragment is selected from the group consisting of: a fragment antigen binding (Fab), a Fab', a single chain variable fragment (scFv) and a single domain antibody (sdAb), such as a VHH.

In one embodiment, the second antibody/fragment (B) or both the first and second antibody/fragment of the multispecific antibody complex of the present disclosure may be a Fab.

In one embodiment, the second antibody/fragment (B) or both the first and second antibody/fragment of the multispecific antibody complex of the present disclosure may be a Fab'.

In one embodiment, second antibody/fragment (B) or both the first and second antibody/fragment of the multispecific antibody complex of the present disclosure may be a scFv.

In one embodiment, the second (B) antibody/fragment or both the first and second antibody/fragment of the multispecific antibody complex of the present disclosure is/are a sdAb.

"Attached" as employed herein refers to connected or joined directly or indirectly via a linker, such as a peptide linker examples of which are discussed below. Directly connected includes fused together (for example a peptide bond) or conjugated chemically.

"Binding partner" as employed herein refers to one component part of a binding pair.

In one embodiment, the affinity of the binding partners is high, 5 nM or stronger, such as 900, 800, 700, 600, 500, 400, 300 pM or stronger.

"Binding pair" as employed herein refers to two binding partners which specifically bind to each other. Examples of a binding pair include a peptide and an antibody or binding fragment specific thereto, or an enzyme and ligand, or an enzyme and an inhibitor of that enzyme.

When X is an antibody or binding fragment thereof then Y is a protein or peptide, in particular a peptide.

In one embodiment, the second partner (Y) is selected from the group comprising: a full length antibody, a Fab, a Fab', Fv, dsFv, a scFv and a sdAb, wherein examples of a sdAb include VH or VL or VHH.

When Y is an antibody or binding fragment thereof then X is a protein or peptide, in particular a peptide.

In one embodiment, where A is an antibody or fragment thereof the first binding partner (X) is attached to the C-terminal of the heavy or light chain of the first antibody or antibody fragment, for example, the first binding partner (X) is attached to the C-terminal of the heavy chain of the first antibody or antibody fragment (A).

In another embodiment, where B is an antibody or fragment thereof the second binding partner (Y) is attached to the C-terminal of the heavy or light chain of the second antibody or antibody fragment, for example the second binding partner (Y) is attached to the C-terminal of the heavy chain of the second antibody or antibody fragment (B).

In one embodiment X is attached to the C-terminal of the heavy chain of the antibody or fragment (protein A) and Y is attached to the C-terminal of the heavy chain of the antibody or fragment (protein B).

In one embodiment X is attached via a linker (such as ASGGGG SEQ ID NO: 71 or ASGGGGSG SEQ ID NO: 72), or ASGGG SEQ ID NO: 73 or AAASGGG SEQ ID NO: 74 or any other suitable linker known in the art or described herein below, to the C-terminal of the heavy chain of the antibody or fragment (protein A) and Y is attached via a linker (such as ASGGGG SEQ ID NO: 71 or ASGGGGSG SEQ ID NO: 72) to the C-terminal of the heavy chain of the antibody or fragment (protein B).

Examples of a suitable binding pair (X or Y) may include GCN4 (SEQ ID NO: 1 or lacking the HIS tag, amino acids 1-38 of SEQ ID NO: 1), a variant, a derivative or fragment thereof (for example any of the sequences shown by SEQ ID NOs: 75-97) and 52SR4 (SEQ ID NO: 3 or lacking the HIS tag amino acids 1 to 243 of SEQ ID NO:3) or a variant thereof, which is a scFv specific for GCN4.

In a one embodiment, the first binding partner (nominally X) is GCN4 (for example as shown in SEQ ID NO: 1) or a fragment or a derivative or a variant thereof (for example without the His tag or as shown in any one of the sequences shown by SEQ ID NOs: 75-97) and the second binding partner (nominally Y) is a scFv or sdAb specific for GCN4 (for example as shown in SEQ ID NO: 3) or a variant or a derivative thereof (for example any of the sequences shown by SEQ ID NOs: 98 or 99).

In one embodiment, the first binding partner (nominally X) is a sFv or sdAb specific for GCN4 (for example as shown in SEQ ID NOs: 3, 98 or 99) or a variant thereof and the second binding partner (nominally Y) is GCN4 (for example as shown in SEQ ID NO: 1) or a fragment or variant thereof (for example any of the sequences shown by SEQ ID NOs: 75-97).

GCN4 variants include an amino acid sequence with at least 80%, 85%, 90%, 91%, 92%, 93%, 94% 95%, 96%, 97% or 98%, or 99% identity to SEQ ID NO: 1. GCN4 variants also include an amino acid having at least 80%, 85%, 90%, 91%, 92%, 93%, 94%, 95%, 96%, 97%, 98%, or 99% to a sequence encoded by a nucleotide sequence SEQ ID NO: 2, or a sequence encoded by a nucleotide sequence which hybridises to SEQ ID NO: 2 under stringent conditions.

GCN4 fragments include amino acid sequences of GCN4 shorter than the amino acid sequence of SEQ ID NO: 1.

GCN4 derivatives refer to amino acid sequences of GCN4 longer, either at the N terminal or at the C-terminal, than the amino acid sequence of SEQ ID NO: 1.

A suitable scFv specific to GCN4 is 52SR4 (SEQ ID NO: 3) or a variant thereof (SEQ ID NOs: 98 or 99). Variants of 52SR4 include an amino acid sequence with at least 80%, or 85%, or 90%, or 95%, or 98%, or 99% identity to SEQ ID NO: 3. 52SR4 variants also include an amino acid sequence having at least at least 80%, or 85%, or 90%, or 95%, or 98%, or 99% to a sequence encoded by a nucleotide sequence SEQ ID NO: 4, or a sequence encoded by a nucleotide sequence which hybridises to SEQ ID NO: 4 under stringent conditions.

The present inventors have found that the single chain antibody 52SR4 and peptide GCN4, are a binding pair suitable for use in the multispecific protein complexes of the present disclosure.

Alternatively, any suitable antibody/fragment and antigen (such as a peptide) may be employed as X and Y. Preferably such an X and Y pair result in greater than 75% heterodimer when A-X and Y-B are combined in a 1:1 molar ratio.

In one embodiment, the first binding partner (X) and the second binding partner (Y) are a protein.

In one embodiment, the first binding partner (X) is an enzyme or an active fragment thereof and the second binding partner (Y) is a ligand or vice versa.

In one embodiment, the first binding partner (X) is an enzyme or an active fragment thereof and the second binding partner (Y) is an inhibitor of that enzyme or vice versa.

"Active fragment" as employed herein refers to an amino acid fragment, which is less than the whole amino acid sequence for the entity and retains essentially the same biological activity or a relevant biological activity, for example greater than 50% activity such as 60%, 70%, 80%, 85%, 90%, 91%, 92%, 93%, 94%, 95%, 96%, 97%, 98%, 99% or 100%.

In another embodiment, the first binding partner X is glutathione (GSH) and the second binding partner Y is glutathione-S-transferase (GST) or vice versa.

In another embodiment, X is Fos and Y is Jun or vice versa.

In another embodiment, X is His and Y is anti-His or vice versa.

In another embodiment, the binding pair is clamodulin binding peptide and Y is calmodulin or vice versa.

In another embodiment, X is maltose-binding protein and Y is an anti-maltose binding protein or fragment thereof or vice versa.

Other enzyme-ligand combinations are also contemplated for use in binding partners. Also suitable are affinity tags known in the art for protein purification because these have a tendency to bind with high affinity to their respective binding partners.

"Identity", as used herein, indicates that at any particular position in the aligned sequences, the amino acid residue is identical between the sequences. "Similarity", as used herein, indicates that, at any particular position in the aligned sequences, the amino acid residue is of a similar type between the sequences. For example, leucine may be substituted for isoleucine or valine. Other amino acids which can often be substituted for one another include but are not limited to:

- phenylalanine, tyrosine and tryptophan (amino acids having aromatic side chains);
- lysine, arginine and histidine (amino acids having basic side chains);
- aspartate and glutamate (amino acids having acidic side chains);
- asparagine and glutamine (amino acids having amide side chains); and
- cysteine and methionine (amino acids having sulphur-containing side chains).

Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987, Sequence Analysis Primer, Gribskov, M. and Devereux, J., eds., M Stockton Press, New York, 1991, the BLAST™ software available from NCBI (Altschul, S. F. et al., 1990, J. Mol. Biol. 215:403-410; Gish, W. & States, D. J. 1993, Nature Genet. 3:266-272. Madden, T. L. et al., 1996, Meth. Enzymol. 266:131-141; Altschul, S. F. et al., 1997, Nucleic Acids Res. 25:3389-3402; Zhang, J. & Madden, T. L. 1997, Genome Res. 7:649-656,).

In one embodiment, the first and second fusion proteins comprise one or more peptide linkers. The linkers may be incorporated at various locations in the fusion proteins. For example, a linker may be introduced between a binding partner and the protein attached thereto.

In one embodiment, the linker is a peptide linker.

The term "peptide linker" as used herein refers to a peptide with an amino acid sequence. A range of suitable peptide linkers will be known to the person of skill in the art.

In one embodiment, the binding partners of the multispecific protein complexes are joined to their respective proteins via peptide linkers. Examples of peptide linkers are shown in SEQ ID NOs; 5 to 74 (Tables 2, 3 and 4).

In one embodiment the fusion proteins are a translational fusion, that is a fusion protein expressed in a host cell comprising a genetic construct from which the fusion protein is expressed.

In one embodiment the fusion protein is prepared by fusing the heavy chain of A to X and/or the heavy chain of B to Y optionally via a peptide linker.

In one embodiment, the peptide linker is 50 amino acids in length or less, for example 20 amino acids or less.

Generally it will be more efficient to express the fusion protein recombinantly and therefore a direct peptide bond or a peptide linker that can be expressed by a host cell may be advantageous.

In one embodiment, the linker is selected from a sequence shown in sequence 5 to 72 or PPP.

TABLE 2

| SEQ ID NO: | SEQUENCE |
|---|---|
| 5 | DKTHTCAA |
| 6 | DKTHTCPPCPA |
| 7 | DKTHTCPPCPATCPPCPA |
| 8 | DKTHTCPPCPATCPPCPATCPPCPA |
| 9 | DKTHTCPPCPAGKPTLYNSLVMSDTAGTCY |
| 10 | DKTHTCPPCPAGKPTHVNVSVVMAEVDGTCY |
| 11 | DKTHTCCVECPPCPA |
| 12 | DKTHTCPRCPEPKSCDTPPPCPRCPA |
| 13 | DKTHTCPSCPA |

TABLE 3

| SEQ ID NO: | SEQUENCE |
|---|---|
| 14 | SGGGGSE |
| 15 | DKTHTS |
| 16 | (S)GGGGS |
| 17 | (S)GGGGSGGGGS |
| 18 | (S)GGGGSGGGGSGGGGS |
| 19 | (S)GGGGSGGGGSGGGGSGGGGS |

TABLE 3-continued

| SEQ ID NO: | SEQUENCE |
|---|---|
| 20 | (S)GGGGSGGGGSGGGGSGGGGSGGGGS |
| 21 | AAAGSG-GASAS |
| 22 | AAAGSG-XGGGS-GASAS |
| 23 | AAAGSG-XGGGSXGGGS-GASAS |
| 24 | AAAGSG-XGGGSXGGGSXGGGS-GASAS |
| 25 | AAAGSG-XGGGSXGGGSXGGGSXGGGS-GASAS |
| 26 | AAAGSG-XS-GASAS |
| 27 | PGGNRGTTTTRRPATTTGSSPGPTQSHY |
| 28 | ATTTGSSPGPT |
| 29 | ATTTGS |
| 30 | AAAAAAAAAAAA |
| 31 | EPSGPISTINSPPSKESHKSP |
| 32 | GTVAAPSVFIFPPSD |
| 33 | GGGGIAPSMVGGGGS |
| 34 | GGGGKVEGAGGGGGS |
| 35 | GGGGSMKSHDGGGGS |
| 36 | GGGGNLITIVGGGGS |
| 37 | GGGGVVPSLPGGGGS |
| 38 | GGEKSIPGGGGS |
| 39 | RPLSYRPPFPFGFPSVRP |
| 40 | YPRSIYIRRRHPSPSLTT |
| 41 | TPSHLSHILPSFGLPTFN |
| 42 | RPVSPFTFPRLSNSWLPA |
| 43 | SPAAHFPRSIPRPGPIRT |
| 44 | APGPSAPSHRSLPSRAFG |
| 45 | PRNSIHFLHPLLVAPLGA |
| 46 | MPSLSGVLQVRYLSPPDL |
| 47 | SPQYPSPLTLTLPPHPSL |
| 48 | NPSLNPPSYLHRAPSRIS |
| 49 | LPWRTSLLPSLPLRRRP |
| 50 | PPLFAKGPVGLLSRSFPP |
| 51 | VPPAPVVSLRSAHARPPY |
| 52 | LRPTPPRVRSYTCCPTP- |
| 53 | PNVAHVLPLLTVPWDNLR |
| 54 | CNPLLPLCARSPAVRTFP |

(S) is optional in sequences 17 to 20. Another linker may be peptide sequence GS.

Examples of rigid linkers include the peptide sequences GAPAPAAPAPA (SEQ ID NO: 69), PPPP (SEQ ID NO: 70) and PPP.

Other linkers are shown in Table 4.

TABLE 4

| SEQ ID NO: | SEQUENCE |
|---|---|
| 55 | DLCLRDWGCLW |
| 56 | DICLPRWGCLW |
| 57 | MEDICLPRWGCLWGD |
| 58 | QRLMEDICLPRWGCLWEDDE |
| 59 | QGLIGDICLPRWGCLWGRSV |
| 60 | QGLIGDICLPRWGCLWGRSVK |
| 61 | EDICLPRWGCLWEDD |
| 62 | RLMEDICLPRWGCLWEDD |
| 63 | MEDICLPRWGCLWEDD |
| 64 | MEDICLPRWGCLWED |
| 65 | RLMEDICLARWGCLWEDD |
| 66 | EVRSFCTRWPAEKSCKPLRG |
| 67 | RAPESFVCYWETICFERSEQ |
| 68 | EMCYFPGICWM |

In one aspect, there is provided a method of producing a multispecific protein complex of the present disclosure, comprising the steps of:
(a) producing a first fusion protein (A-X), comprising a first protein (A), attached to a first binding partner (X) of a binding pair;
(b) producing a second fusion protein (B-Y), comprising a second protein (B), attached to a second binding partner (Y) of a binding pair; and
(c) mixing the first (A-X) and second fusion proteins (B-Y) prepared in step a) and b) together.

Typically the mixing of (A-X)$_2$ and B-Y in step (c) is in a 1:2 molar ratio.

In one embodiment each fusion protein employed in the complexes of the present disclosure is produced by expression in a host cell or host cells in an expression experiment.

In one aspect, there is provided a method of preparing a multispecific protein complex of the present disclosure, comprising the steps of:
(a) expressing a first fusion protein (A-X), comprising a first protein (A), attached to a first binding partner (X) of a binding pair;
(b) expressing a second fusion protein (B-Y), comprising a second protein (B), attached to a second binding partner (Y) of a binding pair;
wherein fusion protein A-X and B-Y are expressed from the same host cell or distinct host cells.

Distinct host cells as employed herein refer to individual cells, including cells of the same type (even same clonal type).

In one embodiment the expression is transient expression. The use of transient expression is highly advantageous when combined with the ability to generate multispecific complexes without recourse to purification. This results in a rapid method to generate multispecific protein complexes as transient transfection is much simpler and less resource intensive than stable transfection.

In one embodiment the expression is stable expression i.e. wherein the DNA encoding the fusion protein in question is stably integrated into the host cell genome.

In one embodiment a polynucleotide encoding A-X and a polynucleotide encoding B-Y on the same or different polynucleotide sequences are transfected into a cell as part of a functional assay, wherein the proteins are expressed in the cell and/or released therefrom. In particular the polynucleotides are transiently transfected on the same of different plasmids.

The mixing of $(A-X)_2$ and B-Y is generally effected in conditions where the X and Y can interact. In one embodiment, the fusion proteins are incubated in cell culture media under cell culturing conditions, for example the fusion proteins are incubated for 90 minutes in a 37° C./5% $CO_2$ environment.

In one embodiment the fusion proteins of the present disclosure are mixed in an aqueous environment, for example one fusion protein may be bound to a solid surface such as a bead or a plate and the other fusion protein can be introduced thereto in an aqueous solution/suspension. The solid phase allows excess components and reagents to be washed away readily. In one embodiment neither fusion is attached a solid phase and are simply mixed in a liquid/solution/medium. Thus in one embodiment A-X and B-Y are mixed as free proteins in an aqueous media.

Advantageously, the method of the present disclosure can be employed to prepare complexes formed between heterogenous pairs (i.e. between the first fusion protein [A-X]2 and second fusion protein [B-Y]) wherein interactions between homogenous pairs (i.e. between two first fusion proteins [A-X]2 or two second fusion proteins [B-Y]) are minimised. Thus the present method allows large numbers of multispecific protein complexes to be prepared, with minimal or no contamination with homodimeric complexes. An advantage of the constructs and method of the present disclosure is that the ratio of A-X to B-Y is controlled by the properties of the A-X and B-Y and in particular a molar ratio of 1:1 can be achieved, which equated to 1 $(A-X)_2$ to 2 B-Ys.

In one embodiment a method of the present disclosure comprises a further step of transferring a pair of variable regions (in particular two pairs of variable regions) identified as having synergistic activity into an alternative multispecific format, optionally humanising said variable regions if necessary beforehand, which is an alternative therapeutic format and/or a format having an extended half-life suitable for testing in assays with a longer duration (for example which run a week or more).

Multivalent formats include those known in the art and those described herein, such as DVD-Igs, FabFvs for example as disclosed in WO2009/040562 and WO2010/035012, diabodies, triabodies, tetrabodies etc.

Other examples of bi and multispecific formats (including therapeutic formats) include a diabody, triabody, tetrabody, tandem scFv, tandem scFv-Fc, FabFv, Fab'Fv, FabdsFv, Fab-scFv, Fab'-scFv, diFab, diFab', scdiabody, scdiabody-Fc, scFv-Fc-scFv, scdiabody-$CH_3$, IgG-scFv, scFv-IgG, V-IgG, IgG-V, DVD-Ig, and DuoBody.

Diabody as employed herein refers to two Fv pairs: VH/VL and a further VH/VL pair which have two inter-Fv linkers, such that the VH of a first Fv is linked to the VL of the second Fv and the VL of the first Fv is linked to the VH of the second Fv.

Triabody as employed herein refers to a format similar to the diabody comprising three Fv pairs and three inter-Fv linkers.

Tetrabody as employed herein refers to a format similar to the diabody comprising fours Fv pairs and four inter-Fv linkers.

Tandem scFv as employed herein refers to two scFvs (each comprising a linker is the usual manner) linked to each other via a single linker such that there is a single inter-Fv linker.

Tandem scFv-Fc as employed herein refers to two tandem scFvs, wherein each one is appended to the N-terminus of a CH2 domain, for example via a hinge, of constant region fragment —CH2CH3.

FabFv as employed herein refers to a Fab fragment with a variable region appended to the C-terminal of each of the following, the CH1 of the heavy chain and CL of the light chain. The format may be provided as a PEGylated version thereof.

Fab'Fv as employed herein is similar to FabFv, wherein the Fab portion is replaced by a Fab'. The format may be provided as a PEGylated version thereof.

FabdsFv as employed herein refers to a FabFv wherein an intra-Fv disulfide bond stabilises the appended C-terminal variable regions. The format may be provided as a PEGylated version thereof.

Fab-scFv as employed herein is a Fab molecule with a scFv appended on the C-terminal of the light or heavy chain.

Fab'-scFv as employed herein is a Fab' molecule with a scFv appended on the C-terminal of the light or heavy chain.

DiFab as employed herein refers to two Fab molecules linked via their C-terminus of the heavy chains.

DiFab' as employed herein refers to two Fab' molecules linked via one or more disulfide bonds in the hinge region thereof.

As employed herein scdiabody is a diabody comprising an intra-Fv linker, such that the molecule comprises three linkers and forms a normal scFv whose VH and VL terminals are each linked to a one of the variable regions of a further Fv pair.

Scdiabody-Fc as employed herein is two scdiabodies, wherein each one is appended to the N-terminus of a CH2 domain, for example via a hinge, of constant region fragment —CH2CH3.

ScFv-Fc-scFv as employed herein refers to four scFvs, wherein one of each is appended to the N-terminus and the C-terminus of both the heavy and light chain of a —CH2CH3 fragment.

Scdiabody-CH3 as employed herein refers to two scdiabody molecules each linked, for example via a hinge to a CH3 domain.

IgG-scFv as employed herein is a full length antibody with a scFv on the C-terminal of each of the heavy chains or each of the light chains.

scFv-IgG as employed herein is a full length antibody with a scFv on the N-terminal of each of the heavy chains or each of the light chains.

V-IgG as employed herein is a full length antibody with a variable domain on the N-terminal of each of the heavy chains or each of the light chains.

IgG-V as employed herein is a full length antibody with a variable domain on the C-terminal of each of the heavy chains or each of the light chains DVD-Ig (also known as dual V domain IgG) is a full length antibody with 4 additional variable domains, one on the N-terminus of each heavy and each light chain.

Duobody or 'Fab-arm exchange' as employed herein is a multispecific IgG antibody format where matched and complementary engineered amino acid changes in the constant domains (typically CH3) of two different monoclonal antibodies lead, upon mixing, to the formation of heterodimers. A heavy/light chain pair from the first antibody will, as a result of the residue engineering, prefer to associate with a heavy:light chain pair of a second antibody.

If present constant region domains of a multispecific antibody complex or antibody molecule of the present disclosure, if present, may be selected having regard to the proposed function of the complex or antibody molecule, and in particular the effector functions which may be required. For example, the constant region domains may be human IgA, IgD, IgE, IgG or IgM domains. In particular, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required. It will be appreciated that sequence variants of these constant region domains may also be used. For example IgG4 molecules in which the serine at position 241 has been changed to proline as described in Angal et al., 1993, Molecular Immunology, 1993, 30:105-108 may be used. Accordingly, in the embodiment where the antibody is an IgG4 antibody, the antibody may include the mutation S241P.

It will also be understood by one skilled in the art that antibodies may undergo a variety of posttranslational modifications. The type and extent of these modifications often depends on the host cell line used to express the antibody as well as the culture conditions. Such modifications may include variations in glycosylation, methionine oxidation, diketopiperazine formation, aspartate isomerization and asparagine deamidation. A frequent modification is the loss of a carboxy-terminal basic residue (such as lysine or arginine) due to the action of carboxypeptidases (as described in Harris, R J. Journal of Chromatography 705: 129-134, 1995). Accordingly, the C-terminal lysine of the antibody heavy chain may be absent.

The present disclosure also provides a composition comprising one or more multispecific protein complexes as described above, wherein the composition predominantly comprises heterodimeric multispecific complexes according to the present disclosure, for example with minimal or no contamination with homodimeric complexes.

In one embodiment, at least 60%, at least 65%, at least 70%, at least 75%, at least 80%, at least 90%, or at least 95% of the fusion proteins in the composition are in a multispecific protein complex form.

In one embodiment, at least 60% of the fusion proteins in the composition are in a multispecific protein complex form.

In one embodiment the complexes formed require no further purification steps and thus the compositions comprise unpurified multispecific complexes.

In one embodiment the complexes formed require one purification step, for example column chromatography.

In one embodiment the method further comprises at least one purification step, for example after expression of a fusion protein according to the present disclosure and before mixing the fusion proteins.

In one aspect the present disclosure relates to a fusion protein, a heterodimerically-tethered multispecific protein complex, a composition comprising a fusion protein or said multispecific protein complex, a multiple, array, library as defined herein.

In one embodiment, the multispecific protein complex is in solution or suspension.

In one embodiment, the multispecific protein complexes are fixed on a solid substrate surface.

In one embodiment, the multiplex is in the form of an array, for example in a microplate, such as a 96 or 384 well plate. Such arrays can be readily implemented in screening assays to identify multispecific protein complexes with desired functionality.

In another embodiment, the multispecific protein complexes are conjugated to beads.

A fusion protein as defined above is a component of the multispecific protein complex according to the present disclosure. In one aspect, the present disclosure relates to a fusion protein described herein.

In a further aspect, there is provided a library, comprising two or more fusion proteins as defined above.

The term "library" as used herein refers to two or more multispecific antibody complexes of the present disclosure or multiple fusion proteins of the present disclosure that can be combined to form at least two different multispecific antibody complexes according to the present disclosure. As described throughout the specification, the term "library" is used in its broadest sense and may also encompass sub-libraries.

Advantageously, the library may comprise a range of different fusion proteins which have either the first binding partner (X) or second binding partner (Y) of a particular binding pair attached thereto. In one embodiment part of the library comprises proteins/antibodies/fragments each connected to a binding partner X and the remainder of the library comprises the same proteins/antibodies/fragments each connected to a binding partner Y. This thus allows any two fusion proteins to be readily combined to form a multispecific protein complex of the present disclosure, as long as one fusion protein has the first binding partner of a binding pair attached and the other fusion protein has the second binding partner of the binding pair attached.

In one embodiment multispecific protein complexes of the present invention are suitable for therapeutic applications and may provide novel therapies for treating diseases. Thus in a further aspect, there is provided a multispecific protein complex as described above for use in therapy. The multispecific protein complex is suitable for treating a range of diseases, such as autoimmune disease and cancer.

Conversely, the multispecific protein complexes of the present disclosure can be engineered with one antibody or antibody fragment specific for T-lymphocytes, and another antibody or antibody fragment specific for a cancer-specific antigen. As a result, the multispecific antibody complexes of the present disclosure may advantageously possess a higher cytotoxic potential compared to ordinary monoclonal antibodies.

The multispecific protein complexes of the present disclosure are also particularly suited for inhibiting B cell function in order to control immune and autoimmune reactions in various autoimmune diseases.

Thus, the present disclosure extends to a method of treating a disease in a patient, comprising the administration of a multispecific protein complex of the present disclosure.

In one aspect, there is provided a pharmaceutical composition comprising one or more multispecific protein complexes of the present disclosure.

In one embodiment there is provided a fusion protein obtained or obtainable for a method of the present disclosure.

In one embodiment there is provided an multispecific antibody complex obtained or obtainable from a method of the present disclosure In one embodiment there is provided a multispecific or multispecific antibody molecule comprising variable regions combinations identified by a method according to the present disclosure.

In one embodiment there is provided a composition, such as a pharmaceutical composition comprising a fusion protein, a multispecific antibody complex or a multispecific/multispecific antibody molecule obtained from a method of the present disclosure.

Various different components can be included in the composition, including pharmaceutically acceptable carriers, excipients and/or diluents. The composition may, optionally, comprise further molecules capable of altering the characteristics of the population of antibodies of the invention thereby, for example, reducing, stabilizing, delaying, modulating and/or activating the function of the antibodies. The composition may be in solid, or liquid form and may inter alia, be in the form of a powder, a tablet, a solution or an aerosol.

The present disclosure also provides a pharmaceutical or diagnostic composition comprising a multispecific protein complex of the present invention in combination with one or more of a pharmaceutically acceptable excipient, diluent or carrier. Accordingly, provided is the use of a multispecific protein complex of the invention for use in the treatment and for the manufacture of a medicament for the treatment of a pathological condition or disorder.

The pathological condition or disorder, may, for example be selected from the group consisting of infections (viral, bacterial, fungal and parasitic), endotoxic shock associated with infection, arthritis such as rheumatoid arthritis, asthma such as severe asthma, chronic obstructive pulmonary disease (COPD), pelvic inflammatory disease, Alzheimer's Disease, inflammatory bowel disease, Crohn's disease, ulcerative colitis, Peyronie's Disease, coeliac disease, gallbladder disease, Pilonidal disease, peritonitis, psoriasis, vasculitis, surgical adhesions, stroke, Type I Diabetes, lyme disease, meningoencephalitis, autoimmune uveitis, immune mediated inflammatory disorders of the central and peripheral nervous system such as multiple sclerosis, lupus (such as systemic lupus erythematosus) and Guillain-Barr syndrome, Atopic dermatitis, autoimmune hepatitis, fibrosing alveolitis, Grave's disease, IgA nephropathy, idiopathic thrombocytopenic purpura, Meniere's disease, pemphigus, primary biliary cirrhosis, sarcoidosis, scleroderma, Wegener's granulomatosis, other autoimmune disorders, pancreatitis, trauma (surgery), graft-versus-host disease, transplant rejection, heart disease including ischaemic diseases such as myocardial infarction as well as atherosclerosis, intravascular coagulation, bone resorption, osteoporosis, osteoarthritis, periodontitis, hypochlorhydia and cancer, including breast cancer, lung cancer, gastric cancer, ovarian cancer, hepatocellular cancer, colon cancer, pancreatic cancer, esophageal cancer, head & neck cancer, kidney, and cancer, in particular renal cell carcinoma, prostate cancer, liver cancer, melanoma, sarcoma, myeloma, neuroblastoma, placental choriocarcinoma, cervical cancer, and thyroid cancer, and the metastatic forms thereof.

The present disclosure also provides a pharmaceutical or diagnostic composition comprising a multispecific protein complex of the present invention in combination with one or more of a pharmaceutically acceptable excipient, diluent or carrier. Accordingly, provided is the use of a multispecific protein complex of the invention for use in treatment and in the manufacture of a medicament.

The composition will usually be supplied as part of a sterile, pharmaceutical composition that will normally include a pharmaceutically acceptable carrier. A pharmaceutical composition of the present invention may additionally comprise a pharmaceutically-acceptable adjuvant.

The present invention also provides a process for preparation of a pharmaceutical or diagnostic composition comprising adding and mixing the antibody molecule or multispecific antibody complex of the present invention together with one or more of a pharmaceutically acceptable excipient, diluent or carrier.

The term "pharmaceutically acceptable excipient" as used herein refers to a pharmaceutically acceptable formulation carrier, solution or additive to enhance the desired characteristics of the compositions of the present disclosure. Excipients are well known in the art and include buffers (e.g., citrate buffer, phosphate buffer, acetate buffer and bicarbonate buffer), amino acids, urea, alcohols, ascorbic acid, phospholipids, proteins (e.g., serum albumin), EDTA, sodium chloride, liposomes, mannitol, sorbitol, and glycerol. Solutions or suspensions can be encapsulated in liposomes or biodegradable microspheres. The formulation will generally be provided in a substantially sterile form employing sterile manufacture processes.

This may include production and sterilization by filtration of the buffered solvent solution used for the formulation, aseptic suspension of the antibody in the sterile buffered solvent solution, and dispensing of the formulation into sterile receptacles by methods familiar to those of ordinary skill in the art.

The pharmaceutically acceptable carrier should not itself induce the production of antibodies harmful to the individual receiving the composition and should not be toxic. Suitable carriers may be large, slowly metabolised macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Such carriers enable the pharmaceutical compositions to be formulated as tablets, pills, dragées, capsules, liquids, gels, syrups, slurries and suspensions, for ingestion by the patient.

The multispecific protein complexes of the invention can be delivered dispersed in a solvent, e.g., in the form of a solution or a suspension. It can be suspended in an appropriate physiological solution, e.g., physiological saline, a pharmacologically acceptable solvent or a buffered solution. Buffered solutions known in the art may contain 0.05 mg to 0.15 mg disodium edetate, 8.0 mg to 9.0 mg NaCl, 0.15 mg to 0.25 mg polysorbate, 0.25 mg to 0.30 mg anhydrous citric acid, and 0.45 mg to 0.55 mg sodium citrate per 1 ml of water so as to achieve a pH of about 4.0 to 5.0. As mentioned supra a suspension can made, for example, from lyophilised antibody.

A thorough discussion of pharmaceutically acceptable carriers is available in Remington's Pharmaceutical Sciences (Mack Publishing Company, N.J. 1991).

The multispecific antibody complex (or multispecific/multispecific antibody molecule of the present disclosure) may be the sole active ingredient in the pharmaceutical or diagnostic composition or may be accompanied by other active ingredients including other antibody ingredients, for example anti-TNF, anti-IL-1β, anti-T cell, anti-IFNγ or anti-LPS antibodies, or non-antibody ingredients such as xanthines. Other suitable active ingredients include antibodies capable of inducing tolerance, for example, anti-CD3 or anti-CD4 antibodies. In a further embodiment, the antibody, fragment or composition according to the disclosure is employed in combination with a further pharmaceutically active agent, for example a corticosteroid (such as fluticasone propionate) and/or a beta-2-agonist (such as salbutamol, salmeterol or formoterol) or inhibitors of cell growth and proliferation (such as rapamycin, cyclophosphmide, methotrexate) or alternatively a CD28 and/or CD40 inhibitor. In one embodiment the inhibitor is a small molecule. In another embodiment the inhibitor is an antibody specific to the target.

The pharmaceutical compositions suitably comprise a therapeutically effective amount of the multispecific antibody complex of the invention (or a multispecific/multispecific antibody molecule of the present disclosure).

The term "therapeutically effective amount" as used herein refers to an amount of a therapeutic agent needed to treat, ameliorate or prevent a targeted disease or condition, or to exhibit a detectable therapeutic or preventative effect. For any antibody, the therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgement of the clinician. Generally, a therapeutically effective amount will be from 0.01 mg/kg to 50 mg/kg, for example 0.1 mg/kg to 20 mg/kg. Alternatively, the dose may be 1 to 500 mg per day such as 10 to 100, 200, 300 or 400 mg per day. Pharmaceutical compositions may be conveniently presented in unit dose forms containing a predetermined amount of an active agent of the invention.

Compositions may be administered individually to a patient or may be administered in combination (e.g. simultaneously, sequentially or separately) with other agents, drugs or hormones.

The dose at which the antibody molecule of the present invention is administered depends on the nature of the condition to be treated, the extent of the inflammation present and on whether the antibody molecule is being used prophylactically or to treat an existing condition. The frequency of dose will depend on the half-life of the antibody molecule and the duration of its effect. If the antibody molecule has a short half-life (e.g. 2 to 10 hours) it may be necessary to give one or more doses per day. Alternatively, if the antibody molecule has a long half-life (e.g. 2 to 15 days) it may only be necessary to give a dosage once per day, once per week or even once every 1 or 2 months.

In the present disclosure, the pH of the final formulation is not similar to the value of the isoelectric point of the antibody or fragment, for if the pH of the formulation is 7 then a pI of from 8-9 or above may be appropriate. Whilst not wishing to be bound by theory it is thought that this may ultimately provide a final formulation with improved stability, for example the antibody or fragment remains in solution.

The pharmaceutical compositions of this invention may be administered by any number of routes including, but not limited to, oral, intravenous, intramuscular, intra-arterial, intramedullary, intrathecal, intraventricular, transdermal, transcutaneous (for example, see WO98/20734), subcutaneous, intraperitoneal, intranasal, enteral, topical, sublingual, intravaginal or rectal routes. Hyposprays may also be used to administer the pharmaceutical compositions of the invention.

Direct delivery of the compositions will generally be accomplished by injection, subcutaneously, intraperitoneally, intravenously or intramuscularly, or delivered to the interstitial space of a tissue. The compositions can also be administered into a specific tissue of interest. Dosage treatment may be a single dose schedule or a multiple dose schedule.

Where the product is for injection or infusion, it may take the form of a suspension, solution or emulsion in an oily or aqueous vehicle and it may contain formulatory agents, such as suspending, preservative, stabilising and/or dispersing agents. Alternatively, the multispecific protein complex (or multispecific/multispecific antibody molecule of the present disclosure) may be in dry form, for reconstitution before use with an appropriate sterile liquid. If the composition is to be administered by a route using the gastrointestinal tract, the composition will need to contain agents which protect the antibody from degradation but which release the multispecific protein complex once it has been absorbed from the gastrointestinal tract.

A nebulisable formulation according to the present disclosure may be provided, for example, as single dose units (e.g., sealed plastic containers or vials) packed in foil envelopes. Each vial contains a unit dose in a volume, e.g., 2 ml, of solvent/solution buffer.

The term "variant" as used herein refers to peptide or protein that contains at least one amino acid sequence or nucleotide sequence alteration as compared to the amino acid or nucleotide sequence of the corresponding wild-type peptide or protein. A variant may comprise at least 80%, or 85%, or 90%, or 95%, or 98% or 99% sequence identity to the corresponding wild-type peptide or protein. However, it is possible for a variant to comprise less than 80% sequence identity, provided that the variant exhibits substantially similar function to its corresponding wild-type peptide or protein.

Antigens include cell surface receptors such as T cell or B cell signalling receptors, co-stimulatory molecules, checkpoint inhibitors, natural killer cell receptors, Immunolglobulin receptors, TNFR family receptors, B7 family receptors, adhesion molecules, integrins, cytokine/chemokine receptors, GPCRs, growth factor receptors, kinase receptors, tissue-specific antigens, cancer antigens, pathogen recognition receptors, complement receptors, hormone receptors or soluble molecules such as cytokines, chemokines, leukotrienes, growth factors, hormones or enzymes or ion channels, epitopes, fragments and post translationally modified forms thereof.

In one embodiment, the multispecific protein complex comprises one or two cell surface receptor specificities.

In one embodiment, the multispecific protein complex comprises one or two cytokine or chemokine specificities.

Antibodies or fragments to a pair of targets identified by the method according to the present disclosure may be incorporated into any format suitable for use as a laboratory reagent, an assay reagent or a therapeutic.

Thus in one aspect the disclosure extends to use of antibodies fragments or combinations thereof as pairs in any format, examples of which are given above.

The disclosure also extends to compositions, such as pharmaceutical compositions comprising said novel formats with the particular antigen specificity.

In a further aspect the disclosure includes use of the formats and the compositions in treatment.

In one embodiment, the multispecific protein complex of the present disclosure may be used to functionally alter the activity of the antigen or antigens of interest. For example, the multispecific protein complex may neutralize, antagonize or agonise the activity of said antigen or antigens, directly or indirectly.

The present disclosure also extends to a kit, for example comprising:
a) one or more fusion proteins $(A-X)_2$ comprising a first antibody (A) attached to a first binding partner of a binding pair (X); and
b) one or more fusion proteins (B-Y) comprising a second antibody or antibody fragment (B) attached to a second binding partner of the binding pair (Y), wherein the latter is specific for the first binding partner;
  for example wherein the first binding partner (X) is a peptide or polypeptide and the second binding (Y) partner is an antibody or antibody fragment specific thereto;
wherein Y the second binding partner is specific to the first binding partner X and the second binding partner is, for example an antibody or antibody fragment specific thereto; and the specific interaction (such as a binding interaction) of the two binding partners forms a heterodimer-tether which physically brings the two fusion proteins from a) and b) together to form a multispecific protein complex; and
wherein the fusion protein(s) is/are in a complexed or a non-complexed form.

Advantageously, the kit may comprise multispecific protein complexes of the present disclosure, or may comprise fusion proteins which are in a complexed or non-complexed form. In the former case, the multispecific protein complexes are ready for use "out of the box" which provides convenience and ease of use, whereas in the latter case, the multispecific protein complexes can be assembled according to the user's requirements by combining different fusion proteins.

In another embodiment, the kit further comprises instructions for use.

In yet another embodiment, the kit further comprises one or more reagents for performing one or more functional assays.

In one embodiment, fusion proteins, multispecific proteins complexes, multiplexes, grids, libraries, compositions etc as described herein are for use as a laboratory reagent.

In a further aspect, there is provided a nucleotide sequence, for example a DNA sequence encoding a fusion protein and/or a multispecific protein complex as defined above.

In one embodiment, there is provided a nucleotide sequence, for example a DNA sequence encoding a multispecific protein complex according to the present disclosure.

In one embodiment there is provided a nucleotide sequence, for example a DNA sequence encoding a multispecific or multispecific antibody molecule according to the present disclosure.

The disclosure herein also extends to a vector comprising a nucleotide sequence as defined above.

The term "vector" as used herein refers to a nucleic acid molecule capable of transporting another nucleic acid to which it has been linked. An example of a vector is a "plasmid," which is a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell, where they are subsequently replicated along with the host genome. In the present specification, the terms "plasmid" and "vector" may be used interchangeably as a plasmid is the most commonly used form of vector.

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing.

The term "selectable marker" as used herein refers to a protein whose expression allows one to identify cells that have been transformed or transfected with a vector containing the marker gene. A wide range of selection markers are known in the art. For example, typically the selectable marker gene confers resistance to drugs, such as G418, hygromycin or methotrexate, on a host cell into which the vector has been introduced. The selectable marker can also be a visually identifiable marker such as a fluorescent marker for example. Examples of fluorescent markers include rhodamine, FITC, TRITC, Alexa Fluors and various conjugates thereof.

Also provided is a host cell comprising one or more cloning or expression vectors comprising one or more DNA sequences encoding an antibody of the present disclosure. Any suitable host cell/vector system may be used for expression of the DNA sequences encoding the antibody molecule of the present disclosure. Bacterial, for example *E. coli*, and other microbial systems may be used or eukaryotic, for example mammalian, host cell expression systems may also be used. Suitable mammalian host cells include CHO, myeloma or hybridoma cells.

The present disclosure also provides a process for the production of a fusion protein according to the present disclosure comprising culturing a host cell containing a vector of the present disclosure under conditions suitable for leading to expression of protein from DNA encoding the molecule of the present disclosure, and isolating the molecule.

The multispecific protein complexes of the present disclosure may be used in diagnosis/detection kits, wherein multispecific protein complexes with particular combinations of antigen specificities are used. For example, the kits may comprise multispecific antibody complexes that are specific for two antigens, both of which are present on the same cell type, and wherein a positive diagnosis can only be made if both antigens are successfully detected. By using the multispecific antibody complexes of the present disclosure rather than two separate antibodies or antibody fragments in a non-complexed form, the specificity of the detection can be greatly enhanced.

In one embodiment, the multispecific antibody complexes are fixed on a solid surface. The solid surface may for example be a chip, or an ELISA plate.

Further provided is the use of a multispecific protein complex of the present disclosure for detecting in a sample the presence of a first and a second peptide, whereby the multispecific complexes are used as detection agents.

The multispecific antibody complexes of the present disclosure may for example be conjugated to a fluorescent marker which facilitates the detection of bound antibody-antigen complexes. Such multispecific antibody complexes can be used for immunofluorescence microscopy. Alternatively, the multispecific antibody complexes may also be used for western blotting or ELISA.

In one embodiment, there is provided a process for purifying an antibody (in particular an antibody or fragment according to the invention).

In one embodiment, there is provided a process for purifying a fusion protein or multispecific protein complex according the present disclosure comprising the steps: performing anion exchange chromatography in non-binding mode such that the impurities are retained on the column and the antibody is maintained in the unbound fraction. The step may, for example be performed at a pH about 6-8.

The process may further comprise an initial capture step employing cation exchange chromatography, performed for example at a pH of about 4 to 5.

The process may further comprise of additional chromatography step(s) to ensure product and process related impurities are appropriately resolved from the product stream.

The purification process may also comprise of one or more ultra-filtration steps, such as a concentration and diafiltration step.

"Purified form" as used supra is intended to refer to at least 90% purity, such as 91, 92, 93, 94, 95, 96, 97, 98, 99% w/w or more pure.

In the context of this specification "comprising" is to be interpreted as "including".

Aspects of the disclosure comprising certain elements are also intended to extend to alternative embodiments "consisting" or "consisting essentially" of the relevant elements. Positive embodiments employed herein may serve basis for the excluding certain aspects of the disclosure.

Disclosures in the context of the method relating to the multispecific complexes apply equally to the complexes per se and vice versa.

EXAMPLES

Figure 3:
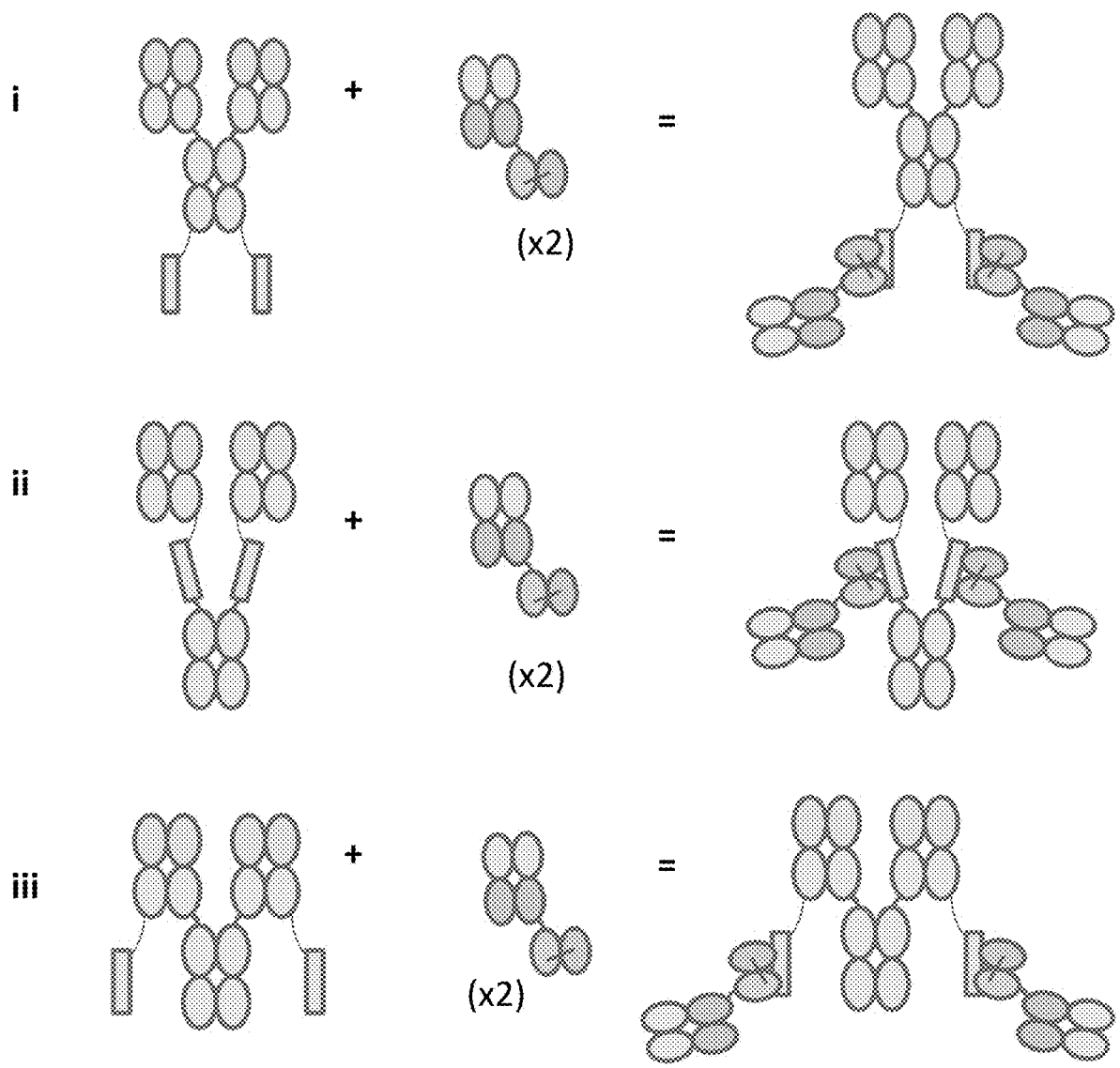
FIG. 3 Is a diagrammatic representation of a heterodimerically-tethered multispecific protein complexes and components/units thereof according to the present disclosure.

Example 1 Construction of a Multispecific Antibody Complex of the Present Disclosure FIG. 3 shows some representative bispecific antibody complexes of the present disclosure. The bispecific antibody complex is composed of a first and second fusion protein.

The first fusion protein A-X is half a full length antibody which dimerises to generate a full length antibody $(A-X)_2$ with specificity to a given antigen. Each half of the full length antibody is attached to X, a peptide, via a peptide linker which is linked to either the c-terminal of the CL domain of the antibody (iii), the C-terminal of the heavy chain of the antibody (i) or is inserted between CH1 and CH2 of the full length antibody (ii). X may be any peptide such as the peptide GCN4 (clone 7P14P SEQ ID NO: 1)

The second fusion protein B-Y includes a Fab fragment (Fab B with specificity to a given antigen). However, in comparison to the first protein, the Fab fragment is attached to Y, a scFv (clone 52SR4 SEQ ID NO:3) via a peptide linker which is linked to the $CH_1$ domain of the Fab fragment.

The scFv, Y, is specific for and complementary to the binding partner X, peptide GCN4. As a result, when the two fusion proteins are brought into contact with each other, a non-covalent binding interaction between the scFv and GCN4 peptide occurs, thereby physically retaining the two fusion proteins in the form of a multispecific antibody complex. As $(A-X)_2$ contains two X peptides, two B-Y proteins will bind to the $(A-X)_2$ complex, resulting in $(A-X)_2:(Y-B)_2$.

The single chain antibody (scFv) 52SR4 was derived by constructing and panning a ribosome display VL-linker-VH scFv library from the spleens of mice immunized with GCN4(7P14P) (Ribosome display efficiently selects and evolves high-affinity antibodies in vitro from immune libraries. Hanes J, Jermutus L, Weber-Bornhauser S, Bosshard H R, Plückthun A. (1998) Proc. Natl. Acad. Sci. U.S.A. 95, 14130-14135). A further 2004 publication describes the affinity maturation of 52SR4 to a reported 5 pM again using ribosome display of randomised libraries (Directed in Vitro Evolution and Crystallographic Analysis of a Peptide-binding Single Chain Antibody Fragment (scFv) with Low Picomolar Affinity. Zhand C, Spinelli S, Luginbuhl B, Amstutz P, Cambillau C, Pluckthun A. (2004) J. Biol. Chem. 279, 18870-18877).

The GCN4 peptide was derived from the yeast transcription factor GCN4 by inclusion of Proline residues at positions 7 and 14, hence GCN4(7P14P) remains in a monomeric state on scFv binding as described in a 1999 publication by Berger et al (Antigen recognition by conformational selection. Berger C, Weber-Bornhauser S, Eggenberger Y, Hanes J, Pluckthun A, Bosshard H. R. (1999) F.E.B.S. Letters 450, 149-153).

The invention claimed is:

1. A multispecific protein complex having the formula $(A-X)_2:(Y-B)_2$ wherein:
   A-X is a first fusion protein;
   Y-B is a second fusion protein;
   X:Y is a heterodimeric-tether;
   : is a binding interaction between X and Y;
   A is a first protein component of the multispecific protein complex which is one half of a full length antibody comprising a light chain (VLCL) paired with a full length heavy chain (VHCH1CH2CH3);
   B is a second protein component of the multispecific protein complex selected from a Fab or Fab' fragment;
   X is a first binding partner of a binding pair selected from the group consisting of:
   i. an antigen appended to the C-terminal of the light chain or the heavy chain of A, and
   ii. an antigen inserted between CH1 and CH2 of the heavy chain of A; and
   Y is a second binding partner of the binding pair independently selected from a Fab fragment, a Fab' fragment, or a scFv appended to the C-terminal of B;
   wherein Y is a scFv specific to the peptide GCN4 having SEQ ID NO:1 or amino acids 1 to 38 of SEQ ID NO:1 and wherein the scFv is 52SR4 comprising SEQ ID NO:3 or amino acids 1 to 243 of SEQ ID NO:3 or wherein X is a peptide GCN4 having SEQ ID NO:1 or amino acids 1 to 38 of SEQ ID NO:1 and wherein A and B bind to different antigens.

2. The multispecific protein complex according to claim 1 wherein X is:
   the peptide GCN4 comprising SEQ ID NO: 1.

3. The multispecific protein complex according to claim 1, wherein B is a Fab fragment.

4. The multispecific protein complex according to claim 1, wherein X is the peptide:
   a. fused via a linker to the C-terminal of the heavy chain of A or
   b. inserted between CH1 and CH2 of the heavy chain of A.

5. The multispecific protein complex according to claim 1 wherein Y is:
   the scFv comprising SEQ ID NO: 3.

6. The multispecific protein complex according to claim 1, wherein Y is specific to the peptide GCN4 consisitng of (SEQ ID NO:1 or amino acids 1 to 38 of SEQ ID NO:1).

7. The multispecific protein complex according to claim 6, wherein Y is the scFv 52SR4 consisting of (SEQ ID NO:3 or amino acids 1 to 243 of SEQ ID NO:3).

8. The multispecific protein complex according to claim 1, wherein X or Y is a peptide GCN4 consisting of (SEQ ID NO:1 or amino acids 1 to 38 of SEQ ID NO:1).

9. The multispecific protein complex according to claim 1, wherein the scFv has a binding affinity for the peptide GCN4 is 5 nM or 5 pM.

10. A composition comprising one or more multispecific protein complexes defined in claim 1.

11. The multispecific protein complex according to claim 9, wherein the X and Y has a binding affinity of 800, 700, 600, 500, 400 or 300 pM.

* * * * *